United States Patent
Kufeld et al.

(10) Patent No.: US 9,187,383 B2
(45) Date of Patent: Nov. 17, 2015

(54) COMPONENT SEPARATIONS IN POLYMERIZATION

(71) Applicant: Chevron Phillips Chemical Company LP, The Woodlands, TX (US)

(72) Inventors: Scott E. Kufeld, Houston, TX (US); John D. Hottovy, Porter, TX (US); Ai-fu Chang, Humble, TX (US)

(73) Assignee: CHEVRON PHILLIPS CHEMICAL COMPANY LP, The Woodlands, TX (US)

( * ) Notice: Subject to any disclaimer, the term of this patent is extended or adjusted under 35 U.S.C. 154(b) by 0 days.

(21) Appl. No.: 14/700,912

(22) Filed: Apr. 30, 2015

(65) Prior Publication Data
US 2015/0232396 A1 Aug. 20, 2015

Related U.S. Application Data

(63) Continuation of application No. 13/447,003, filed on Apr. 13, 2012, now Pat. No. 9,108,147, which is a continuation-in-part of application No. 12/905,966, filed on Oct. 15, 2010, now Pat. No. 8,410,329.

(51) Int. Cl.
*C07C 7/11* (2006.01)
*C07C 7/00* (2006.01)
(Continued)

(52) U.S. Cl.
CPC . *C07C 7/005* (2013.01); *C07C 4/02* (2013.01); *C07C 4/06* (2013.01); *C07C 5/32* (2013.01); *C07C 7/04* (2013.01); *C07C 7/11* (2013.01)

(58) Field of Classification Search
CPC ........ C07C 7/11; C07C 7/04; B01D 53/1487; B01D 2252/20421; B01D 2252/20468; B01D 2257/7022
USPC .................................. 585/809; 203/42, 81
See application file for complete search history.

(56) References Cited

U.S. PATENT DOCUMENTS 2,610,704 A     9/1952   Patterson
2,921,053 A  *  1/1960   Dye .............................. 528/501
(Continued)

FOREIGN PATENT DOCUMENTS

EP    2018899 A1    1/2009
EP    2083020 A1    7/2009
(Continued)

OTHER PUBLICATIONS

Reine, Travis Allen, Olefin/Paraffin Separation by Reactive Absorption, Dissertation, Dec. 2004, 268 pages.*
(Continued)

*Primary Examiner* — Fred M Teskin
(74) *Attorney, Agent, or Firm* — Conley Rose, P.C.; Rodney B. Carroll; Monte Rhodes

(57) ABSTRACT

A process for component separation in a polymer production system, comprising separating a polymerization product stream into a gas stream and a polymer stream, wherein the gas stream comprises ethane and unreacted ethylene, distilling the gas stream into a light hydrocarbon stream, wherein the light hydrocarbon stream comprises ethane and unreacted ethylene, contacting the light hydrocarbon stream with an absorption solvent system, wherein at least a portion of the unreacted ethylene from the light hydrocarbon stream is absorbed by the absorption solvent system, and recovering a waste gas stream from the absorption solvent system, wherein the waste gas stream comprises ethane, hydrogen, or combinations thereof.

19 Claims, 11 Drawing Sheets

(51) Int. Cl.

| | |
|---|---|
| *C07C 7/156* | (2006.01) |
| *B01D 53/14* | (2006.01) |
| *C07C 7/04* | (2006.01) |
| *C07C 5/32* | (2006.01) |
| *C07C 4/02* | (2006.01) |
| *C07C 4/06* | (2006.01) |
| *C08F 110/02* | (2006.01) |

(56) References Cited

U.S. PATENT DOCUMENTS

| | | |
|---|---|---|
| 3,248,179 A | 4/1966 | Norwood |
| 3,755,487 A | 8/1973 | Jahnig et al. |
| 4,025,574 A | 5/1977 | Tabler et al. |
| 4,501,885 A | 2/1985 | Sherk et al. |
| 4,588,790 A | 5/1986 | Jenkins, III et al. |
| 5,104,570 A | 4/1992 | Cymbaluk et al. |
| 5,191,153 A | 3/1993 | Cymbaluk et al. |
| 5,259,986 A | 11/1993 | Cymbaluk et al. |
| 5,352,749 A | 10/1994 | DeChellis et al. |
| 5,436,304 A | 7/1995 | Griffin et al. |
| 5,455,314 A | 10/1995 | Burns et al. |
| 5,523,512 A | 6/1996 | Cymbaluk et al. |
| 5,565,175 A | 10/1996 | Hottovy et al. |
| 5,575,979 A | 11/1996 | Hanson |
| 5,639,935 A | 6/1997 | Cooper et al. |
| 5,681,908 A | 10/1997 | Mehra et al. |
| 6,221,982 B1 | 4/2001 | Debras et al. |
| 6,225,412 B1 | 5/2001 | Chaffin et al. |
| 6,225,421 B1 | 5/2001 | Promel et al. |
| 6,239,235 B1 | 5/2001 | Hottovy et al. |
| 6,262,191 B1 | 7/2001 | Hottovy et al. |
| 6,291,601 B1 | 9/2001 | Debras |
| 6,468,329 B2 | 10/2002 | Cho et al. |
| 6,730,751 B2 | 5/2004 | Shamshoum et al. |
| 6,833,415 B2 | 12/2004 | Kendrick et al. |
| 7,163,906 B2 | 1/2007 | McDaniel et al. |
| 7,619,047 B2 | 11/2009 | Yang et al. |
| 7,709,585 B1 | 5/2010 | Buchelli et al. |
| 8,410,329 B2 | 4/2013 | Hottovy et al. |
| 2006/0094590 A1 | 5/2006 | McDaniel et al. |
| 2007/0197374 A1 | 8/2007 | Yang et al. |
| 2009/0004417 A1 | 1/2009 | Follestad et al. |
| 2010/0029872 A1 | 2/2010 | Jensen et al. |
| 2010/0041842 A1 | 2/2010 | Yang et al. |
| 2011/0046323 A1* | 2/2011 | Van Der Schrick et al. .... 526/68 |
| 2012/0232231 A1 | 9/2012 | Kufeld et al. |
| 2012/0232232 A1 | 9/2012 | Hottovy et al. |

FOREIGN PATENT DOCUMENTS

| | | |
|---|---|---|
| WO | 2007018506 A1 | 2/2007 |
| WO | 2012051268 A1 | 4/2012 |
| WO | 2013154882 A1 | 10/2013 |
| WO | 2013154907 A2 | 10/2013 |
| WO | 2013154907 A3 | 10/2013 |

OTHER PUBLICATIONS

Chen, Joseph, et al., "A Study of Cu(I)-Ethylene Complexation for Olefin-Paraffin Separation," AIChE Journal, American Institute of Chemical Engineers, vol. 57 No. 3, pp. 630-644, Mar. 2011.

Engineering Data Book, vol. II, Sections 17-26, Tenth Edition, 1987, p. 19-32, Gas Processors Association.

Extractive distillation, Wikipedia, 3 pages, http://en.wikipedia.org/wiki/Extractive_distillation, last viewed Jan. 28, 2011.

File: simple distillation apparatus.svg, Wikipedia, 5 pages, http://en.wikipedia.org/wiki/File:Simple_distillation_apparatus.svg, last viewed Mar. 2, 2010.

Foreign communication from a related counterpart application—International Search Report and Written Opinion, PCT/US2011/055923, Dec. 27, 2011, 12 pages.

Foreign communication from a related counterpart application—International Preliminary Report on Patentability, PCT/US2011/055923, Apr. 16, 2013, 8 pages.

Foreign communication from a related counterpart application—Invitation to Pay Additional Fees, PCT/US2013/035274, Jul. 31, 2013, 8 pages.

Foreign communication from a related counterpart application—International Search Report and Written Opinion, PCT/US2013/035274, Oct. 14, 2013, 19 pages.

Foreign communication from a related counterpart application—International Preliminary Report on Patentability, PCT/US2013/035274, Oct. 14, 2014, 14 pages.

Foreign communication from a related counterpart application—International Search Report and Written Opinion, PCT/US2013/035103, Jul. 31, 2013, 13 pages.

Foreign communication from a related counterpart application—International Preliminary Report on Patentability, PCT/US2013/035103, Oct. 14, 2014, 10 pages.

Jacobs, Marc L, et al., "Maximising membranes," Hydrocarbon Engineering, Jun. 2004, reprint, 3 pages.

Jacobs, Marc L, et al., "Monomer recover in polyolefin plants," Petrochemicals and Gas Processing, 4 pages.

Office Action dated Feb. 2, 2015, 42 pages, U.S. Appl. No. 13/446,965, filed Apr. 13, 2012.

Office Action (Final) dated May 21, 2015, 8 pages, U.S. Appl. No. 13/446,965, filed Apr. 13, 2012.

Office Action dated Jan. 22, 2015, 48 pages, U.S. Appl. No. 13/447,003, filed Apr. 13, 2012.

Notice of Allowance dated May 8, 2015, 12 pages, U.S. Appl. No. 13/447,003, filed Apr. 13, 2012.

Polyethylene (PE) Production, Marketing Brochure, MTR Membrane Technology & Research, 2009, 2 pages.

Reine, Travis A., et al., "Absorption Equilibrium and Kinetics for Ethylene-Ethane Separation with a Novel Solvent," Ind. Eng. Chem Res., 2005, vol. 44, pp. 7505-7510, American Chemical Society.

Filing receipt and specification for patent application entitled "Component Separations in Polymerization," by Scott E. Kufeld, et al., filed May 29, 2015 as U.S. Appl. No. 14/725,991.

Office Action dated Jun. 25, 2015 (33 pages), U.S. Appl. No. 14/725,991, filed May 29, 2015.

Notice of Allowance dated Jul. 13, 2015 (9 pages), U.S. Appl. No. 13/446,965, filed Apr. 13, 2012.

\* cited by examiner

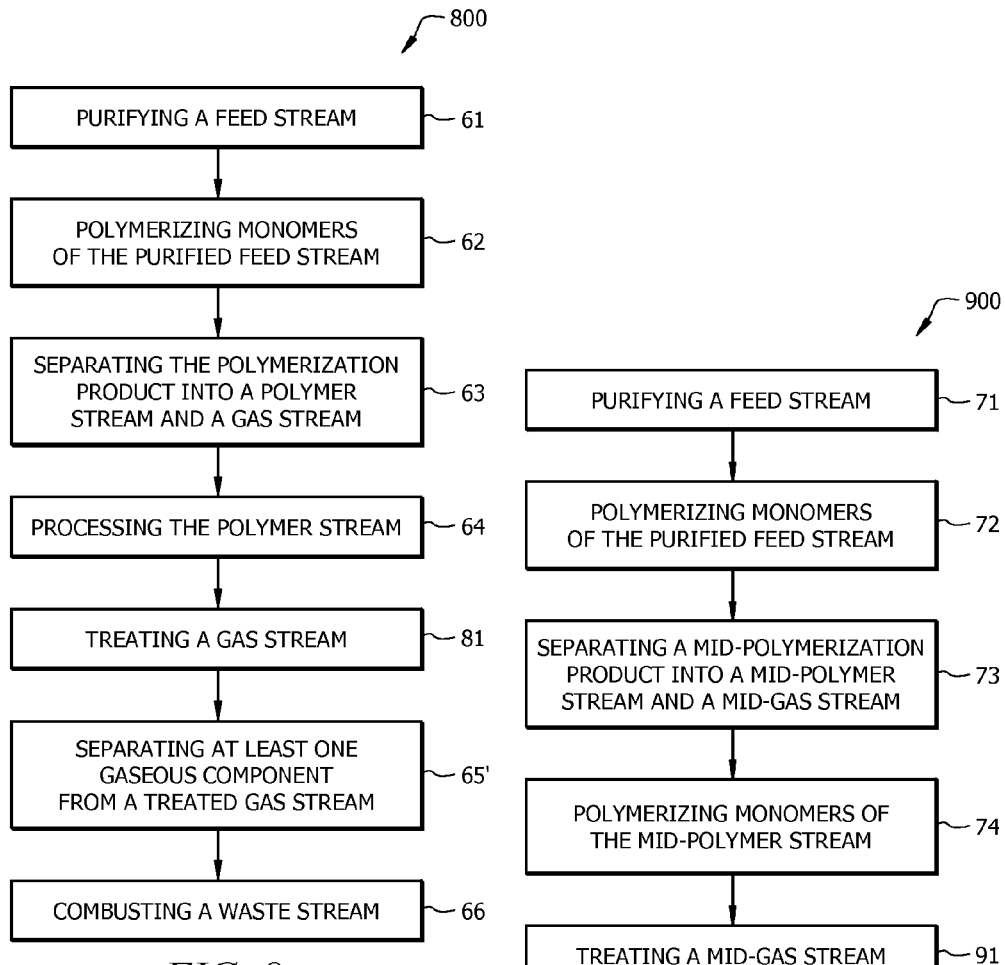

COMPONENT SEPARATIONS IN POLYMERIZATION

CROSS-REFERENCE TO RELATED APPLICATIONS

This application is a continuation of U.S. patent application Ser. No. 13/447,003 filed Apr. 13, 2012, published as U.S. Patent Application Publication No. US 2012/0232231 A1, and entitled "Component Separations in Polymerization," which is a continuation-in-part of U.S. patent application Ser. No. 12/905,966, filed Oct. 15, 2010, now U.S. Pat. No. 8,410,329 B2, and entitled "Improved Ethylene Separation," each of which is incorporated by reference in its entirety.

STATEMENT REGARDING FEDERALLY SPONSORED RESEARCH OR DEVELOPMENT

Not applicable.

BACKGROUND

1. Field of the Invention

This disclosure generally relates to the production of polyethylene. More specifically, this disclosure relates to systems and processes for improving polyethylene production efficiency by decreasing ethylene losses.

2. Background of the Invention

The production of polymers such as polyethylene from light gases requires a high purity feedstock of monomers and comonomers. Due to the small differences in boiling points between the light gases in such a feedstock, industrial production of a high purity feedstock may require the operation of multiple distillation columns, high pressures, and cryogenic temperatures. As such, the energy costs associated with feedstock purification represent a significant proportion of the total cost for the production of such polymers. Further, the infrastructure required for producing, maintaining, and recycling high purity feedstock is a significant portion of the associated capital cost.

In order to offset some of the costs and maximize production, it can be useful to reclaim and/or recycle any unreacted feedstock gases, especially the light hydrocarbon reactants, such as ethylene. Gases comprising unreacted monomers may be separated from the polymer after the polymerization reaction. The polymer is processed while the unreacted monomers are recovered from the gases that are reclaimed following the polymerization reaction. To accomplish this, the reclaimed gas streams have conventionally either been routed through a purification process or redirected through other redundant processing steps. In either case, conventional processes of recovering monomer have necessitated energetically unfavorable and expensive processes.

Consequently, there is a need for high-efficiency separation of ethylene from a recycle stream.

BRIEF SUMMARY

Disclosed herein is a process for component separation in a polymer production system, comprising separating a polymerization product stream into a gas stream and a polymer stream, wherein the gas stream comprises ethane and unreacted ethylene, distilling the gas stream into a light hydrocarbon stream, wherein the light hydrocarbon stream comprises ethane and unreacted ethylene, contacting the light hydrocarbon stream with an absorption solvent system, wherein at least a portion of the unreacted ethylene from the light hydrocarbon stream is absorbed by the absorption solvent system, and recovering a waste gas stream from the absorption solvent system, wherein the waste gas stream comprises ethane, hydrogen, or combinations thereof.

Also disclosed herein is a process for component separation in a polymer production system, comprising separating a polymerization product stream into a gas stream and a polymer stream, wherein the gas stream comprises ethane and unreacted ethylene, distilling the gas stream into an intermediate hydrocarbon stream and a first bottoms stream, wherein the intermediate hydrocarbon stream comprises ethane, ethylene, and isobutene, distilling the intermediate hydrocarbon stream into a light hydrocarbon stream and a second bottoms stream, wherein the light hydrocarbon stream comprises ethane and ethylene, contacting the light hydrocarbon stream with an absorption solvent system, wherein at least a portion of the unreacted ethylene from the light hydrocarbon stream is absorbed by the absorption solvent system, and recovering a waste gas stream from the absorption solvent system, wherein the waste gas stream comprises ethane, hydrogen, or combinations thereof.

Further disclosed herein is a process for component separation in a polymer production system, comprising polymerizing olefin monomers in a first polymerization reactor to yield a mid-polymerization product stream, separating the mid-polymerization product stream into a mid-gas stream and a mid-polymer stream, wherein the mid-gas stream comprises ethane, unreacted ethylene, and hydrogen, and polymerizing the mid-polymer stream in a second polymerization reactor.

Further disclosed herein is a process for component separation in a polymer production system, comprising polymerizing olefin monomers in a first polymerization reactor, separating a mid-polymerization product stream into a mid-gas stream and a mid-polymer stream, wherein the mid-gas stream comprises ethane and unreacted ethylene, polymerizing the mid-polymer stream in a second polymerization reactor, and introducing a scavenger prior to the second polymerization reactor.

Further disclosed herein is a process for component separation in a polymer production system, comprising polymerizing olefin monomers in a first polymerization reactor to yield a mid-polymerization product stream, degassing at least a portion of hydrogen from the mid-polymerization product stream to yield a hydrogen-reduced product stream, separating the hydrogen-reduced product stream into a mid-gas stream and a mid-polymer stream, wherein the mid-gas stream comprises ethane and unreacted ethylene, and polymerizing the mid-polymer stream in a second polymerization reactor.

The foregoing has outlined rather broadly the features and technical advantages of the disclosed inventive subject matter in order that the following detailed description may be better understood. The various characteristics described above, as well as other features, will be readily apparent to those skilled in the art upon reading the following detailed description of the preferred embodiments, and by referring to the accompanying drawings.

DESCRIPTION OF THE DRAWINGS

For a detailed description of the preferred embodiments of the disclosed processes and systems, reference will now be made to the accompanying drawings in which:

FIG. 8 illustrates a flow diagram of a third embodiment of a polyethylene production process;

FIG. 9 illustrates a flow diagram of a fourth embodiment of a polyethylene production process;

DETAILED DESCRIPTION

Disclosed herein are systems, apparatuses, and processes related to the production of polyethylene with improved efficiency. The systems, apparatuses, and processes are generally related to the separation of a first chemical component or compound from a composition resulting from the production of polyethylene and comprising the first chemical component or compound and one or more other chemical components, compounds, or the like.

Figure 1:
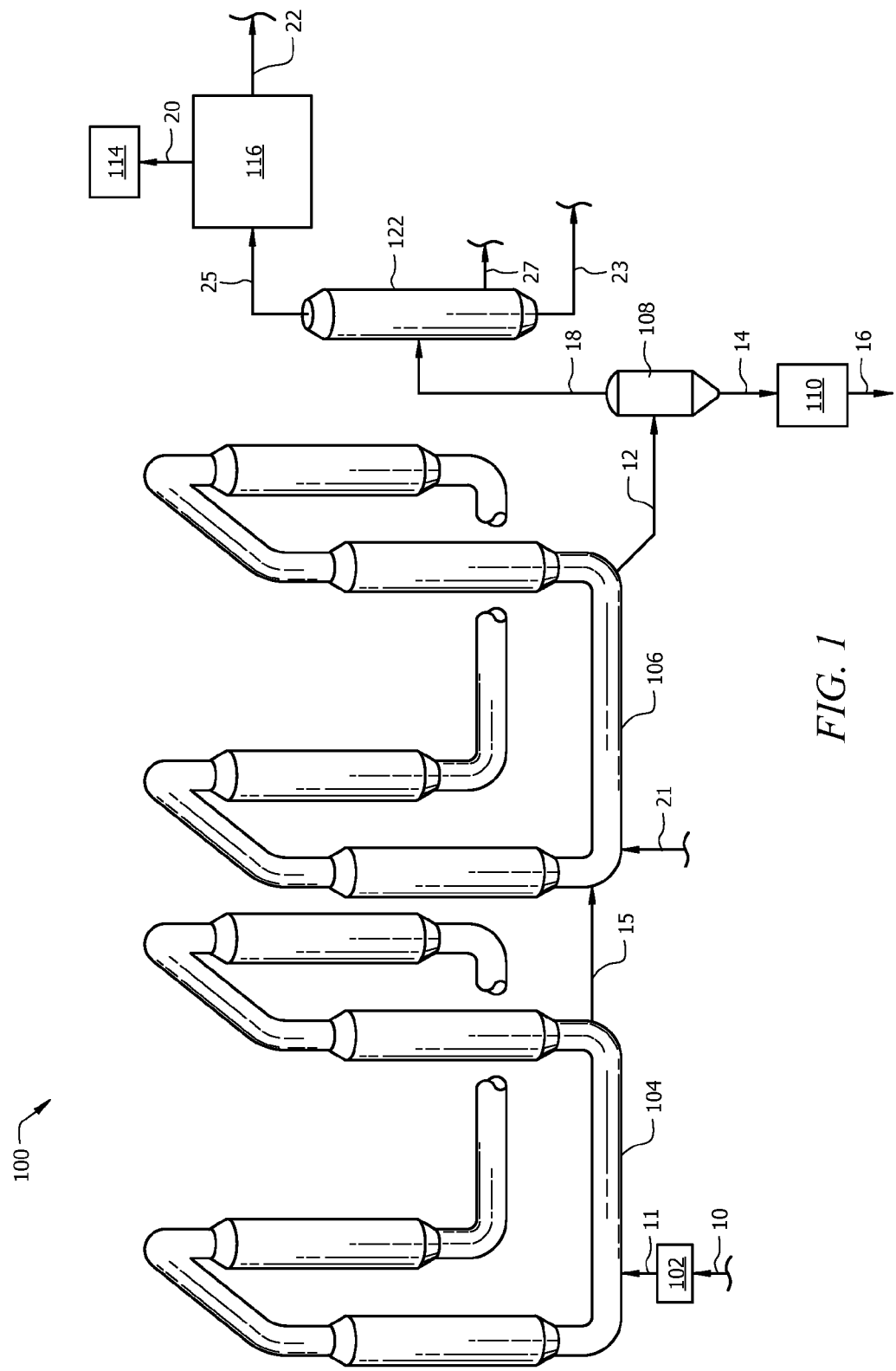
FIG. 1 illustrates a schematic of a first embodiment of a polyethylene production system.

Referring to FIG. 1, a first polyethylene production (PEP) system 100 is disclosed. PEP system 100 generally comprises a purifier 102, reactors 104, 106, a separator 108, a processor 110, a distillation column 122, an absorption reactor 116, and a processing device 114. In the PEP embodiments disclosed herein, various system components may be in fluid communication via one or more conduits (e.g., pipes, tubing, flow lines, etc.) suitable for the conveyance of a particular stream, for example as show in detail by the numbered streams in FIGS. 1-5, 10, 12-13.

In the embodiment of FIG. 1, a feed stream 10 may be communicated to the purifier 102. A purified feed stream 11 may be communicated from the purifier 102 to one or more of the reactors 104, 106. Where such a system comprises two or more reactors, a reactor stream 15 may be communicated from reactor 104 to reactor 106. Hydrogen may be introduced into reactor 106 in stream 21. A polymerization product stream 12 may be communicated from one or more of the reactors 104, 106 to the separator 108. A polymer stream 14 may be communicated from the separator 108 to the processor 110. A product stream 16 may be emitted from the processor 110. A gas stream 18 may be communicated from the separator 108 to the distillation column 122. A distillation bottoms stream 23 may be emitted from the distillation column 122, and a side stream 27 may be emitted from the distillation column 122. A light hydrocarbon stream 25 may be emitted from the distillation column 122 and communicated to the absorption reactor 116. A waste gas stream 20 may be communicated from the absorption reactor 116 to the processing device 114 and a recycle stream 22 may be communicated from the absorption reactor 116 to other locations in the system 100, for example, to the purifier 102 via the separator 108. In the case of recycle to the purifier 102 via the separator 108, recycle stream 22 may be communicated from the absorption reactor 116 to the separator 108, and a stream may be communicated from the separator 108 to the purifier 102.

Figure 2:
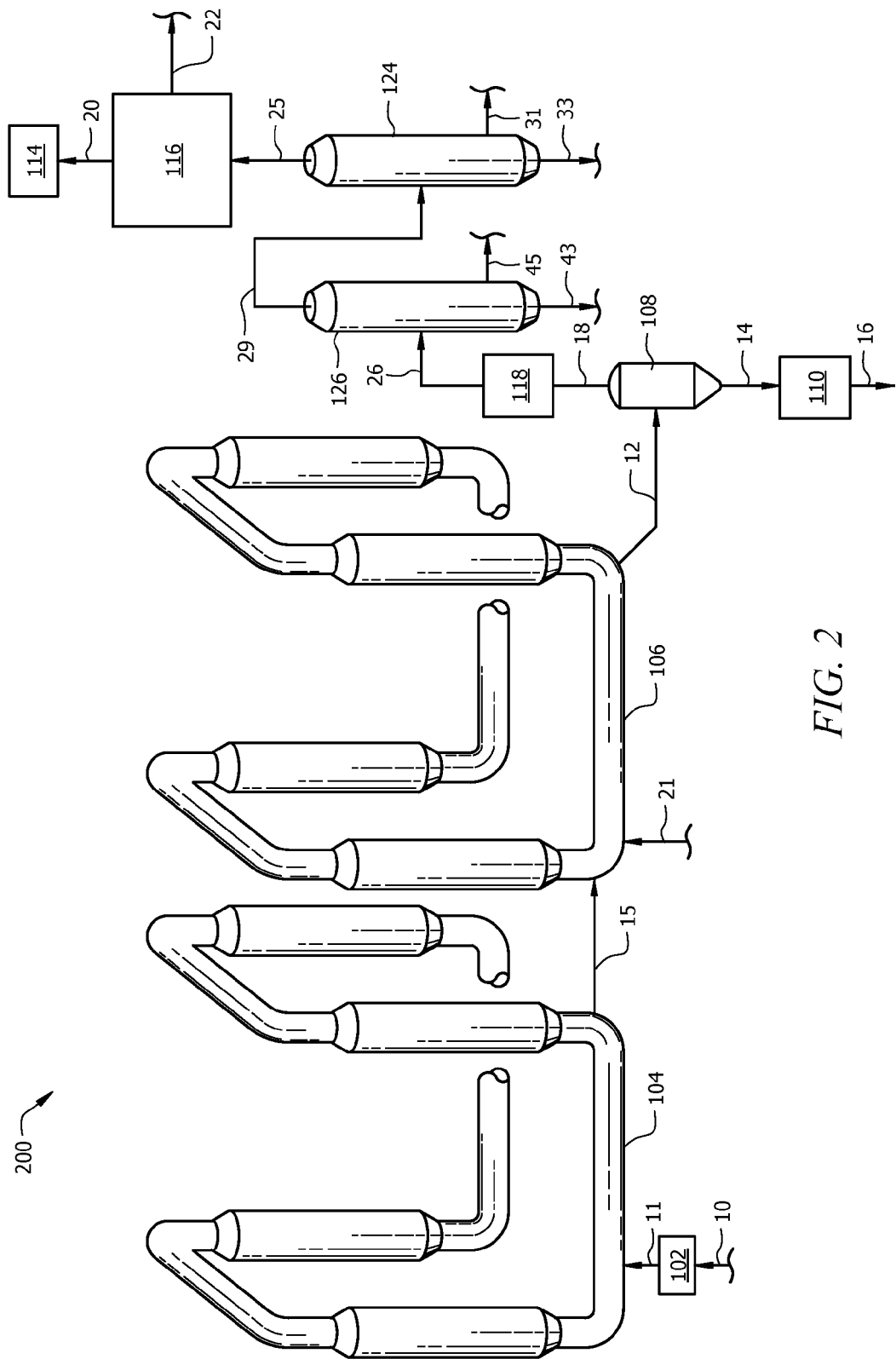
FIG. 2 illustrates a schematic of a second embodiment of a polyethylene production system.

Referring to FIG. 2, a second PEP system 200 is disclosed, which has a number of system components common with PEP 100. In the alternative embodiment illustrated by FIG. 2, the second PEP system 200 additionally comprises a deoxygenator 118. Alternatively to the first PEP system 100 (as illustrated in FIG. 1), in the embodiment illustrated by FIG. 2, the gas stream 18 may be communicated to the deoxygenator 118. A treated gas stream 26 may be communicated from the deoxygenator 118 to the distillation column 122. It is contemplated that embodiments of the inventive subject matter may operate with or without the deoxygenator 118 as may be suitable for gaseous components in gas stream 18.

In the alternative embodiment illustrated by FIG. 2, the second PEP system 200 additionally comprises a distillation column 124. In embodiments comprising distillation columns 122 and 124, distillation column 122 may be referred to as a first distillation column or a heavy distillation column, and distillation column 124 may be referred to as a second distillation column or a light distillation column. As shown in FIG. 2, treated gas stream 26 (and optionally, gas stream 18 for embodiments having no deoxygenator 118) may be communicated to distillation column 122. Intermediate hydrocarbon stream 29 may be communicated from distillation column 122 to distillation column 124. Distillation bottoms stream 23 may be emitted from distillation column 122. Distillation bottoms stream 33, and optionally, side stream 31 may be emitted from distillation column 124. Light hydrocarbon stream 25 may be emitted from distillation column 124 to the absorption reactor 116.

Figure 3:
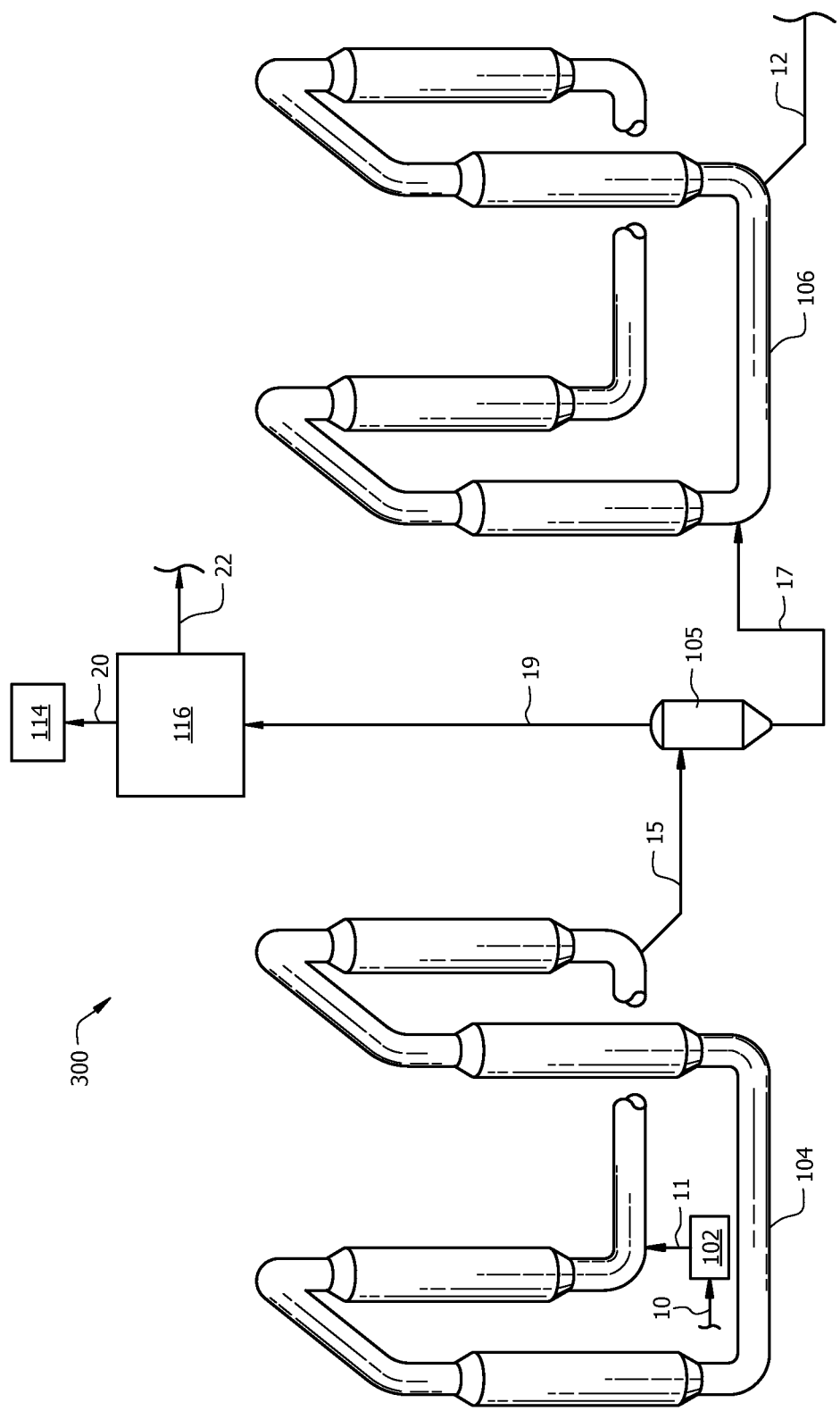
FIG. 3 illustrates a schematic of a third embodiment of a polyethylene production system.

Referring to FIG. 3, a third PEP system 300 is disclosed, which has a number of system components in common with PEP systems 100 and 200. System components downstream of polymerization product stream 12, such as those shown in FIGS. 1 and 2, are not included in FIG. 3; however, it is contemplated that embodiments such as system 300 may include such downstream components in the various embodiments disclosed. In the alternative embodiment illustrated by FIG. 3, the third PEP system 300 alternatively comprises a separator 105 between reactor 104 and reactor 106. A scavenger may be introduced into system via stream 35. Stream 35 may communicate with mid-polymerization product stream 15 to separator 105, where the mid-polymerization product stream 15 may be separated into mid-gas stream 19 and mid-polymer stream 17. Mid-polymer stream 17 may communicate to reactor 106, which emits polymerization product stream 12. Mid-gas stream 19 may be communicated to absorption reactor 116, which emits waste stream 20, absorbent stream 30, and recycle stream 22. The waste stream 20 may be communicated from the absorption reactor 116 to the processing device 114, and the recycle stream 22 may be communicated from the absorption reactor 116 to other locations in the system 300, as described for recycle stream 22 in FIG. 1.

Figure 4:
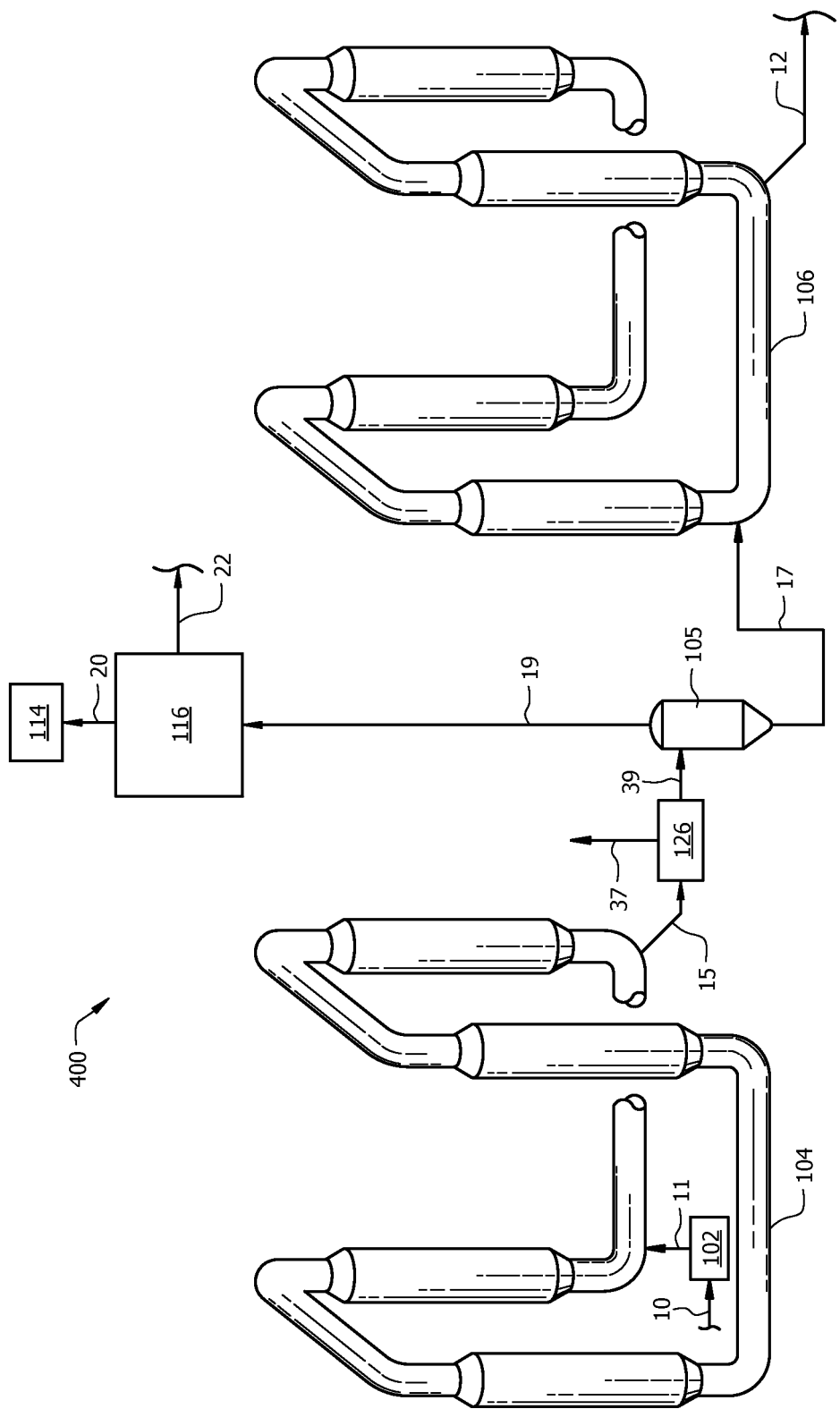
FIG. 4 illustrates a schematic of a fourth embodiment of a polyethylene production system.

Referring to FIG. 4, a fourth PEP system 400 is disclosed, which has a number of system components common with PEP system 300. System components downstream of polymerization product stream 12, such as those shown in FIGS. 1 and 2, are not included in FIG. 4; however, it is contemplated that embodiments such as system 400 may include such downstream components in the various embodiments disclosed. In the alternative embodiment illustrated in FIG. 4, the fourth PEP system 400 alternatively comprises separator 126. Reactor 104 may emit mid-polymerization product stream 15, which may be communicated to separator 126. Hydrogen stream 37 may be emitted from separator 126 and hydrogen-reduced product stream 39 may be communicated from separator 126 to separator 105.

Figure 5:
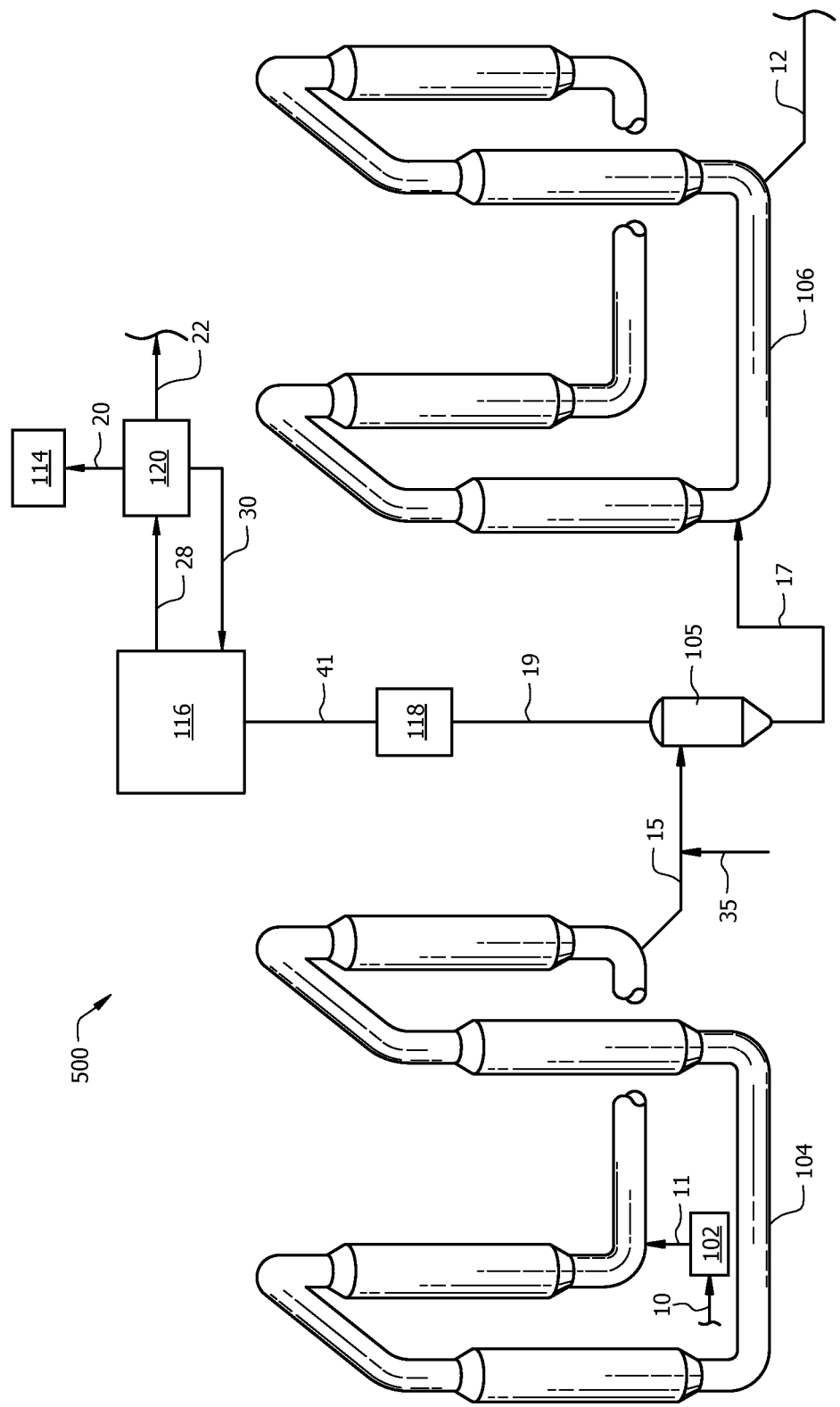
FIG. 5 illustrates a schematic of a fifth embodiment of a polyethylene production system.

Referring to FIG. 5, a fifth PEP system 500 is disclosed, which has a number of system components common with PEP systems 300 and 400. System components downstream of polymerization product stream 12, such as those shown in FIGS. 1 and 2, are not included in FIG. 5; however, it is contemplated that embodiments such as system 500 may include such downstream components in the various embodiments disclosed. In the alternative embodiment illustrated by FIG. 5, the fifth PEP system 500 additionally comprises a regenerator 120 (e.g., a desorption vessel). Alternatively to PEP systems 100, 200, 300, and 400, in the embodiment illustrated in FIG. 5, a complexed stream 28 may be communicated from the absorption reactor 116 to the regenerator 120. A recycle stream 22 may be communicated to other locations in the system 500, for example, to the purifier 102 via a separator (as discussed in FIG. 1). A regenerated absorbent stream 30 may be communicated from the regenerator 120 to the absorption reactor 116. Although the regenerator 120 is shown in FIG. 5 in conjunction with the absorption reactor 116, it is additionally contemplated that a regenerator may be used in conjunction with any of the absorption reactors 116 of the embodiments of FIGS. 1 through 4. Additionally, it is contemplated the absorption reactor 116 of FIG. 5 may be configured to operate without regenerator 120.

A temperature of lean solvent may be taken from stream 30 in FIG. 5. The temperature of the absorption reactor 116 may depend on a temperature of gas stream 18, a temperature of lean solvent in stream 30, a heat of solution, and a heat of reaction. In the disclosed embodiments, the mass flow rate of lean solvent in stream 30 may be 50 to 300 times greater than a mass flow rate of the gas stream 18. Therefore, the temperature of the absorption reactor 116 may highly depend on the temperature of lean solvent in the disclosed embodiments.

Various embodiments of suitable PEP systems having been disclosed, embodiments of a PEP process are now disclosed. One or more of the embodiments of a PEP process may be described with reference to one or more of PEP system 100, PEP system 200, PEP system 300, PEP system 400, and/or PEP system 500. Although a given PEP process may be described with reference to one or more embodiments of a PEP system, such a disclosure should not be construed as so-limiting. Although the various steps of the processes disclosed herein may be disclosed or illustrated in a particular order, such should not be construed as limiting the performance of these processes to any particular order unless otherwise indicated.

Figure 6:
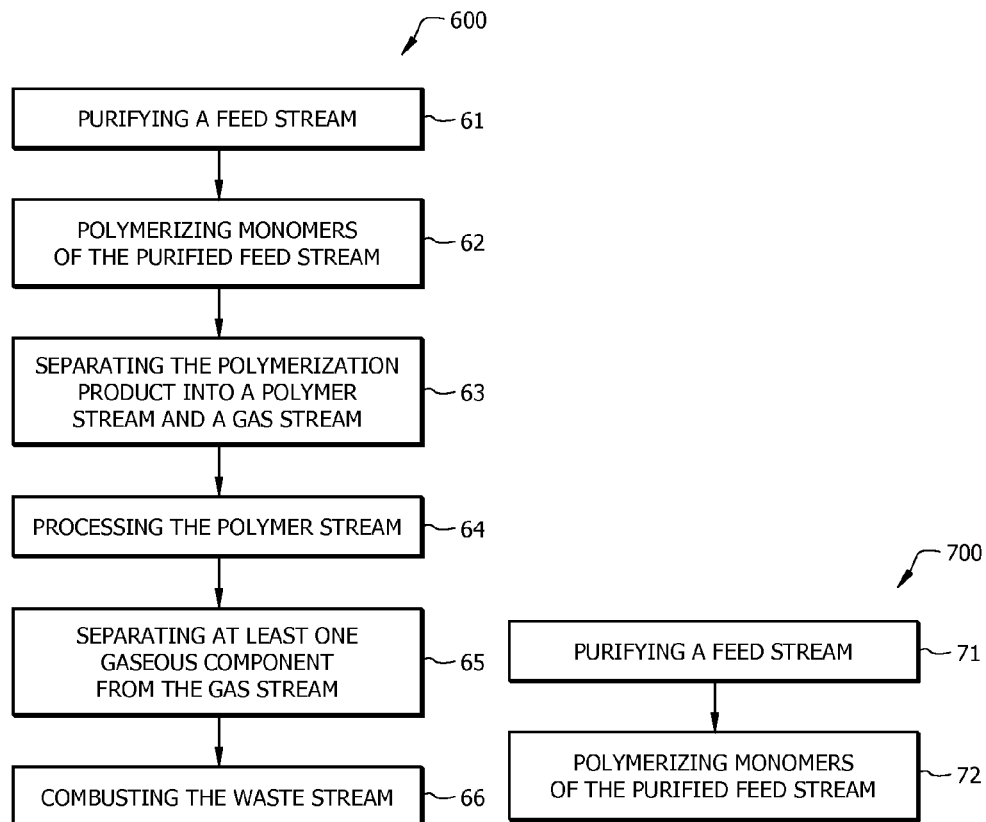
FIG. 6 illustrates a flow diagram of a first embodiment of a polyethylene production process.

Referring to FIG. 6, a first PEP process 600 is illustrated. PEP process 600 generally comprises at block 61 purifying a feed stream, at block 62 polymerizing monomers of the purified feed stream to form a polymerization product, at block 63 separating the polymerization product into a polymer stream and a gas stream, at block 64 processing the polymer stream, at block 65 separating at least one gaseous component from the gas stream to form a recycle stream and a waste stream, and at block 66 combusting the waste stream.

As an example, the first PEP process 600 or a portion thereof may be implemented via the first PEP system 100 (e.g., as illustrated in FIG. 1). Referring to FIGS. 1 and 6, in an embodiment the feed stream 10 may comprise a gaseous reactant, particularly, ethylene. In an embodiment, purifying the feed stream may yield a purified stream 11 comprising substantially pure monomers (e.g., ethylene monomers), comonomers (e.g., butene-1 comonomers, or combinations thereof. Polymerizing monomers (optionally, comonomers) of the purified stream 11 may yield the polymerization product stream 12 generally comprising unreacted monomer (e.g., ethylene), optional unreacted comonomer (e.g., butene-1), by-products (e.g., ethane, which may be by-product ethane formed from ethylene and hydrogen), and a polymerization product (e.g., polymer and optionally, copolymer). Separating the polymerization product stream 12 may yield the polymer stream 14 (e.g., polyethylene polymer, copolymer) and the gas stream 18 generally comprising unreacted monomer (e.g., ethylene monomer and any optional comonomer such as butene-1) and various gases (e.g., ethane, hydrogen). Processing the polymer stream 14 may yield the product stream 16. Separating at least one gaseous component from the gas stream 18 may yield a recycle stream 22, generally comprising unreacted ethylene monomer (optionally, unreacted comonomer), and a waste gas stream 20. In an embodiment, separating at least one gaseous component from the gas stream 18 may comprise distilling ethylene from the gas stream 18 to yield a light hydrocarbon stream 25. In an embodiment, separating the gas stream 18 may alternatively or additionally comprise absorbing ethylene from the gas stream 18 to yield the waste gas stream 20 and then liberating the absorbed ethylene to form the recycle stream 22. The recycle stream 22, comprising ethylene, may be pressurized (e.g., returned to the purifier 102 via the separator 108 for pressurization) and re-introduced into a PEP process (e.g., PEP process 600). Combusting the waste gas stream 20 may be carried out with a flare as the processing device 114.

Figure 7:
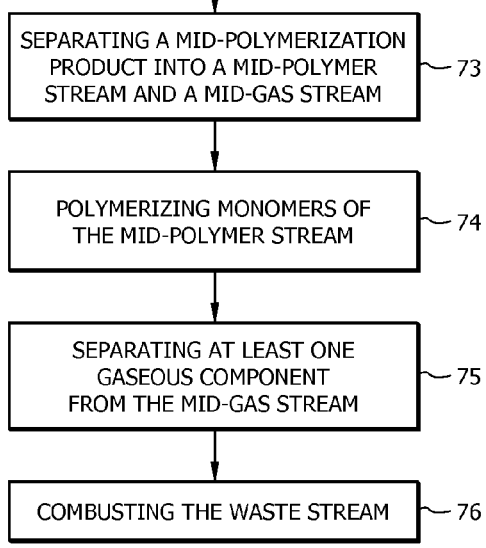
FIG. 7 illustrates a flow diagram of a second embodiment of a polyethylene production process.

Referring to FIG. 7, a second PEP process 700 is illustrated, which has a number of process steps common with PEP process 600. PEP process 700 generally comprises at block 71 purifying a feed stream, at block 72 polymerizing monomers of the purified feed stream to form a mid-polymerization product, at block 73 separating the polymerization product into a mid-polymer stream and a mid-gas stream, at block 74 polymerizing monomers (optionally, comonomers) of the mid-polymer stream, at block 75 separating at least one gaseous component from the mid-gas stream to form a recycle stream and a waste stream, and at block 76 combusting the waste stream. In the alternative embodiment illustrated by FIG. 7, blocks 63-64 of FIG. 6 are replaced by blocks 73-75. Generally, the process 700 of FIG. 7 takes place between reactors 104 and 106, whereas the process 600 of FIG. 6 takes place downstream of reactors 104 and 106.

As an example, the second PEP process 700 or a portion thereof may be implemented via the third PEP system 300 (e.g., as illustrated in FIG. 3). Referring to FIGS. 3 and 7, in an embodiment the feed stream 10 may comprise a gaseous reactant, particularly, ethylene. In an embodiment, purifying the feed stream may yield a purified stream 11 comprising substantially pure monomers (e.g., ethylene monomers) and optionally, comonomers (e.g., butene-1). Polymerizing monomers of the purified stream 11 may yield the mid-polymerization product stream 15 generally comprising unreacted monomer (e.g., ethylene), optional unreacted comonomer (e.g., butene-1), by-products (e.g., ethane, which may be by-product ethane formed from ethylene and hydrogen), and a polymerization product (e.g., polymer and optionally, copolymer). In alternative to the polymerization product stream 12 of FIG. 1, which is downstream of polymerization reactors 104 and 106, mid-polymerization product stream 15 of the embodiment in FIG. 3 may be between polymerization reactor(s) 104 and polymerization reactor(s) 106. Separating the mid-polymerization product stream 15 may yield the mid-polymer stream 17 generally comprising unreacted ethylene, ethane (which may be by-product ethane formed from ethylene and hydrogen) and a polymer (e.g., polyethylene), and the mid-gas stream 19 generally comprising unreacted monomer (e.g., ethylene monomer), optionally, unreacted comonomer (e.g., butene-1 monomer), and various gases (e.g., ethane, hydrogen). Polymerizing monomers (optionally, comonomers) of the mid-polymer stream 17 may yield polymerization product stream 12. Components of polymerization product stream 12 may be processed according to embodiments of systems 100 and 200 in FIGS. 1 and 2. Separating at least one gaseous component from the mid-gas stream 19 may yield a recycle stream 22, generally comprising unreacted ethylene monomer (optionally, comonomer), and a waste gas stream 20. In an embodiment, separating the at least one gaseous component from mid-gas stream 19 may comprise absorbing ethylene from the mid-gas stream 19 to yield the waste gas stream 20 and then liberating the absorbed ethylene to form the recycle stream 22. The recycle stream 22, comprising ethylene, may be pressurized and re-introduced (e.g., as described in FIG. 1) into a PEP process (e.g., PEP process 700). Combusting the waste gas stream 20 may be carried out with a flare as the processing device 114.

Referring to FIG. 8, a third PEP process 800 is illustrated, which has a number of process steps common with PEP process 600 (i.e., blocks 61, 62, 63, 64, 65, and 66). In the alternative embodiment illustrated by FIG. 8, the PEP process 800 includes block 81 treating a gas stream to form a treated gas stream and at block 65' separating at least one gaseous component from the treated gas stream to form a recycle stream and a waste stream.

In an embodiment, third PEP process 800 or a portion thereof may be implemented via the second PEP system 200 (e.g. as illustrated in FIG. 2). Alternatively to the embodiments of FIGS. 1 and 6, in the embodiment of FIGS. 2 and 8, treating the gas stream 18 may yield the treated gas stream 26. In an embodiment, treating the gas stream 18 comprises deoxygenating the gas stream 18. Separating at least one gaseous component from the treated gas stream 26 may yield a recycle stream 22, generally comprising unreacted ethylene monomer (optionally, comonomer), a waste gas stream 20, a distillation bottoms stream 23, a distillation bottoms stream 33, and a side stream 31.

Referring to FIG. 9, a fourth PEP process 900 is illustrated, which has a number of process steps common with PEP process 700. In the alternative embodiment illustrated by FIG. 9, the PEP process 900 includes block 91 treating a gas stream (e.g., the mid-gas stream 19) to form a treated gas stream. Block 75 of FIG. 7 is altered at block 75' for separating at least one gaseous component from the treated gas stream to form a complexed stream and a waste gas stream. At block 92, PEP process 900 includes separating the complexed stream into an absorbent stream and a recycle stream.

In an embodiment, fourth PEP process 900 or a portion thereof may be implemented via the fifth PEP system 500 (e.g. as illustrated in FIG. 5). Alternatively to the embodiments of FIGS. 3 & 7, in the embodiments of FIGS. 5 & 9, separating at least one gaseous component from the treated gas stream 41 may yield an unreacted monomer-absorbent (e.g., an ethylene-absorbent) in complexed stream 28. In an embodiment, separating the unreacted monomer-absorbent complexed stream 28 comprises liberating the absorbed ethylene to form a recycle stream 22 and an absorbent stream 30. In the embodiment of FIGS. 5 and 9, separating at least one gaseous component from the treated gas stream 26 may yield an unreacted comonomer-absorbent (e.g., a butene-1-absorbent) in complexed stream 28. In an embodiment, separating the unreacted comonomer-absorbent in complexed stream 28 comprises releasing the absorbed comonomer to form a recycle stream 22 and a regenerated absorbent stream 30.

In one or more of the embodiments disclosed herein, purifying a feed stream (e.g., at block 61 or 71) may comprise separating unwanted compounds and elements from a feed stream comprising ethylene to form a purified feed stream. In an embodiment, the feed stream may comprise ethylene and various other gases, such as but not limited to methane, ethane, acetylene, propylene, various other hydrocarbons having three or more carbon atoms, or combinations thereof. In an embodiment, purifying a feed stream may comprise any suitable method or process, including the non-limiting examples filtering, membrane screening, reacting with various chemicals, absorbing, adsorbing, distillation(s), or combinations thereof.

In embodiments as illustrated by FIGS. 1-5, purifying a feed stream may comprise routing the feed stream 10 to the purifier 102. In one or more of the embodiments disclosed herein, the purifier 102 may comprise a device or apparatus suitable for the purification of one or more reactant gases in a feed stream comprising a plurality of potentially unwanted gaseous compounds, elements, contaminants, or the like. Non-limiting examples of a suitable purifier 102 may comprise a filter, a membrane, a reactor, an absorbent, a molecular sieve, one or more distillation columns, or combinations thereof. The purifier 102 may be configured to separate ethylene from a stream comprising methane, ethane, acetylene, propane, propylene, water, oxygen various other gaseous hydrocarbons, various contaminants, and/or combinations thereof.

In an embodiment, purifying a feed stream may yield a purified feed 11 comprising substantially pure ethylene. In an embodiment, the purified feed stream may comprise less than 25% by total weight of the stream, alternatively, less than about 10%, alternatively, less than about 1.0% of any one or more of nitrogen, oxygen, methane, ethane, propane, or combinations thereof. As used herein "substantially pure ethylene" refers to a fluid stream comprising at least about 60% ethylene, alternatively, at least about 70% ethylene, alternatively, at least about 80% ethylene, alternatively, at least about 90% ethylene, alternatively, at least about 95% ethylene, alternatively, at least about 99% ethylene by total weight of the stream, alternatively, at least about 99.5% ethylene by total weight of the stream. In an embodiment, the feed stream 11 may further comprise trace amounts of ethane, for example, as from a recycle stream as will be discussed.

In one or more of the embodiments disclosed herein, monomers in feed stream 11, mid-polymerization product stream 15, and mid-polymer stream 17 may be polymerized. In one or more embodiments, polymerizing monomers of the purified feed (e.g., at blocks 62 and 72) may comprise allowing a polymerization reaction between a plurality of monomers by contacting a monomer or monomers with a catalyst system under conditions suitable for the formation of a polymer. In one or more of the embodiments disclosed herein, polymerizing comonomers (e.g., at blocks 62 and 72) of the purified feed may comprise allowing a polymerization reaction between a plurality of comonomers by contacting a comonomer or comonomers with a catalyst system under conditions suitable for the formation of a copolymer. Likewise, in one or more of the embodiments disclosed herein, polymerizing monomers of the mid-polymer stream (e.g., at block 74) may comprise allowing a polymerization reaction between a plurality of monomers by contacting a monomer or monomers with a catalyst system under conditions suitable for the formation of a polymer. In one or more of the embodiments disclosed herein, polymerizing comonomers (e.g., at block 74) of the mid-polymer stream may comprise allowing a polymerization reaction between a plurality of comonomers by contacting a comonomer or comonomers with a catalyst system under conditions suitable for the formation of a copolymer. Likewise still, in one or more of the embodiments disclosed herein, polymerizing monomers of the mid-polymerization product may comprise allowing a polymerization reaction between a plurality of monomers by contacting a monomer or monomers with a catalyst system under conditions suitable for the formation of a polymer. In one or more of the embodiments disclosed herein, polymerizing comonomers of the mid-polymerization product may comprise allowing a polymerization reaction between a plurality of comonomers by contacting a comonomer or comonomers with a catalyst system under conditions suitable for the formation of a copolymer.

In embodiments as illustrated by FIGS. 1-5, polymerizing monomers of the purified feed may comprise routing the feed stream 11 to the one or more of the polymerization reactors or "reactors" 104, 106. In embodiments as illustrated by FIGS. 1-2, polymerizing monomers of the mid-polymerization product may comprise routing the mid-polymerization product stream 15 to polymerization reactor(s) 106. In embodiments as illustrated by FIGS. 1-2, polymerizing monomers of the mid-polymerization product may comprise routing the mid-polymerization product stream 15 from polymerization reactor(s) 104 to polymerization reactor(s) 106. In embodiments as illustrated by FIGS. 3-5, polymerizing monomers of the mid-polymer stream 17 may comprise routing the mid-polymer stream 17 to polymerization reactor(s) 106. In embodiments as illustrated by FIGS. 3-5, polymerizing monomers of the mid-polymer stream 17 may comprise routing the mid-polymer stream 17 from a separator 105 to polymerization reactor(s) 106.

In an embodiment, any suitable catalyst system may be employed. A suitable catalyst system may comprise a catalyst and, optionally, a co-catalyst and/or promoter. Non-limiting examples of suitable catalyst systems include Ziegler Natta catalysts, Ziegler catalysts, chromium catalysts, chromium oxide catalysts, chromocene catalysts, metallocene catalysts, nickel catalysts, or combinations thereof. Catalyst systems suitable for use in this disclosure have been described, for example, in U.S. Pat. No. 7,619,047 and U.S. Patent Application Publication Nos. 2007/0197374, 2009/0004417, 2010/0029872, 2006/0094590, and 2010/0041842, each of which is incorporated by reference herein in its entirety.

In one or more of the embodiments disclosed herein, the reactors 104, 106 may comprise any vessel or combination of vessels suitably configured to provide an environment for a chemical reaction (e.g., a contact zone) between monomers (e.g., ethylene) and/or polymers (e.g., an "active" or growing polymer chain), and optionally comonomers (e.g., butene-1) and/or copolymers, in the presence of a catalyst to yield a polymer (e.g., a polyethylene polymer) and/or copolymer. Although the embodiments illustrated in FIGS. 1, 2, and 3, illustrate various PEP systems having two reactors in series, one of skill in the art viewing this disclosure will recognize that one reactor, alternatively, any suitable number and/or configuration of reactors, may be employed.

As used herein, the terms "polymerization reactor" or "reactor" include any polymerization reactor capable of polymerizing olefin monomers or comonomers to produce homopolymers or copolymers. Such homopolymers and copolymers are referred to as resins or polymers. The various types of reactors include those that may be referred to as batch, slurry, gas-phase, solution, high pressure, tubular or autoclave reactors. Gas phase reactors may comprise fluidized bed reactors or staged horizontal reactors. Slurry reactors may comprise vertical or horizontal loops. High pressure reactors may comprise autoclave or tubular reactors. Reactor types can include batch or continuous processes. Continuous processes could use intermittent or continuous product discharge. Processes may also include partial or full direct recycle of unreacted monomer, unreacted comonomer, and/or diluent.

Polymerization reactor systems of the present disclosure may comprise one type of reactor in a system or multiple reactors of the same or different type. Production of polymers in multiple reactors may include several stages in at least two separate polymerization reactors interconnected by transfer stream(s), line(s), apparatus(es) (for example, a separation vessel(s)) and/or device(s) (for example, a valve or other mechanism) making it possible to transfer the polymers resulting from the first polymerization reactor (e.g., reactor 104) into the second reactor (e.g., reactor 106). The desired polymerization conditions in one of the reactors may be different from the operating conditions of the other reactors. Alternatively, polymerization in multiple reactors may include the manual transfer of polymer from one reactor to subsequent reactors for continued polymerization. Multiple reactor systems may include any combination including, but not limited to, multiple loop reactors, multiple gas reactors, a combination of loop and gas reactors, multiple high pressure reactors or a combination of high pressure with loop and/or gas reactors. The multiple reactors may be operated in series or in parallel.

In embodiments as illustrated in FIGS. 1-5, production of polymers in multiple reactors may include at least two polymerization reactors 104, 106 interconnected by one or more devices or apparatus (e.g., valve, continuous take-off valve, and/or continuous take-off mechanism). In embodiments as illustrated in FIGS. 1-2, production of polymers in multiple reactors may include at least two polymerization reactors 104, 106 interconnected by one or more streams or lines (e.g., mid-polymerization product stream 15). In embodiments as illustrated in FIGS. 3-5, production of polymers in multiple reactors may include at least two polymerization reactors 104, 106 interconnected by one or more separator (e.g., separator 105 and/or separator 126) via two or more streams (e.g., mid-polymerization product stream 15 and mid-polymer stream 17).

According to one aspect, the polymerization reactor system may comprise at least one loop slurry reactor comprising vertical or horizontal loops. Monomer, diluent, catalyst, and optionally any comonomer may be continuously fed to a loop reactor where polymerization occurs. Generally, continuous processes may comprise the continuous introduction of a monomer, an optional comonomer, a catalyst, and a diluent into a polymerization reactor and the continuous removal from this reactor of a suspension comprising polymer particles and the diluent. Reactor effluent may be flashed to remove the solid polymer from the liquids that comprise the diluent, monomer and/or comonomer. Various technologies may be used for this separation step including but not limited to, flashing that may include any combination of heat addition and pressure reduction; separation by cyclonic action in either a cyclone or hydrocyclone; or separation by centrifugation.

In one or more embodiments, a comonomer may comprise unsaturated hydrocarbons having 3 to 12 carbon atoms. For example, a comonomer may comprise propene, butene-1, hexene-1, octenes, or combinations thereof.

A typical slurry polymerization process (also known as the particle form process), is disclosed, for example, in U.S. Pat. Nos. 3,248,179, 4,501,885, 5,565,175, 5,575,979, 6,239,235, 6,262,191 and 6,833,415, each of which is incorporated by reference in its entirety herein.

In one or more embodiments, suitable diluents used in slurry polymerization include, but are not limited to, the monomer, and optionally, the comonomer, being polymerized and hydrocarbons that are liquids under reaction conditions. Examples of suitable monomer diluents include, but are not limited to, hydrocarbons such as propane, cyclohexane, isobutane, n-butane, n-pentane, isopentane, neopentane, and n-hexane. In embodiments, comonomer diluents may comprise unsaturated hydrocarbons having 3 to 12 carbon atoms. Examples of suitable comonomer diluents include, but are not limited to propene, butene-1, hexene-1, octenes, or combinations thereof. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another aspect, the polymerization reactor may comprise at least one gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Likewise, copolymer product may optionally be withdrawn from the reactor and new or fresh comonomer may be added to replace polymerized comonomer, polymerized monomer, or combinations thereof. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4,588,790 and 5,436,304, each of which is incorporated by reference in its entirety herein.

According to still another aspect, a high pressure polymerization reactor may comprise a tubular reactor or an autoclave reactor. Tubular reactors may have several zones where fresh monomer (optionally, comonomer), initiators, or catalysts may be added. Monomer (optionally, comonomer) may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

According to yet another aspect, the polymerization reactor may comprise a solution polymerization reactor wherein the monomer (optionally, comonomer) may be contacted with the catalyst composition by suitable stirring or other means. A carrier comprising an inert organic diluent or excess monomer (optionally, comonomer) may be employed. If desired, the monomer and/or optional comonomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed to obtain better temperature control and to maintain uniform polymerization mixtures throughout the polymerization zone. Adequate means are utilized for dissipating the exothermic heat of polymerization.

Polymerization reactors suitable for the disclosed systems and processes may further comprise any combination of at least one raw material feed system, at least one feed system for catalyst or catalyst components, and/or at least one polymer recovery system. Suitable reactor systems may further comprise systems for feedstock purification, catalyst storage and preparation, extrusion, reactor cooling, polymer recovery, fractionation, recycle, storage, loadout, laboratory analysis, and process control.

Conditions that are controlled for polymerization efficiency and to provide resin properties include temperature, pressure and the concentrations of various reactants. Polymerization temperature can affect catalyst productivity, polymer molecular weight and molecular weight distribution. Suitable polymerization temperature may be any temperature below the de-polymerization temperature according to the Gibbs Free energy equation. Typically this includes from about 60° C. to about 280° C., for example, and from about 70° C. to about 110° C., depending upon the type of polymerization reactor.

Suitable pressures will also vary according to the reactor and polymerization type. The pressure for liquid phase polymerizations in a loop reactor is typically less than 1000 psig. Pressure for gas phase polymerization is usually at about 200-500 psig. High pressure polymerization in tubular or autoclave reactors is generally run at about 20,000 to 75,000 psig. Polymerization reactors can also be operated in a supercritical region occurring at generally higher temperatures and pressures. Operation above the critical point of a pressure/temperature diagram (supercritical phase) may offer advantages. In an embodiment, polymerization may occur in an environment having a suitable combination of temperature and pressure. For example, polymerization may occur at a pressure in a range from about 550 psi to about 650 psi, alternatively, about 600 psi to about 625 psi and a temperature in a range from about 170° F. to about 230° F., alternatively, from about 195° F. to about 220° F.

The concentration of various reactants can be controlled to produce resins with certain physical and mechanical properties. The proposed end-use product that will be formed by the resin and the method of forming that product determines the desired resin properties. Mechanical properties include tensile, flexural, impact, creep, stress relaxation and hardness tests. Physical properties include density, molecular weight, molecular weight distribution, melting temperature, glass transition temperature, temperature melt of crystallization, density, stereoregularity, crack growth, long chain branching and rheological measurements.

The concentrations and/or partial pressures of monomer, comonomer, hydrogen, co-catalyst, modifiers, and electron donors are important in producing these resin properties. Comonomer may be used to control product density. Hydrogen may be used to control product molecular weight. Cocatalysts can be used to alkylate, scavenge poisons and control molecular weight. Modifiers can be used to control product properties and electron donors affect stereoregularity, the molecular weight distribution, or molecular weight. In addition, the concentration of poisons is minimized because poisons impact the reactions and product properties.

In an embodiment, polymerizing monomers may comprise introducing a suitable catalyst system into the first and/or second reactor 104, 106, respectively, so as to form a slurry. Alternatively, a suitable catalyst system may reside in the first and/or second reactor 104, 106, respectively.

As explained above, polymerizing monomers may comprise selectively manipulating one or more polymerization reaction conditions to yield a given polymer product, to yield a polymer product having one or more desirable properties, to achieve a desired efficiency, to achieve a desired yield, the like, or combinations thereof. Non-limiting examples of such parameters include temperature, pressure, type and/or quantity of catalyst or cocatalyst, and the concentrations and/or partial pressures of various reactants. In an embodiment, polymerizing monomers of the purified feed 52 may comprise adjusting one or more polymerization reaction conditions. In an embodiment, polymerizing monomers may comprise adding ethylene monomer and/or a comonomer such as butene to the polymerization reactor 106.

In an embodiment, polymerizing monomers may comprise maintaining a suitable temperature, pressure, and/or partial pressure(s) during the polymerization reaction, alternatively, cycling between a series of suitable temperatures, pressures, and/or partials pressure(s) during the polymerization reaction.

In an embodiment, polymerizing monomers may include introducing hydrogen into one or more of reactors 104 and 106. For example, FIGS. 1 and 2 illustrate hydrogen may be introduced into reactor 106 through stream 21. The amount of hydrogen introduced into the reactor 106 may be adjusted so as to obtain, in the diluent, a molar ratio of hydrogen to ethylene of 0.001 to 0.1. This molar ratio may be at least 0.004 in reactor 106. In embodiments, this molar ratio may not exceed 0.05. The ratio of the concentration of hydrogen in the diluent in reactor 104 to the concentration of hydrogen polymerization reactor 106 may be at least 20, alternatively, at least 30, alternatively, at least 40, alternatively, not greater than 300, alternatively, not greater than 200. Suitable hydrogen concentration control methods and systems are disclosed in U.S. Pat. No. 6,225,421, which is incorporated herein by reference.

In an embodiment, polymerizing monomers may comprise circulating, flowing, cycling, mixing, agitating, or combinations thereof, the monomers (optionally, comonomers), catalyst system, and/or the slurry within and/or between the reactors 104, 106. In an embodiment where the monomers (optionally, comonomers), catalyst system, and/or slurry are circulated, circulation may be at a velocity (e.g., slurry velocity) of from about 1 m/s to about 30 m/s, alternatively, from about 2 m/s to about 17 m/s, alternatively, from about 3 m/s to about 15 m/s.

In an embodiment, polymerizing monomers may comprise configuring reactors 104, 106 to yield a multimodal (e.g., a bimodal) polymer (e.g., polyethylene). For example, the resultant polymer may comprise both a relatively high molecular weight, low density (HMWLD) polyethylene polymer and a relatively low molecular weight, high density (LMWHD) polyethylene polymer. For example, various types of suitable polymers may be characterized as having a various densities. For example, a Type I may be characterized as having a density in a range of from about 0.910 g/cm$^3$ to about 0.925 g/cm$^3$, alternatively, a Type II may be characterized as having a density from about 0.926 g/cm$^3$ to about 0.940 g/cm$^3$, alternatively, a Type III may be characterized as having a density from about 0.941 g/cm$^3$ to about 0.959 g/cm$^3$, alternatively, a Type IV may be characterized as having a density of greater than about 0.960 g/cm$^3$.

In an embodiment, polymerizing monomers may comprise polymerizing comonomers in one or more of polymerization reactors 104, 106.

In the embodiments illustrated in FIGS. 1-5, polymerizing monomers of the purified feed may yield mid-polymerization product stream 15 and/or polymerization product stream 12. Such a mid-polymerization product stream 15 and/or a polymerization product stream 12 may generally comprise various solids, semi-solids, volatile and nonvolatile liquids, gases and combinations thereof. In an embodiment, the mid-polymerization product stream 15 and/or the polymerization product stream 12 may comprise hydrogen, nitrogen, methane, ethylene, ethane, propylene, propane, butane, isobutane, pentane, hexane, hexene-1 and heavier hydrocarbons. In an embodiment, ethylene may be present in a range of from about 0.1% to about 15%, alternatively, from about 1.5% to about 5%, alternatively, about 2% to about 4% by total weight of the stream. Ethane may be present in a range of from about 0.001% to about 4%, alternatively, from about 0.2% to about 0.5% by total weight of the stream. Isobutane may be present in a range from about 80% to about 98%, alternatively, from about 92% to about 96%, alternatively, about 95% by total weight of the stream.

The solids and/or liquids may comprise a polymer product (e.g., a polyethylene polymer), often referred to at this stage of the PEP process as "polymer fluff." The gases may comprise unreacted, gaseous reactant monomers or optional comonomers (e.g., unreacted ethylene monomers, unreacted butene-1 monomers), gaseous waste products, gaseous contaminants, or combinations thereof.

In one or more of the embodiments disclosed herein, separating the polymerization product into a polymer stream and a gas stream (e.g., at block 63) may generally comprise removing any gases from liquids and/or solids (e.g., the polymer fluff) by any suitable process.

In embodiments as illustrated by FIGS. 1-2, separating the polymerization product into a polymer stream and a gas stream may comprise routing the polymerization product steam 12 to the separator 108.

In an embodiment, the gas stream 18 may comprise hydrogen, nitrogen, methane, ethylene, ethane, propylene, propane, butane, isobutane, pentane, hexane, hexene-1 and heavier hydrocarbons. In an embodiment, ethylene may be present in a range of from about 0.1% to about 15%, alternatively, from about 1.5% to about 5%, alternatively, about 2% to about 4% by total weight of the stream. Ethane may be present in a range of from about 0.001% to about 4%, alternatively, from about 0.2% to about 0.5% by total weight of the stream. Isobutane may be present in a range from about 80% to about 98%, alternatively, from about 92% to about 96%, alternatively, about 95% by total weight of the stream.

In one or more embodiments, separating the mid-polymerization product into a mid-polymer and a mid-gas stream (e.g., at block 73) may generally comprise removing any gases from liquids and/or solids (e.g., the polymer fluff) by any suitable process.

In embodiments as illustrated in FIGS. 3 and 5, separating the mid-polymerization product into a mid-polymer stream and a mid-gas stream may be accomplished in a single-step separation comprising routing the mid-polymerization product steam 15 to a separator 105.

In embodiments as illustrated in FIG. 3, separating the mid-polymerization product into a mid-polymer stream and a mid-gas stream may comprise separating at least one gaseous component from the mid-polymerization product stream 15. Separating at least one gaseous component from the mid-polymerization product stream 15 may yield mid-gas stream 19 and mid-polymer stream 17. Mid-polymerization product stream 15 may comprise hydrogen, ethylene, ethane, polymer, isobutane, or combinations thereof. Mid-gas stream 19 may comprise hydrogen, ethylene, ethane or combinations thereof. Mid-polymer stream 17 may comprise polymer, isobutane, or combinations thereof.

In embodiments as illustrated in FIG. 3, separating the mid-polymerization product into a mid-polymer stream and a mid-gas stream may comprise reducing a pressure of the mid-polymerization product so as to flash ethylene, hydrogen, ethane, or combinations thereof. Mid-polymerization product stream 15 may comprise hydrogen, ethylene, ethane, polymer, isobutane, or combinations thereof. Separator 105 may create a reduction in pressure so that ethylene, hydrogen, and ethane separate, or flash, from the mid-polymerization product so as to yield mid-gas stream 19 comprising hydrogen, ethylene, and ethane.

In embodiments as illustrated in FIG. 5, separating the mid-polymerization product into a mid-polymer stream and a mid-gas stream may comprise introducing a scavenger prior to reactor 106. In embodiments, the scavenger may reduce a concentration of a component, for example, hydrogen. Embodiments illustrated by FIGS. 3 and 5 show stream 35 may be introduced prior to the reactor 106 via, for example, mid-polymerization product stream 15. Alternatively, stream 35 may be introduced in separator 105 or mid-polymer stream 17. Stream 35 may comprise a scavenger. In embodiments, the scavenger may comprise a catalyst. In embodiments, the catalyst may comprise a hydrogenation catalyst. Without intending to be bound by theory, a scavenger may act to consume hydrogen to form ethane which may reduce the hydrogen concentration, even to zero concentration. In embodiments, the hydrogenation catalyst may have a low activity with respect to the polymerization of polyethylene. The hydrogenation catalyst may comprise a metallocene catalyst of the general formula:

$$Cp_2MX_n$$

where Cp is a substituted cyclopentadienyl group; M is a transition metal from Group IVB of the Periodic Table of vanadium; X is a halogen or a hydrocarbyl group having from 1 to 10 carbon atoms; and n is the valency of the metal M minus 2. In embodiments, the metallocene catalyst may comprise $Cp_2 TiCl_2$, also known as titanocene dichloride. The metallocene catalyst may be introduced in an amount of from 2 to 50 ppm by weight of inert diluent in the mid-polymerization product stream 15, alternatively, from 2 to 20 ppm.

In embodiments as illustrated in FIG. 5, reducing a concentration of hydrogen in a stream prior to the second polymerization reactor 106 with a scavenger may improve polymer production capability, for example, may produce a relatively higher molecular weight polymer in polymerization reactor 106 than in polymerization reactor 104. For example, in embodiments where a relatively higher molecular weight polymer in reactor 106 is desired, typically no additional hydrogen is added to the reactor 106 because increased hydrogen concentration in reactor 106 is generally detrimental to producing higher molecular weight polymer. Instead of introducing hydrogen in such embodiments, a hydrogenation catalyst may be introduced in, or prior to, the reactor 106. Embodiments illustrated by FIGS. 3 and 5 show the hydrogenation catalyst may be introduced in stream 35 prior to reactor 106. In one or more embodiments, the polymer produced may comprise polyethylene. In such embodiments, a Zeigler-Natta catalyst may be used as the polymerization catalyst, and the hydrogenation catalyst introduced through stream 35 may comprise a metallocene catalyst. The amount of metallocene catalyst used may be such that the mass ratio of metallocene catalyst to Zeigler-Natta catalyst (i.e., g metallocene/g Zeigler-Natta) may have a range of from about 0.1 to about 2.0, preferably from about 0.25 to about 1.5, more preferably about 0.5-1.0. In an embodiment, the metallocene catalyst may comprise an unbridged metallocene. In an embodiment, an unbridged metallocene may comprise bis (cyclopentadienyl) titanium dichloride, also referred to as titanocene dichloride. Suitable hydrogenation catalysts are disclosed in U.S. Pat. Nos. 6,730,751, 6,221,982, and 6,291,601, which are incorporated herein by reference.

In embodiments as illustrated in FIG. 5, separating the mid-polymerization product into a mid-polymer stream and a mid-gas stream may further comprise separating at least one gaseous component from the mid-polymerization product stream. In such embodiments, mid-polymerization product stream 15 entering the separator 105 may comprise unreacted hydrogen, unconverted ethylene, ethane, polymer, isobutane, or combinations thereof. Mid-gas stream 19 may comprise hydrogen, ethylene, ethane, or combinations thereof; and mid-polymer stream 17 may comprise polymer, isobutane, or combinations thereof. The amount of ethane in mid-gas stream 19 may be greater than the amount of unreacted hydrogen and/or unconverted ethylene.

In embodiments as illustrated in FIG. 4, separating the mid-polymerization product into a mid-polymer stream and a mid-gas stream (e.g., at block 73) may be accomplished in a two-step separation comprising routing the mid-polymerization product stream 15 to separator 126 and routing a hydrogen-reduced product stream 39 from separator 126 to separator 105.

In embodiments as illustrated in FIG. 4, separating the mid-polymerization product into a mid-polymer stream and a mid-gas stream may comprise degassing at least a portion of hydrogen from the mid-polymerization product. Embodiments as illustrated by FIG. 4 show a separator 126 may yield streams 37 and 39. Stream 37 may comprise removed hydrogen, and stream 39 may comprise hydrogen-reduced product. Separator 126 may degas at least a portion of hydrogen from mid-polymerization product stream 15 via a pressure reduction. The reduction in pressure may occur at temperature of less than or equal to the polymerization temperature in the reactor 104, alternatively, greater than 20° C., alternatively, at least 40° C. The reduction in pressure may occur at a pressure less than the pressure in reactor 104. The reduction in pressure may be less than 1.5 MPa. The reduction in pressure may be at least 0.1 MPa. The amount of hydrogen remaining in hydrogen-reduced stream 39 of FIG. 4 may be less than 1% by weight of the amount of hydrogen initially present in the mixture withdrawn from the reactor 104, alternatively, less than 0.5% by weight, alternatively, 0 wt % by weight. Suitable degassing conditions and equipment are disclosed in U.S. Pat. No. 6,225,412, which is incorporated herein by reference.

In embodiments as illustrated in FIG. 4, separating the mid-polymerization product into a mid-polymer stream and a mid-gas stream may further comprise separating at least one gaseous component from the hydrogen-reduced product stream. In such embodiments, hydrogen-reduced product stream 39 entering the separator 105 may comprise hydrogen, ethylene, ethane, polymer, isobutane, or combinations thereof. Mid-gas stream 19 may comprise hydrogen, ethylene, ethane, or combinations thereof; and mid-polymer stream 17 may comprise polymer, isobutane, or combinations thereof. The amount of hydrogen present in the mid-gas stream 19 of FIG. 4 may be less than 1% by weight of the amount of hydrogen initially present in the mixture withdrawn from the reactor 104, alternatively, less than 0.5% by weight, alternatively, 0 wt % by weight.

In one or more of the embodiments disclosed herein, the separators 105, 108, and 126 may be configured to separate a stream (e.g., mid-polymerization product comprising polyethylene, polymerization product comprising polyethylene, hydrogen-reduced product comprising polyethylene) into gases, liquids, solids, or combinations thereof. The product streams 12, 15, and 39 may comprise unreacted, gaseous monomers or optional comonomers (e.g., unreacted ethylene monomers, unreacted butene-1 monomers), gaseous waste products, and/or gaseous contaminants. In embodiments as illustrated in FIG. 4, mid-polymerization product stream 15 may comprise hydrogen. In embodiments as illustrated in FIGS. 1-2, polymerization product stream 12 may comprise hydrogen. As used herein, an "unreacted monomer," for example, ethylene, refers to a monomer that was introduced into a polymerization reactor during a polymerization reaction but was not incorporated into a polymer. As used herein, an "unreacted coonomer," for example, butene-1, refers to a comonomer that was introduced into a polymerization reactor during a polymerization reaction but was not incorporated into a polymer.

In an embodiment, the separators 105, 108, and/or 126 may comprise a vapor-liquid separator. Suitable examples of such a separator may include a distillation column, a flash tank, a filter, a membrane, a reactor, an absorbent, an adsorbent, a molecular sieve, or combinations thereof. In an embodiment, the separator comprises a flash tank. Not seeking to be bound by theory, such a flash tank may comprise a vessel configured to vaporize and/or remove low vapor pressure components from a high temperature and/or high pressure fluid. The separators 105, 108, and/or 126 may be configured such that an incoming stream may be separated into a liquid stream (e.g., a condensate stream) and a gas (e.g., vapor) stream. The liquid or condensate stream may comprise a reaction product (e.g., polyethylene, often referred to as "polymer fluff"). The gas or vapor stream may comprise volatile solvents, gaseous, unreacted monomers and/or optional comonomers, waste gases (secondary reaction products, such as contaminants and the like), or combinations thereof. The separators 105, 108, and 126 may be configured such that the feed stream is flashed by heat, pressure reduction, or both such that the enthalpy of the stream is increased. This may be accomplished via a heater, a flashline heater, various other operations commonly known in the art, or combinations thereof. For example, a flash line heater comprising a double pipe may exchange heat by hot water or steam. Such a flashline heater may increase the temperature of the stream while reducing its pressure.

In one or more embodiments, separating the polymerization product into a polymer stream and a gas stream or separating the mid-polymerization product into a mid-polymer stream and a mid-gas stream may comprise distilling, vaporizing, flashing, filtering, membrane screening, absorbing, adsorbing, or combinations thereof, the polymerization product. In the embodiments illustrated in FIGS. 1-2, separating the polymerization product into a polymer stream and a gas stream yields a gas stream 18 and a polymer stream 14. In the embodiments illustrated in FIGS. 3-5, separating the mid-polymerization product into a mid-polymer stream and a mid-gas stream yields a mid-gas stream 19 and a mid-polymer stream 17.

In one or more one or more of the embodiments disclosed herein, processing the polymer stream (e.g., at block 64) comprises any suitable process or series of processes configured to produce a polymer product as may be suitable for commercial or industrial usage, storage, transportation, further processing, or combinations thereof.

In embodiments as illustrated by FIGS. 1-2, processing the polymer stream may comprise routing the polymer stream 14 to the processor 110. The processor 110 may be configured for the performance of a suitable processing means, non-limiting examples of which include cooling, injection molding, melting, pelletizing, blow molding, extrusion molding, rotational molding, thermoforming, cast molding, the like, or combinations thereof. Various additives and modifiers may be added to the polymer to provide better processing during manufacturing and for desired properties in the end product. Non-limiting examples of such additives may include surface modifiers such as slip agents, antiblocks, tackifiers; antioxidants such as primary and secondary antioxidants; pigments; processing aids such as waxes/oils and fluoroelastomers; and special additives such as fire retardants, antistats, scavengers, absorbers, odor enhancers, and degradation agents.

In an embodiment, the processor 110 may be configured to form a suitable polymer product. Non-limiting examples of suitable polymer products as may result from such processing include films, powders, pellets, resins, liquids, or any other suitable form as will be appreciated by those of skill in the art. Such a suitable output may be for use in, for examples, one or more of various consumer or industrial products. For example, the polymer product may be utilized any one or more of various articles, including, but not limited to, bottles, drums, toys, household containers, utensils, film products, drums, fuel tanks, pipes, geomembranes, and liners. In a particular embodiment, the processor is configured to form pellets for transportation to a consumer product manufacturer. For example, in the embodiments illustrated in FIGS. 1-2, processing the polymer stream yields a polymer product 16 (e.g., pelletized polyethylene).

In one or more of the embodiments disclosed herein, treating a gas stream (e.g., at block 81) and treating a mid-gas stream (e.g., at block 91) may comprise any suitable process or reaction for removing oxygen, oxygenated compounds, oxidizing compounds, or combinations thereof (cumulatively referred to herein as "oxygen") from the gas stream. Suitable processes or reactions will be appreciated by those of skill in the art viewing this disclosure. Non-limiting examples of suitable processes for removing oxygen include various catalyzed reactions, contacting with a chemical species known to react with oxygen, filtering, absorbing, adsorbing, heating, cooling, or combinations thereof.

In embodiments as illustrated by FIG. 2, treating the gas stream may comprise routing the gas stream 18 to the deoxygenator 118. In embodiments as illustrated by FIG. 5, treating the mid-gas stream may comprise routing the mid-gas stream 19 to the deoxygenator 118.

In one or more of the embodiments disclosed herein, the deoxygenator 118 may comprise a device or apparatus configured for the removal oxygen, from a gas stream. Non-limiting examples of a suitable deoxygenator include various reactors (e.g., a fluidized bed reactor or a fixed bed), a filter, or combinations thereof. A suitable deoxygenator 118 may be configured to reduce, prevent, or exclude compounds and/or elements (e.g., oxygen) that may have the effect of poisoning an absorption solvent from reaching the absorption reactor (e.g., as will be disclosed herein).

In the embodiments illustrated by FIG. 2, treating the gas stream yields a treated gas stream 26 being substantially free of oxygen. In the embodiments illustrated by FIG. 5, treating the mid-gas stream yields a treated gas stream 41 being substantially free of oxygen. As used herein "substantially free of oxygen" refers to a fluid stream comprising no more than least about 5% oxygen, alternatively, no more than about 1% oxygen, alternatively, no more than about 0.1% oxygen, alternatively, no more than about 0.01% oxygen by total weight of the stream.

In one or more one or more of the embodiments disclosed herein, separating at least one gaseous component from the gas stream and/or the treated gas stream, collectively referred to as a gas stream, (e.g., at block 65, 65', 75, or 75') generally comprises any suitable method of selectively separating at least a first chemical component or compound from a stream comprising the first chemical component or compound and one or more other chemical components, compounds, or the like. In various embodiments, the gaseous component separated from the gas stream may comprise one or more hydrocarbons. Non-limiting examples of such hydrocarbons include alkanes (e.g., ethane, butane, isobutane, hexane, or combinations thereof) and alkenes or olefin monomers (e.g., ethylene, hexane, or combinations thereof) or optional comonomers (e.g., butene-1). In an embodiment, the gaseous component separated from the gas stream may comprise an unreacted hydrocarbon monomer, e.g., ethylene. Optionally, the gaseous component separated from the gas stream may comprise an unreacted hydrocarbon comonomer, e.g., propene. In an embodiment, the gaseous component separated from the gas stream may comprise an unreacted hydrocarbon monomer (e.g., ethylene, alone or in combination with other hydrocarbons, such as, ethane, isobutane, hexane, or combinations thereof), or optionally, hydrocarbon comonomer (e.g., propene, alone or in combination with other hydrocarbons, such as, isobutane, hexane, or combinations thereof). In an embodiment, the gaseous component separated from the gas stream may comprise ethylene, alone or in combination with isobutane. In an embodiment, capturing isobutane may result in a savings of the cost of the captured isobutane and reduce the presence of isobutane in flare emissions. Non-limiting examples of suitable separating means include distilling, vaporizing, flashing, filtering, membrane screening, absorbing, adsorbing, molecular weight exclusion, size exclusion, polarity-based separation, or combinations thereof.

In an embodiment, separating at least one gaseous component from the gas stream may comprise distilling a gas stream (e.g., gas stream 18 of FIG. 1, treated gas stream 26 of FIG. 2) in one step so as to allow at least one gaseous component to separate from other gaseous components according to temperature(s) of boiling. In such an embodiment, separating at least one gaseous component from the gas stream may comprise distilling a gas stream into a light hydrocarbon stream comprising ethylene, ethane, optionally hydrogen, or combinations thereof. In such an embodiment, separating at least one gaseous component from the gas stream may comprise collecting hexane, hexene, optionally isobutane, or combinations thereof in a distillation bottoms stream. In an additional and/or alternative embodiment, separating at least one gaseous component from the gas stream may comprise collecting isobutane from a side stream of a distillation column.

In the embodiment of the system 100 shown in FIG. 1, distillation column 122 may be configured to separate at least one gaseous component by distillation. Gas stream 18 may be communicated to distillation column 122, and gas stream 18 may comprise the non-solid components of polymerization product stream 12 in the vapor phase (e.g., nitrogen, methane, ethylene, ethane, propylene, propane, butane, isobutane, pentane, hexane, hexene-1, heavier hydrocarbons, or combinations thereof). Gas stream 18 may optionally comprise hydrogen, which may be removed in separators between two polymerization reactors or by hydrogenation catalyst in the polymerization reactor(s), for example. The at least one gaseous component may be emitted from the distillation column 122 in light hydrocarbon stream 25, and the other gaseous components may be emitted from the distillation column 122 in distillation bottoms stream 23. The at least one gaseous component emitted from distillation column 122 in light hydrocarbon stream 25 of FIG. 1 may comprise ethylene and may further comprise other light gases (e.g., ethylene, ethane, methane, carbon dioxide, nitrogen, hydrogen, or combinations thereof). For example, ethylene may be present in light hydrocarbon stream 25 in an amount from about 50% to about 99% by total weight of the light hydrocarbon stream 25, alternatively from about 60% to about 98%, alternatively, from about 70% to about 95%. The other gaseous components emitted from the distillation column 122 in distillation bottoms stream 23 may comprise propylene, propane, butane, isobutane, pentane, hexane, hexene-1, heavier hydrocarbons, or combinations thereof. In an embodiment, the distillation bottoms stream 23 may be free of olefins, alternatively, substantially free of olefins, alternatively, essentially free of olefins. For example, olefins may be present in distillation bottoms stream 23 in an amount less than about 1.0% by total weight of the distillation bottoms stream 23, alternatively, less than about 0.5%, alternatively, less than about 0.1%. In an embodiment, side stream 27 comprising isobutane may be emitted from the distillation column 122 in side stream 27.

In embodiments as illustrated in FIG. 1, side stream 27 or at least a portion of distillation bottoms stream 23 may be recycled. Recycling the side stream 27 or at least a portion of distillation bottoms stream 23 may comprise routing, for example, via a suitable pump or compressor, the side stream 27 or at least a portion of distillation bottoms stream 23 back to and/or introducing the side stream 27 or at least a portion of distillation bottoms stream 23 into the PEP system 100, for example, for reuse in a polymerization reaction. In an embodiment, side stream 27 or at least a portion of distillation bottoms stream 23 may be combined with various other components (catalysts, cocatalysts, etc.) to form a catalyst slurry that may be introduced into one or more of reactors 104, 106. Not intending to be bound by theory, because the side stream 27 or at least a portion of distillation bottoms stream 23 may comprise an olefin-free isobutane stream (alternatively, a substantially olefin-free, as disclosed above), the side stream 27 or at least a portion of distillation bottoms stream 23 may be mixed with catalytic components (e.g., catalysts, cocatalysts, etc.) without the risk of unintended polymerization reactions (e.g., polymerization prior to introduction into the one or more reactors). As such, the side stream 27 or at least a portion of distillation bottoms stream 23 may serve as a source of olefin-free isobutane for a polymerization reaction. Recycling the side stream 27 or at least a portion of distillation bottoms stream 23 (comprising olefin-free isobutane) may provide an efficient and/or cost-effective means of supplying isobutane for operation of the polymerization reaction process. In an alternative embodiment, side stream 27 or at least a portion of distillation bottoms stream 23 may be routed to storage for subsequent use in a polymerization reaction or employed in any other suitable process.

In an embodiment, at least a portion of the side stream 27 or at least a portion of distillation bottoms stream 23 may be returned to the distillation column 122. For example, side stream 27 or at least a portion of distillation bottoms stream 23 may be routed via a reboiler to the distillation column 122 for additional processing.

The distillation column 122 may be configured and/or sized provide for separation of a suitable volume of gases (e.g., the light hydrocarbon stream 25 of FIG. 1). For example, the distillation column 122 may be operated at a temperature in a range of from about 50° C. to about 20° C., alternatively, from about 40° C. to about 10° C., alternatively, from about 30 to about 5° C., and a pressure in a range of from about 14.7 psia to about 529.7 psia, alternatively, from about 15.7 psia to about 348 psia, alternatively, from about 85 psia to about 290 psia. The distillation column 122 may be configured and/or sized to provide for separation of a suitable volume of gas stream 18 or a treated gas stream (e.g., stream 26 of FIG. 2). As will be appreciated by one of skill in the art, the gas stream 18 (optionally, a treated gas stream) may remain and/or reside within distillation column 122 for any suitable amount of time as may be necessary to provide sufficient separation of the components of gas stream 18 (optionally, a treated gas stream). In an embodiment, distillation column 122 may be provided with at least two outlets.

In an embodiment, the distillation column 122 may be configured and/or operated such that each of light hydrocarbon stream 25 of FIG. 1, optional side stream 27, and the distillation bottoms stream 23 may comprise a desired portion, part, or subset of components of the gas stream 18 (optionally, treated gas stream). For example, as will be appreciated by one of skill in the art with the aid of this disclosure, the location of a particular stream inlet or outlet, the operating parameters of the distillation column 122, the composition of the gas stream 18 (optionally, treated gas stream), or combinations thereof may be manipulated such that a given stream may comprise a particular one or more components of the gas stream 18 (optionally, treated gas stream).

In an alternative embodiment, separating at least one gaseous component from the gas stream may comprise distilling a gas stream (e.g., gas stream 18 or treated gas stream 26) in two steps, so as to allow at least one gaseous component to separate from other gaseous components according to temperature(s) of boiling in a first separation, and so as to allow at least another gaseous component to separate from the other gaseous components according to temperature(s) of boiling in a second separation. In such an embodiment, separating at least one gaseous component from the gas stream in a first separation may comprise distilling the gas stream to form an intermediate hydrocarbon stream comprising ethylene, ethane, hydrogen, isobutane, or combinations thereof. In such an embodiment, separating at least one gaseous component from the gas stream may comprise collecting hexane, optionally hexene, or combinations thereof in a distillation bottoms stream of a distillation column of the first separation. Additionally, separating at least one gaseous component from the gas stream in a second separation may comprise distilling ethylene, ethane, optionally hydrogen, or combinations thereof from the intermediate hydrocarbon stream; collecting hexane, optionally hexene, optionally isobutane, or combinations thereof in a distillation bottoms stream of the second separation; and optionally collecting isobutane from a side stream of the distillation column of the second separation.

In the embodiment of the system 200 shown in FIG. 2, distillation columns 126 and 124 may be configured to separate at least one gaseous component from treated gas stream 26 or gas stream 18. Treated gas stream 26 and gas stream 18 may comprise the non-solid components of polymerization product stream 12 in the vapor phase (e.g., nitrogen, methane, ethylene, ethane, propylene, propane, butane, isobutane, pentane, hexane, hexene-1, heavier hydrocarbons, or combinations thereof). Treated gas stream 26 and gas stream 18 may optionally comprise hydrogen, which may be removed in separators between two polymerization reactors or by dehydrogenation catalyst in the polymerization reactor(s), for example. Treated gas stream 26 or gas stream 18 may be distilled to form intermediate hydrocarbon stream 29. Non-distilled components in the distillation column 126 may emit from the distillation column 126 in distillation bottoms stream 43. Side stream 45 may optionally emit from the distillation column 126.

Intermediate hydrocarbon stream 29 may be characterized as comprising, alternatively, comprising substantially, alternatively, consisting essentially of, alternatively, consisting of, $C_4$ and lighter hydrocarbons (e.g., butane, isobutane, propane, ethane, or methane) and any light gases (e.g., hydrogen or nitrogen). For example, $C_4$ and lighter hydrocarbons and gases may be present in the intermediate hydrocarbon stream 29 in an amount of from about 80% to about 100% by total weight of the intermediate hydrocarbon stream, alternatively from about 90% to about 99.999999%, alternatively from about 99% to about 99.9999%, alternatively, $C_5$ and heavier hydrocarbons may be present in the intermediate hydrocarbon stream 29 in an amount from 0% to about 20% by total weight of the intermediate hydrocarbon stream, alternatively from about 10% to about 0.000001%, alternatively from about 1.0% to about 0.0001%. Also, for example, at least 90% by weight of the treated gas stream 26 or gas stream 18 of the $C_4$ and lighter hydrocarbons and gases may be present in the intermediate hydrocarbon stream 29, alternatively, at least 98%, alternatively, at least 99%.

In an embodiment, distillation bottoms stream 43 may be characterized as comprising $C_6$ and heavier components such as alkanes, that is, alkanes larger than hexane (e.g., heptane and/or other large alkanes). In an embodiment, hydrocarbons other than $C_6$ and heavier alkanes may be present in the distillation bottoms stream 43 in an amount less than about 15%, alternatively, less than about 10%, alternatively, less than about 5% by total weight of the distillation bottoms stream 43. In an embodiment, the distillation bottoms stream 43 may be directed to additional processing steps or methods, or alternatively they may be disposed of, as appropriate. In an embodiment, distillation bottoms stream 43 may be directed to a flare for disposal.

In an embodiment, side stream 45 may be characterized as comprising hexene. For example, hexene may be present in side stream 45 in an amount of from about 20% to about 98% by total weight of the side stream 45, alternatively from about 40% hexene to about 95%, alternatively from about 50% hexene to about 95% hexene.

In an embodiment, the side stream 45 may be recycled. In the embodiment of FIG. 2, recycling the side stream 45 may comprise routing, for example, via a suitable pump or compressor, the side stream 45 back to and/or introducing the side stream 45 into the PEP system 200, for example, for reuse in a polymerization reaction. Recycling the side stream 45 (e.g., comprising hexene) may provide an efficient and/or cost-effective means of supplying hexene for operation of the polymerization reaction process. In an embodiment, the hexene of side stream 45 may be employed in the polymerization reaction as, for example, a comonomer in the reaction. In an alternative embodiment, side stream 45 may be routed to storage for subsequent use in a polymerization reaction or employed in any other suitable process.

In an embodiment, distillation column 126 may be provided with one or more inlets and at least two outlets. The distillation column 126 may be operated at a suitable temperature and pressure, for example as may be suitable to achieve separation of the components of the treated gas stream 26 or gas stream 18. For example, the distillation column 126 may be operated at a temperature in a range of from about 15° C. to about 233° C., alternatively, from about 20° C. to about 200° C., alternatively, from about 20° C. to about 180° C., and/or a pressure in a range of from about 14.7 psi to about 527.9 psi, alternatively, from about 15.7 psi to about 348 psi, alternatively, from about 85 psi to about 290 psi. The distillation column 126 may be configured and/or sized provide for separation of a suitable volume of gases (e.g., the flash gas stream). As will be appreciated by one of skill in the art viewing this disclosure, the treated gas stream 26 or gas stream 18 may remain and/or reside within distillation column 126 for any suitable amount of time, for example an amount of time as may be necessary to provide sufficient separation of the components of distillation column 126.

In an embodiment, the treated gas stream 26 or gas stream 18 may be introduced into the distillation column 126 without a compressive step, that is, without compression of the treated gas stream 26 or gas stream 18 after it is emitted from the separator 108 and before it is introduced into the distillation column 126. In another embodiment, the treated gas stream 26 or gas stream 18 may be introduced into the distillation column 126 at substantially the same pressure as the outlet pressure of separator 108 (e.g., a pressure of from about 14.7 psia to about 527.9 psia, alternatively, from about 15.7 psia to about 348 psia, alternatively, from about 85 psia to about 290 psia at the outlet of the flash chamber 130). In still another embodiment, the treated gas stream 26 or gas stream 18 may be introduced into the distillation column 126 without a significant compressive step. In an embodiment, treated gas stream 26 or gas stream 18 may be introduced into distillation column 126 at a pressure in a range of from about 25 psi less than the pressure at which the gas stream 18 was emitted from the separator 108 to about 25 psi greater than the pressure at which the gas stream 18 was emitted from the separator 108, alternatively, from about 15 psi less than the pressure at which the gas stream 18 was emitted from the separator 108 to about 15 psi greater than the pressure at which the gas stream 18 was emitted from the separator 108, alternatively, from about 5 psi less than the pressure at which the gas stream 18 was emitted from the separator 108 to about 5 psi greater than the pressure at which the gas stream 18 was emitted from the separator 108. In an embodiment, the treated gas stream 26 or gas stream 18 may be introduced into the distillation column 126 at a pressure in a range of from about 14.7 psia to about 527.8 psia, alternatively, from about 15.7 psia to about 348 psia, from about 85 psia to about 290 psia.

In an embodiment, the distillation column 126 may be configured and/or operated such that each of the intermediate hydrocarbon stream 29, the distillation bottoms stream 43, and an optional side stream 45 may comprise a desired portion, part, or subset of components of the gas stream 18 or treated gas stream 26. For example, as will be appreciated by one of skill in the art with the aid of this disclosure, the location of a particular stream outlet, the operating parameters of the distillation column 126, the composition of the treated gas stream 26 or gas stream 18, or combinations thereof may be manipulated such that a given stream may comprise a particular one or more components of the treated gas stream 26 or gas stream 18.

In the embodiment of the system 200 shown in FIG. 2, the intermediate hydrocarbon stream 29 may be separated in the distillation column 124 to form light hydrocarbon stream 25, distillation bottoms stream 33, and optionally, side stream 31. Light hydrocarbon stream 25 may comprise ethylene, ethane, optionally hydrogen, or combinations thereof. Distillation bottoms stream 33 may comprise isobutane. Side stream 31 may comprise isobutane. The isobutane of distillation bottoms stream 33 may comprise a different grade of isobutane than side stream 31. For example, distillation bottoms stream 33 may comprise isobutane that is substantially free of olefins, and side stream 31 may comprise a recycle isobutane which may include olefins.

At least one gaseous component may be emitted from the distillation column 124 in light hydrocarbon stream 25, and the other gaseous components may be emitted from the distillation column 124 in distillation bottoms stream 33. The at least one gaseous component emitted from distillation column 124 in light hydrocarbon stream 25 of FIG. 2 may comprise ethylene and may further comprise other light gases (e.g., ethylene, ethane, methane, carbon dioxide, nitrogen, hydrogen, or combinations thereof). For example, ethylene may be present in light hydrocarbon stream 25 in an amount from about 50% to about 99% by total weight of the light hydrocarbon stream 25, alternatively from about 60% to about 98%, alternatively, from about 70% to about 95%.

The other gaseous components emitted from the distillation column 124 in distillation bottoms stream 33 may comprise propylene, propane, butane, isobutane, pentane, hexane, hexene-1, heavier hydrocarbons, or combinations thereof. In an embodiment, the distillation bottoms stream 33 may be free of olefins, alternatively, substantially free of olefins, alternatively, essentially free of olefins. For example, olefins may be present in distillation bottoms stream 33 in an amount less than about 1.0% by total weight of the distillation bottoms stream 33, alternatively, less than about 0.5%, alternatively, less than about 0.1%. In an embodiment, side stream 31 comprising, alternatively, consisting of, isobutane may be emitted from the distillation column 124 in side stream 31.

In an embodiment, side stream 31 or at least a portion of distillation bottoms stream 33 may be recycled. Recycling the side stream 31 or at least a portion of distillation bottoms stream 33 may comprise routing, for example, via a suitable pump or compressor, the side stream 31 or at least a portion of distillation bottoms stream 33 back to and/or introducing the side stream 31 or at least a portion of distillation bottoms stream 33 into the PEP system 200, for example, for reuse in a polymerization reaction. In an embodiment, side stream 31 or at least a portion of distillation bottoms stream 33 may be combined with various other components (catalysts, cocatalysts, etc.) to form a catalyst slurry that may be introduced into one or more of reactors 104, 106. Not intending to be bound by theory, because at least a portion of distillation bottoms stream 33 may be free of olefins and may comprise isobutane, the distillation bottoms stream 33 may be mixed with catalytic components (e.g., catalysts, cocatalysts, etc.) without the risk of unintended polymerization reactions (e.g., polymerization prior to introduction into the one or more reactors). As such, at least a portion of distillation bottoms stream 33 may serve as a source of olefin-free isobutane for a polymerization reaction. Recycling the side stream 31 or at least a portion of distillation bottoms stream 33 may provide an efficient and/or cost-effective means of supplying isobutane for operation of the polymerization reaction process. In an alternative embodiment, side stream 31 or at least a portion of distillation bottoms stream 33 may be routed to storage for subsequent use in a polymerization reaction or employed in any other suitable process.

In an embodiment, at least a portion of the side stream 31 or at least a portion of distillation bottoms stream 33 may be returned to the distillation column 124. For example, side stream 31 or at least a portion of distillation bottoms stream 33 may be routed via a reboiler to the distillation column 124 for additional processing.

The distillation column 124 may be configured and/or sized provide for separation of a suitable volume of gases (e.g., the light hydrocarbon stream 25 of FIG. 2). For example, the distillation column 124 may be operated at a temperature in a range of from about 50° C. to about 20° C., alternatively, from about 40° C. to about 10° C., alternatively, from about 30 to about 5° C., and a pressure in a range of from about 14.7 psia to about 529.7 psia, alternatively, from about 15.7 psia to about 348 psia, alternatively, from about 85 psia to about 290 psia. The distillation column 124 may be configured and/or sized to provide for separation of a suitable volume of gas stream 18 or a treated gas stream 26. As will be appreciated by one of skill in the art, the treated gas stream 26 or gas stream 18 may remain and/or reside within distillation column 124 for any suitable amount of time as may be necessary to provide sufficient separation of the components of treated gas stream 26 or gas stream 18. In an embodiment, distillation column 124 may be provided with at least two outlets.

In an embodiment, the distillation column 124 may be configured and/or operated such that each of light hydrocarbon stream 25 of FIG. 2 and the distillation bottoms stream 33 may comprise a desired portion, part, or subset of components of the treated gas stream 26 or gas stream 18. For example, as will be appreciated by one of skill in the art with the aid of this disclosure, the location of a particular stream inlet or outlet, the operating parameters of the distillation column 124, the composition of the treated gas stream 26 or gas stream 18, or combinations thereof may be manipulated such that a given stream may comprise a particular one or more components of the treated gas stream 26 or gas stream 18.

In an alternative and/or additional embodiment, separating at least one gaseous component from the gas stream may comprise contacting the gas stream with the absorbent (e.g., an absorption solvent system, as disclosed herein), for example, so as to allow the gaseous component to be absorbed by the absorbent. In such an embodiment, separating at least one gaseous component from the gas stream comprises selectively absorbing the at least one gaseous component from a gas stream. In such an embodiment, absorbing the at least one gaseous component from the gas stream generally comprises contacting the gas stream with a suitable absorbent, allowing the at least one component to be absorbed by the absorbent, and, optionally, removing a waste stream comprising unabsorbed gases. In an additional embodiment, separating at least one gaseous component from the gas stream may further comprise liberating the absorbed gaseous component from the absorbent.

In an embodiment, contacting the gas stream with the absorbent may comprise any suitable means of ensuring sufficient contact between the gas stream and the absorbent. Non-limiting examples of suitable means by which to provide sufficient contact between the gas stream and the absorbent include the use of various reactor systems, such as those disclosed above (e.g., an absorption column or sparged or mixed tank). Not intending to limited by theory, a suitable reactor system may ensure contact between a two or more gaseous, liquid, and or solid compositions by agitating or mixing the two components in the presence of each other, circulating, dispersing, or diffusing a first composition through or within a second composition, or various other techniques known to those of skill in the art. In an embodiment, the gas stream and the absorbent may be brought into contact in a suitable ratio. Such a suitable ratio of gas stream to absorbent may be in a range of from about 1,000 lb/hr:1000 gpm to about 2,500 lb/hr:25 gpm, alternatively, from about 1000 lb/hr:250 gpm to about 2500 lb/hr:100 gpm, alternatively, about 1875 lbs/hr:250 gpm.

In an embodiment as illustrated by FIGS. 1-5, separating at least one gaseous component from the gas stream (e.g., gas stream 18 of FIG. 1 or treated gas stream 26 of FIG. 2 or mid-gas stream 19 of FIGS. 3-5) may comprise routing the gas stream to the absorption reactor 116. In one or more of the embodiments disclosed herein, the absorption reactor 116 may comprise a reactor configured to selectively absorb at least a first chemical component or compound from a stream comprising the first chemical component or compound and one or more other chemical components, compounds, or the like. Non-limiting examples of suitable absorption reactors and/or absorption reactor configurations include an absorption (distillation) tower, a pressure-swing absorption (PSA) configuration, a sparger tank, an agitation reactor, one or more compressors, one or more recycle pumps, or combinations thereof.

In an embodiment, the absorption reactor may be configured to dissipate a gas within a liquid (e.g., by bubbling the gas through the liquid). For example, in an embodiment, the absorption reactor 116 may include a solvent circulation system configured to circulate solvent through the absorption reactor 116. The solvent circulation flow rate may be determined by the operating conditions of the absorption system, as is disclosed herein below. In an embodiment, the absorption reactor 116 may comprise and/or be in fluid communication with one or more pumps configured to recirculate solvent via and/or within the absorption reactor 116. In an additional and/or alternative embodiment, the absorption reactor 116 may comprise a packed bed or column configured to maintain smaller bubble sizes (e.g., of the gas being dissipated within the liquid), for example, so as to maintain a relatively large surface area of contact between the gas and the liquid, for example, so as to maintain an efficiency of mass transfer and/or absorption of the gas into the liquid. In an embodiment, the packing material of the packed bed or column may comprise a polymeric material, metallic material, or combinations thereof. In an embodiment, the absorption reactor 116 may have multiple packed beds or columns. In an embodiment, only a section of the absorption reactor 116 may have a packing material. In an embodiment, the packing material of a packed absorption reactor 116 may have a random packing or may have a structured packing. An example of a suitable absorption reactor is illustrated in the Gas Processors Association, "Engineering Data Book" $10^{th}$ ed. at FIG. 19-16.

In an embodiment where the absorption reactor 116 comprises a solvent reactor, the absorption reactor may comprise a suitable absorption solvent system, as will be disclosed herein. Such an absorption reactor 116 may be configured to retain the absorption solvent system. For example, the absorption solvent system may be retained within the reactor as a liquid, as a fixed bed, or as a fluidized bed.

In an embodiment, a suitable absorption solvent system may be capable of reversibly complexing with the ethylene and/or isobutane. Such an absorption solvent system may generally comprise a complexing agent and a solvent. In an embodiment, an absorption solvent system may be characterized as having a selectivity of ethylene to ethane where ethylene and ethane are present at the same partial pressure of about 40:1 at approximately 14 psi, about 12:1 at approximately 20 psi, about 6:1 at approximately 40 psi, and about 3:1 at approximately 180 psi partial pressure. In an embodiment, the solvent system may be further characterized as having a high contaminant tolerance and as exhibiting high stability at increased and/or fluctuating temperatures and/or pressures, or combinations thereof.

In an embodiment, the complexing agent may comprise a metallic salt. In such an embodiment, the metallic salt may comprise a salt of one or more transition metals and a weakly-ionic halogen. Non-limiting examples of suitable transition metals include silver, gold, copper, platinum, palladium, or nickel. Non-limiting example of suitable weakly-ionic halogens include chlorine and bromine. In an embodiment, a suitable transition metal salt may be characterized as having a high specificity for olefins. Non-limiting examples of suitable transition metal-halogen salts include silver chloride (AgCl) and copper chloride (CuCl). In a particular embodiment, the salt employed in the absorption solvent system comprises CuCl. Not seeking to be bound by theory, such a metallic salt may interact with the double carbon bonds of olefins (e.g., ethylene).

In an embodiment, the complexing agent may comprise a copper (I) carboxylate. In such an embodiment, suitable copper (I) carboxylates may comprise salts of copper (I) and mono-, di-, and/or tri-carboxylic acids containing 1-20 carbon atoms. The carboxylic acid component of the salt may comprise an aliphatic constituent, a cyclic constituent, an aryl constituent, or combinations thereof. Other suitable examples of copper (I) carboxylates include Cu(I) formate, Cu(I) acetate, Cu(I) propionate, Cu(I) butyrate, Cu(I) pentanoate, Cu(I) hexanoate, Cu(I) octanoate, Cu(I) decanoate, Cu(I) 2-ethyl-hexoate, Cu(I) hexadecanoate, Cu(I) tetradecanoate, Cu(I) methyl formate, Cu(I) ethyl acetate, Cu(I) n-propyl acetate, Cu(I) n-butyl acetate, Cu(I) ethyl propanoate, Cu(I) octoate, Cu(I) benzoate, Cu(I) p-t-butyl benzoate, and the like. In an additional embodiment, the complexing agent may comprise an adduct of a copper (I) carboxylate, for example, as disclosed herein, and boron trifluoride ($BF_3$).

In an additional and/or alternative embodiment, the complexing agent may comprise a copper (I) sulfonate. Non-limiting examples of suitable copper (I) sulfonates include the copper (I) salts of sulfonic acids having 4 to 22 carbon atoms. The sulfonic acid component of the salt may comprise an aliphatic constituent, a cyclic constituent, an aryl constituent, or combinations thereof. The aliphatic sulfonic acids can be straight chain or branched. Examples of suitable aliphatic sulfonic acids include, but are not limited to, n-butanesulfonic acid, 2-ethyl-1-hexanesulfonic acid, 2-methylnonanesulfonic acid, dodecanesulfonic acid, 2-ethyl-5-n-pentyltridecanesulfonic acid, n-eicosanesulfonic acid, and the like. Examples of suitable aromatic sulfonic acids include benzenesulfonic acid, alkylbenzenesulfonic acids wherein the alkyl member contains from 1 to 16 carbon atoms, such as p-toluenesulfonic acid, dodecylbenzenesulfonic acid (o-, m-, and p-), p-hexadecylbenzenesulfonic acid, and the like, naphthalenesulfonic acid, phenolsulfonic acid, naphtholsulfonic acids, and halobenzenesulfonic acids, such as p-chlorobenzenesulfonic acid, p-bromobenzenesulfonic acid, and the like.

In an embodiment the complexing agent may further comprise a hindered olefin. For example, the complexing agent may comprise such a hindered olefin in an embodiment wherein the complexing agent forms a copper complex with insufficient solubility. An example of such a hindered olefin is a propylene tetramer (i.e. dodecene). Not intending to be bound by theory, the hindered olefin may increase the solubility of the copper complex while being easily displaced by ethylene.

In various embodiments, the complexing agent may comprise one or more of the complexing agents disclosed in U.S. Pat. Nos. 5,104,570; 5,191,153; 5,259,986; and 5,523,512, each of which is incorporated by reference in its entirety.

In an embodiment, the solvent may comprise an amine or an amine complex, an aromatic hydrocarbon, an olefin, or combinations thereof. Non-limiting examples of solvent amines include pyridine, benzylamine, and aniline. For example, the amine may comprise an aniline (phenylamine, aminobenzene); alternatively, aniline combined with dimethylformamide (DMF), and in embodiments, aniline and N-methylpyrrolidone (NMP). In an embodiment where the solvent comprises an aromatic hydrocarbon, the aromatic hydrocarbon may comprise an unsubstituted or alkyl substituted aryl groups. In such an embodiment, the aromatic hydrocarbon may be in the liquid phase under normal, ambient conditions. Suitable non-limiting examples include toluene, xylene, and the like. In embodiments where the solvent comprises an olefin, non-limiting examples include olefins having 10 to 16 carbon atoms. For example, the olefin may comprise propylene tetramer, dodecene, tetradecene, hexadecene, or combinations thereof.

In an embodiment, the solvent may be characterized as aprotic, that is, as not including a dissociable hydrogen atom. Not intending to be bound by theory, a dissociable hydrogen solvent may result in the hydrogenation of the double bond between carbons in an olefin such as ethylene. Further, the solvent may be characterized as polar, as having a slight polarity, or as having unidirectional, electric charge. Not intending to be bound by theory, a polar solvent may interact with and at least partially solubilize the salt.

In an embodiment, the solvent may be characterized as a liquid produced industrially in relatively high volumes, having a relatively low cost, being easily transportable, or combinations thereof. The solvent may be further characterized as capable of retaining a complexed olefin-metal salt or retaining a weakly ionic metal salt despite fluctuations in temperature and/or pressure.

In an embodiment, the absorption solvent system may comprise copper chloride, aniline, and dimethylformamide (CuCl/aniline/DMF). In an alternative embodiment, the absorption solvent system may comprise copper chloride, aniline, and N-methylpyrrolidone (CuCl/aniline/NMP). In such an embodiment, a CuCl/aniline/NMP solvent system may be characterized as having increased volatile stability at lower pressures and higher temperatures. In alternative embodiments, the absorption solvent system may comprise copper (I) carboxylate and an aromatic solvent such as toluene or xylene. In alternative embodiments, the absorption solvent system may comprise copper (I) sulfonate and an aromatic solvent such as toluene or xylene. In alternative embodiments, the absorption solvent system may comprise an adduct of copper (I) carboxylate and $BF_3$ in an aromatic solvent such as toluene or xylene.

In an embodiment, the absorption solvent system may comprise copper (I) 2-ethyl-hexanoate and propylene tetramer. In an embodiment, the absorption solvent system may comprise copper (I) 2-ethyl-hexanoate and dodecene. In an embodiment, the absorption solvent system may comprise copper (I) hexadecanoate and hexadecene. In an embodiment, the absorption solvent system may comprise copper (I) tetradecanoate and tetradecene.

In an embodiment, allowing the at least one component to be absorbed by the absorbent may comprise allowing the at least one component to become reversibly bound, linked, bonded or combinations thereof to the absorbent or a portion thereof, for example, via the formation of various links, bonds, attractions, complexes, or combinations thereof. For example, in an embodiment where the absorbent comprises an absorption solvent system (e.g., a CuCl/aniline/DMF solvent system or a CuCl/aniline/NMP solvent system), allowing absorption of the at least one component may comprise allowing a complex to form between the absorbent and the at least one component, referred to as an absorbed component complex (e.g., an absorbed ethylene complex).

Allowing absorption of the at least one component may further comprise providing and/or maintaining a suitable pressure of the environment in which the gas stream and absorbent are brought into contact, providing and/or maintaining a suitable partial pressure of a gas, providing and/or maintaining a suitable temperature in the environment in which the gas stream and absorbent are brought into contact, catalyzing the absorption, or combinations thereof. Not intending to be bound by theory, the absorption of the at least one component by the absorbent may be improved at a suitable temperature and/or pressure.

In an embodiment, the absorption reactor 116 may be capable of selectively inducing thermal and/or pressure fluctuations, variations, or cycles. In an embodiment, the absorption reactor 116 may be configured to selectively absorb and/or induce the absorption of an unreacted ethylene monomer (and optionally, comonomer) from a composition comprising various other gases (e.g., ethane, optionally hydrogen). In another embodiment, the absorption reactor 116 may be configured to selectively absorb and/or induce the absorption of butane, particularly, isobutane, from a composition comprising various other gases. In still another embodiment, the absorption reactor 116 may be configured to selectively absorb both unreacted ethylene and butane, particularly, isobutane, from a composition comprising various other gases (e.g., ethane, optionally hydrogen).

Figure 11:
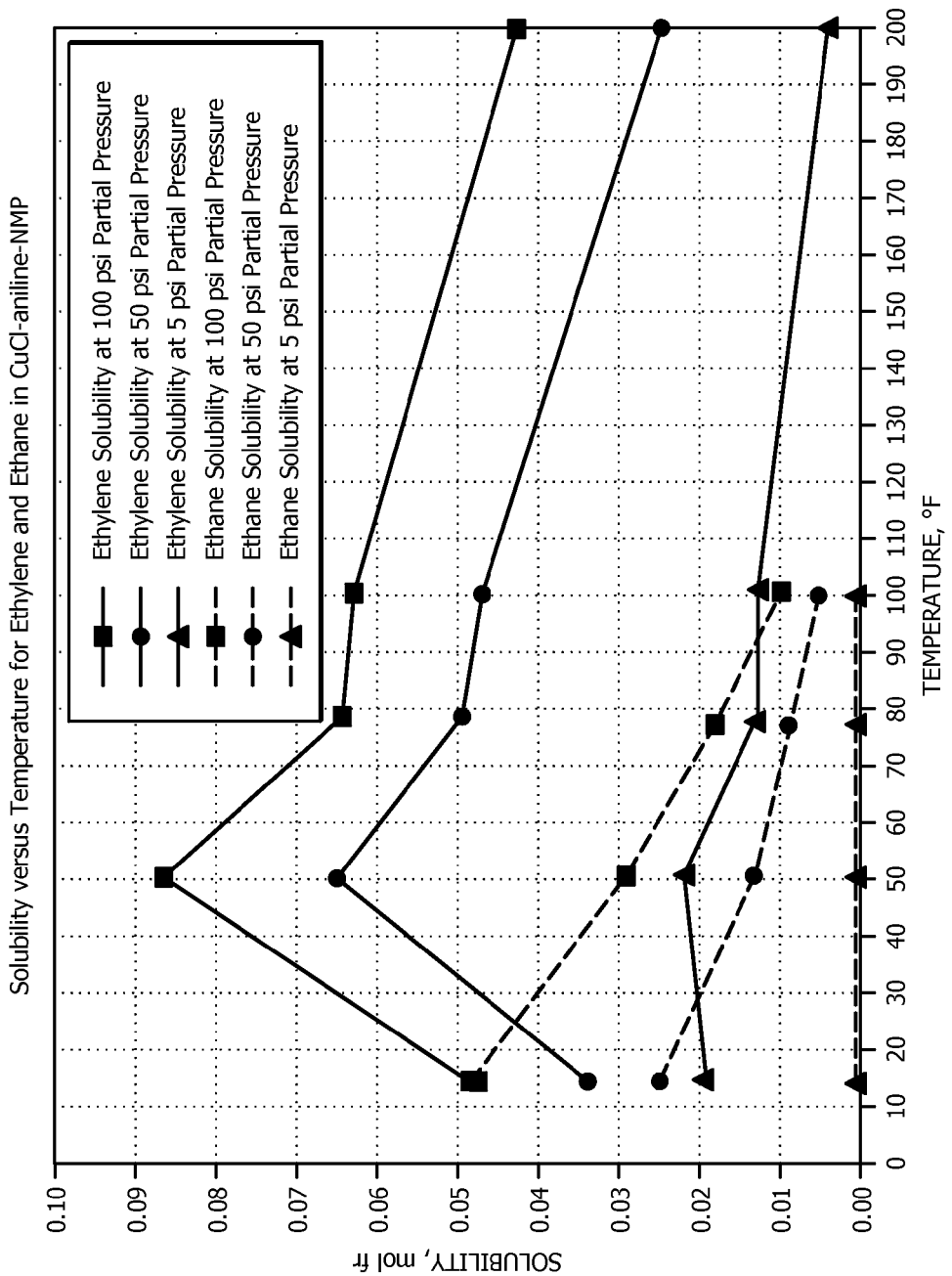
FIG. 11 is a graph illustrating solubility versus temperature for ethylene and ethane in an absorption solvent system.

In an embodiment, the absorption reactor 116 may be configured to provide or maintain a suitable temperature, for example, as may be dependent upon the phase in which the absorption reactor operates at a given time. For example, the absorption reactor 116 may be configured to provide or maintain a suitable temperature, for example, for the purpose of increasing absorption of a desired chemical species, decreasing absorption of a desired chemical species, flashing an unabsorbed gas from the reactor 116, recovering unreacted ethylene from the absorption reactor 116, regenerating absorbent in the absorption reactor 116, or combinations thereof. In an embodiment, such a suitable temperature may be in a range of from about 40° F. to about 110° F., alternatively, from about 40° F. to about 60° F., alternatively, from about 45° F. to about 55° F., alternatively, from about 50° F. to about 55° F., alternatively about 50° F. For example, it has been found the operating temperature of the absorption reactor 116 (and absorption solvent system) in a temperature range of from about 40° F. to about 110° F., alternatively, from about 40° F. to about 60° F., alternatively about 50° F. may yield an unexpected increase in the absorption of ethylene relative to the absorption of ethane. Not intending to be bound by theory, one skilled in the art will appreciate (for example, based on partial pressure concepts from Raoult's law) the expectation for solubility of ethylene and ethane in an absorbent solvent to increase at decreasing temperatures. However, contrary to such expectations, it has been found that the amount of ethylene absorbed in the absorbent solvent and/or the absorbent solvent system of the disclosed embodiments decreases as the temperature decreases below 50° F. Because of this unexpected phenomenon, absorption of ethylene may be greatest for temperatures in a range of from about 40° F. to about 110° F., alternatively, in a range of from about 40° F. to about 60° F., alternatively, at a temperature of about 50° F. FIG. 11 is graph showing the solubility at varying temperatures for ethylene and ethane in a copper chloride, aniline, NMP absorbent solvent system. The graph illustrates the expected solubility trend of ethane and the unexpected solubility trend of ethylene across the temperatures discussed above.

In an embodiment, the absorption reactor 116 may be configured to provide or maintain a suitable temperature in a range from about 40° F. to about 110° F. during absorption of one or more components of the gas stream (e.g., ethylene and/or isobutane). As disclosed above, it has been found that ethylene solubility is unexpectedly greatest at temperature in a range of from about 40° F. to about 60° F. In an embodiment, the absorption reactor 116 may be operated at a temperature of from about 40° F. to about 60° F., alternatively a temperature of about 50° F. during absorption of ethylene and/or isobutene from a gas stream. In an alternative embodiment, the absorption reactor may be operated at a temperature of from about 60° F. to about 110° F., or from about 70° F. to about 90° F. during absorption of ethylene and/or isobutene from a gas stream. For example, such absorption temperatures of the absorption reactor 116 may be suitable as an economic alternative to operating at a lower temperature (which may require energy expenditure with cooling, for example). For example, operating an absorption reactor, like absorption reactor 116, at temperatures in a range of from about 60° F. to about 110° F., or from about 70° F. to about 90° F. may require less energy, which may create a cost savings, by allowing the absorption reactor to be operated at the ambient temperature of a given geographic location.

In an embodiment, the absorption reactor 116 may be configured to provide or maintain a suitable pressure during operation. Such a suitable pressure may be in a range of from about 5 psig to about 500 psig, alternatively, from about 50 psig to about 450 psig, alternatively, from about 75 psig to about 400 psig. In an additional embodiment, the absorption reactor 116 may be configured to provide or maintain a suitable partial pressure of ethylene during operation. Such a suitable ethylene partial pressure may be in a range of from about 1 psia to about 400 psia, alternatively, from about 30 psia to about 200 psia, alternatively, from about 40 psia to about 250 psia, alternatively, from about 40 psia to about 75 psia, alternatively, from about 40 psig to about 60 psig, alternatively about 40 psig, alternatively, about 60 psig. Not intending to be bound by theory, pressurizing the absorption reactor 116 may facilitate absorption of ethylene and/or the formation of a complex of ethylene and the absorption solvent system (e.g., the CuCl/aniline/NMP system). Also, not intending to be bound by theory, the selectivity of the absorption solvent system for ethylene may increase with a decrease in the pressure of the absorption reactor.

In an embodiment, the absorption reactor 116 may be configured for batch and/or continuous processes. For example, in an embodiment, a PEP system may comprise two or more absorption reactors (e.g., such as absorption reactor 116), each of which may be configured for batch operation. For example, by employing two or more absorption reactors, such a system may be configured to allow for continuous operation by absorbing a component of a gas stream into a "first batch" in the first absorption reactor while a "second batch" is prepared for absorption in the second absorption reactor. As such, by cycling between two or more suitable reactors, a system may operate continuously.

Figure 10:
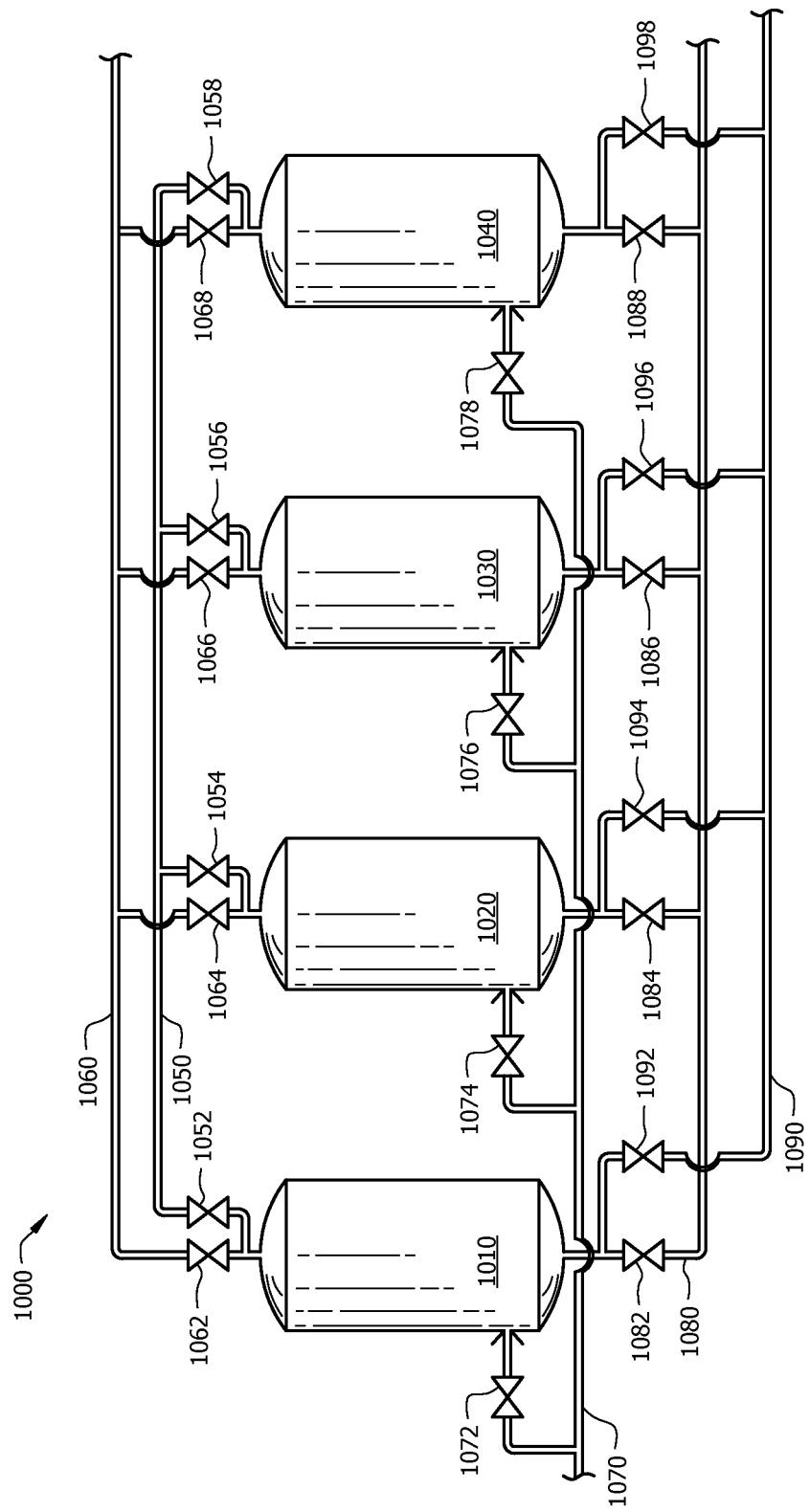
FIG. 10 illustrates a schematic of an embodiment of an absorption reactor having a pressure swing absorption configuration.

For example, in an embodiment two or more absorption reactors (e.g., an absorption reactor system) may be configured for pressure swing absorption (PSA) of ethylene using a liquid solvent, for example, the absorption solvent system or absorption solvent as disclosed herein. In such an embodiment, the absorption reactor 116 may include two or more absorption reactors configured for PSA (e.g., an absorption reactor system). FIG. 10, shows an absorption reactor system 1000 with four absorption reactors 1010, 1020, 1030, and 1040 configured for PSA. Although the embodiment of FIG. 10 illustrates four absorption reactors (e.g., absorption reactors 1010, 1020, 1030, and 1040), one of skill in the art, upon viewing this disclosure, will recognize that two, three, five, six, seven, eight, or more absorption reactors may be similarly employed. In such an embodiment, the each of the absorption reactors may be configured substantially as disclosed herein. In an embodiment, one or more of the reactors 1010, 1020, 1030, and 1040 may be connected via a circulation system (for example, comprising one or more pumps, valves, conduits, and the like) to circulate the liquid solvent in the reactors 1010, 1020, 1030, and 1040 during absorption. The absorption reactors 1010, 1020, 1030, and 1040 may cycle between an absorption phase (in which a gaseous component, such as ethylene and/or isobutane, is absorbed by the absorption solvent and/or absorption solvent system) and a regeneration phase (in which the absorbed and/or complexed gaseous component is liberated from the absorption solvent system and/or the absorption solvent system is prepared for reuse, as will be disclosed herein). For example, the reactors 1010, 1020, 1030, and 1040 may be cycled between the absorption and regeneration phases (e.g., via one or more intermediate phases) on a coordinated basis so that not all reactors 1010, 1020, 1030, 1040 are undergoing absorption or regeneration at the same time. In an embodiment where absorption reactors 1010, 1020, 1030, and 1040 are configured to operate in PSA, the reactors 1010, 1020, 1030, and 1040 serve as both absorbers and as regenerators. In such an embodiment, separate vessels for regeneration may not be required (e.g., as disclosed herein).

As an example of PSA operation on a coordinated basis, at a given phase during such operation, reactor 1010 may operate in the absorption phase, for example, at absorption conditions as disclosed herein. At substantially the same time, reactor 1020 may be pressurized to an intermediate pressure, for example, below that of the absorption pressure. Also, at substantially the same time, reactor 1030 may depressurize from an intermediate pressure to a regeneration pressure, and while reactor 1040 may depressurize from an absorption pressure (from previously being in an absorption phase) to an intermediate pressure. Not intending to be bound by theory, depressurization (e.g., from the absorption pressure to the intermediate pressure and from the intermediate pressure to the regeneration pressure) of each of reactors 1010, 1020, 1030, and/or 1040 following absorption may allow the absorbed gaseous components (e.g., ethylene and/or isobutane) to be liberated from the absorbent and/or the absorbent to be regenerated (e.g., prepared for re-use, as disclosed herein). In an embodiment, the pressure from one or more of the reactors (e.g., reactors 1010, 1020, 1030, and/or 1040) may be utilized to pressurize another of these reactors. For example, in the embodiment of FIG. 10, the pressure of gas in reactor 1040 may be used to pressurize reactor 1020 to the intermediate pressure through line 1050, with valves 1058 and 1084 being in an open position and valves 1082 and 1056 being in a closed position. Valves 1062, 1064, 1066, and 1068 may be switched between an open position and a closed position to allow product nitrogen in stream 1060 to flow in and out of reactors 1010, 1020, 1030, and 1040. Valves 1052, 1054, 1056, and 1058 may be switched between an open position and a closed position to allow pressurization and depressurization of reactors 1010, 1020, 1030, and 1040 through stream 1050. Valves 1082, 1084, 1086, and 1088 may be switched between an open position and a closed position to allow light gas stream 1080 to feed to reactors 1010, 1020, 1030, and 1040 when in the absorption phase. Valves 1092, 1094, 1096, and 1098 may be switched between an open position and a closed position to remove any purge gas from reactors 1010, 1020, 1030, and 1040 through stream 1090.

In an embodiment, a stripping gas, such as isobutane or nitrogen, may be added to the absorption reactors 1010, 1020, 1030, and 1040, for example, through stream 1070 during the regeneration phase. Stream 1070 may be positioned at a bottom of reactors 1010, 1020, 1030, and 1040 so the stripping gas may bubble through the reactor 1010, 1020, 1030, or 1040 (and through any packing materials therein). Valves 1072, 1074, 1076, and 1078 may be switched between open and closed positions to add the stripping gas to the reactors 1010, 1020, 1030, and 1040 during regeneration. Not intending to be bound by theory, the stripping gas may lower the partial pressure of ethylene in the absorption reactors 1010, 1020, 1030, and 1040 during regeneration.

In an embodiment, one or more of the absorption reactors 1010, 1020, 1030, and 1040 may comprise internals to distribute the gas through the liquid absorption solvent and prevent channeling. Suitable internals may include distillation packing that distributes gas and reduces axial mixing of the liquid. Internals may prevent liquid absorption solvent in the absorption reactors 1010, 1020, 1030, and 1040 from mixing so that solvent flow would be first saturated and then a saturation front may move vertically upward through the absorption reactors 1010, 1020, 1030, and 1040.

In an embodiment, separating at least one gaseous component from the gas stream comprises removing a waste stream. In an embodiment, the remaining unabsorbed gas stream components form the waste stream. In an embodiment where the absorbed component comprises ethylene and the absorbent comprises a CuCl/aniline/DMF or a CuCl/aniline/NMP solvent system, such a waste stream may comprise hydrogen, methane, ethane, acetylene, propylene, various other hydrocarbons, volatile contaminants, or combinations thereof. Further, such a waste stream may be substantially free of unreacted ethylene monomers or, optionally, comonomers. As used herein, "substantially free of unreacted ethylene monomers" means that the waste gases comprise less than 50% unreacted ethylene monomers, alternatively, less than 10% unreacted ethylene monomers, alternatively, less than 1.0% unreacted ethylene monomers, alternatively, less than 0.1 unreacted ethylene monomers, alternatively, less than 0.01% unreacted ethylene monomers by total weight of the stream.

In an embodiment, removing the waste stream may comprise cooling the waste stream, and/or reducing or increasing the waste stream pressure such that the waste stream flows to the processing device 114. For example, in an embodiment, the waste stream may be "swept away" by conveying a suitable sweep gas (e.g., an inert or unreactive gas, as disclosed above) through the vessel containing the waste gas (e.g., the absorption reactor 116) at a sufficient pressure, at velocity, or combinations thereof to expel the waste gases therefrom. For example, in the embodiments illustrated by FIGS. 1-5, separating at least one gaseous component from the gas stream yields a waste gas stream 20 being substantially free of unreacted ethylene monomers (optionally, comonomers), alternatively, a waste gas stream having a reduced concentration of unreacted ethylene monomers (optionally, comonomers). For example, the waste gas stream may comprise less than about 30%, alternatively, less than about 25%, alternatively, less than about 20%, alternatively, less than about 15%, alternatively, less than about 10% unreacted ethylene monomers by total weight of the stream. In an additional embodiment, the ethylene may be decreased by a percentage of the ethylene present in the gas stream prior to separating at least one gaseous component therefrom. For example, the waste gas stream may comprise less than about 40%, alternatively, less than about 30%, alternatively, less than about 20% by total weight of the stream of the unreacted ethylene monomers present in the gas stream prior to separation.

In an embodiment, separating at least one gaseous component from the gas stream may further comprise liberating the absorbed gaseous component from the absorbent (e.g., in situ within absorption reactor 116 and/or in another vessel such as regenerator 120). Liberating the absorbed gaseous component from the absorbent generally comprises any suitable means of reversing the various links, bonds, attractions, complexes, or combinations thereof by which the at least one gaseous component is bound, linked, bonded or combinations thereof to the absorbent or a portion thereof. Non-limiting examples of a suitable means by which to liberate the absorbed gaseous component include altering absorption kinetics or the absorption equilibrium of the absorbent, heating or depressurizing the absorbent, altering the partial pressure of the absorbed gas, or combinations thereof.

In an embodiment, the absorbed gaseous component may be liberated (e.g., desorbed and/or decomplexed) from the absorbent within the one or more of such absorption reactors in a regeneration and/or desorption phase. In embodiments, the regeneration phase may comprise regenerating the absorption solvent system so as to yield unreacted ethylene; in embodiments, the regeneration phase may comprise regenerating the absorption solvent system in the absorption reactor 116 so as to yield unreacted ethylene. For example, in the embodiment of FIGS. 1 and 2 (and/or, in an embodiment where the absorption reactor 116 is configured in a PSA configuration, as disclosed herein with respect to FIG. 10), the absorption reactor 116 may be configured to induce the release of the gas absorbed or complexed by the absorption solvent therefrom (e.g., desorption and/or decomplexation of the absorbed and/or complexed ethylene and/or isobutane), as disclosed in detail herein. Not intending to be bound by theory, inducing the release of the absorbed or complexed gas may comprise altering the reaction kinetics or the gas-solvent equilibrium of the absorption solvent system, the temperature of the absorption reactor 116, the pressure of the absorption reactor 116, the partial pressure of the absorbed gas, or combinations thereof. In such an embodiment, the absorption reactor 116 may comprise controls, thermal conduits, electric conduits, compressors, vacuums, the like, or combinations thereof configured to alter the reaction kinetics, the gas-solvent equilibrium, the temperature of the absorption reactor 116, the pressure of the absorption reactor 116, or combinations thereof.

For example, in an embodiment, liberating the absorbed gaseous component may comprise depressurizing the solution comprising the complexed ethylene to a suitable partial pressure. In an additional embodiment, liberating the absorbed gaseous component may comprise heating the solution comprising the complexed ethylene within the absorption reactor 116 (alternatively, within a regenerator 120, as disclosed herein below) to a suitable temperature. Such a suitable temperature may be in a range of from about 110° F. to about 200° F., alternatively, from about 140° F. to about 160° F., alternatively, from about 160° F. to about 200° F., alternatively, from about 180° F. to about 200° F., to encourage release of the absorbed compound (e.g., ethylene and/or isobutane) from the absorption solvent. For example, in a particular embodiment, the absorption reactor 116 (alternatively, the regenerator 120) may be operated at a temperature of from about 160° F. to about 200° F., alternatively, from about 180° F. to about 200° F. during the liberation of the absorbed component (e.g., ethylene and/or isobutene) from the absorption solvent. In an alternative embodiment, the absorption reactor 116 (alternatively, the regenerator 120) may be operated at a temperature of from about 140° F. to about 160° F. during the liberation of the absorbed component (e.g., ethylene and/or isobutene) from the absorption solvent. For example, such liberation temperatures may be suitable as an economic alternative. For example, operation an absorption reactor like absorption reactor 116 (alternatively, a regenerator like regenerator 120) at temperatures in a range of from about 140° F. to about 160° F. during the liberation of the absorbed component may require less energy, which may create a cost savings, by allowing heat derived from other sources (e.g., polymerization reactor coolant, low pressure stream, heat-exchangers upstream of regenerators, heat-exchangers in the absorbent recycle line, polymerization reactors, flash-line heaters, flash vessels, or the like, or combinations thereof) to be utilized to heat the absorption reactor and/or the regenerator.

Additionally, in such an embodiment, the absorption reactor 116 may be configured to evacuate gases (e.g., a previously absorbed and then released gas, such as ethylene) and/or to facilitate the release of the absorbed gas via a pressure differential. The absorption reactor 116 may be configured to provide or maintain a suitable partial pressure. Such a suitable partial pressure may be in a range of from about 0.1 psig to about 40 psig, alternatively, from about 5 psig to about 30 psig, alternatively, from about 5 psig to about 15 psig. In an embodiment, the absorption reactor 116 may be configured to provide or maintain an ethylene partial pressure in a range of from about 0 psia to about 5 psia.

In an alternative embodiment, separating at least one gaseous component from the gas stream may further comprise removing the solution comprising the absorbed component complex (e.g., the absorbed ethylene complex) for further processing. In such an alternative embodiment, the absorption complex comprising the absorbed gaseous component may be removed from the absorption reactor 116 to the regenerator 120 for liberation of the absorbed gaseous component and/or regeneration of the absorption complex as a complexed stream 28. In embodiments, the regenerator 120 may regenerate the absorption solvent system so as to yield unreacted ethylene; in embodiments, the regenerator 120 may regenerate the absorption solvent system in the regenerator 120 so as to yield unreacted ethylene.

In such an embodiment, the complexed stream 28 may comprise ethylene, ethane, and/or isobutane. Ethylene may be present in a range of from about 0.1% to about 10%, alternatively, from about 0.4% to about 5%, alternatively, from about 0.5% to about 2.5% by total weight of the stream. Ethane may be present in a range of from about 0.1% to about 1%, alternatively, from about 0.2% to about 0.5% by total weight of the stream. Isobutane may be present in a range of from about 0.1% to about 1%, alternatively, from about 0.2% to about 0.5% by total weight of the stream.

In one or more of the embodiments disclosed herein, separating a complexed stream into a recycle stream and an absorbent stream (e.g., at block 92) comprises liberating the absorbed gaseous component from the absorbent. As explained above, liberating the absorbed gaseous component from the absorbent generally comprises any suitable means for reversing the various links, bonds, attractions, complexes, or combinations thereof by which the at least one gaseous component is bound, linked, bonded or combinations thereof to the absorbent or a portion thereof. Various processes and/or parameters for liberating an absorbed gaseous component were disclosed above with respect to liberation within the absorption reactor.

In the embodiment illustrated by FIG. 5, separating a complexed stream into a recycle stream and an absorbent stream may comprise routing the complexed stream 28 to the regenerator 120. In one or more one or more of the embodiments disclosed herein, a regenerator 120 may comprise a device or apparatus configured to recover, regenerate, recycle, and/or purify an absorption solvent and/or to liberate an absorbed gas. Non-limiting examples of a suitable regenerator include a flash reactor, a depressurization reactor, a solvent regeneration reactor, or combinations thereof.

In an embodiment, regenerator 120 may be configured to operate on the basis of a pressure differential. In such an embodiment, the regenerator 120 may be configured to provide or maintain a suitable internal pressure. Such a suitable internal pressure may be in a range of from about 0 psig to about 150 psig, alternatively, from about 5 psig to about 30 psig, alternatively, from about 5 psig to about 15 psig, alternatively, from about 0 psig to about 10 psig. In an embodiment, the regenerator 120 may be configured to provide or maintain a suitable partial pressure. Such a suitable partial pressure may be in a range of from about 0 psia to about 50 psia.

In an embodiment, regenerator 120 may be configured to operate on the basis of an elevated temperature. Such a regenerator 120 may be configured to provide or maintain a suitable temperature. Such a suitable temperature may be in a range of from about 110° F. to about 200° F., alternatively, from about 140° F. to about 200° F., alternatively, from about 140° F. to about 160° F., alternatively, from about 160° F. to about 200° F., alternatively, from about 180° F. to about 200° F., to vaporize and/or release an absorbed compound (e.g., ethylene and/or isobutane) from the absorption solvent. In an embodiment, regenerator 120 (e.g., like the absorption reactor 116) may be heated to desorb, or regenerate, the absorption solvent system using heat sources comprising cooling water, low-pressure steam, or combinations thereof. Cooling water, low pressure steam, or a combination thereof may be suitable for heating regenerator 120 (or the absorption reactor 116, as disclosed above) to a temperature of from about 140° F. to about 200° F.

In an embodiment, the regenerator 120 may be configured for batch and/or continuous processes. For example, in an embodiment, a PEP system may comprise two or more absorption regenerators (e.g., such as regenerators 1220 and 1222 of FIG. 12), each of which may be configured for batch operation. As explained above, by employing two or more absorption reactors, such a system may operate to regenerate the absorbent continuously.

In an embodiment, separating a complexed stream into a recycle stream and an absorbent stream may yield a regenerated absorbent stream which may be reused in an absorption reaction and a recycle stream comprising unreacted monomers (optionally, comonomers) which may be reintroduced into or reused in a PEP process. For example, in the embodiment illustrated by FIG. 5, separating a complexed stream 28 into a recycle stream and an absorbent stream yields a recycle stream 22 which may be returned to the purifier 102, for example, and a regenerated absorbent stream 30 which may be returned to the absorption reactor 116, for example.

In an embodiment, liberating the absorbed gas may also yield a recycle stream comprising unreacted monomers (optionally, comonomers) which may be returned to the separator 108 for pressurization (e.g., via one or more compressors located at the separator 108). For example, in the embodiments illustrated by FIGS. 1-5, liberating the absorbed gas yields a recycle stream 22 which may be returned to the separator 108, 105. Pressurizing the recycle stream 22 may yield a reintroduction stream (not shown) which may be reintroduced into or reused in a PEP process. For example, in the embodiments illustrated by FIGS. 1-5, a reintroduction stream may be introduced into the purifier 102. In an alternative embodiment, a recycle stream (such as recycle stream 22) may be pressurized and/or reintroduced into a PEP process without being returned to the separator 108, 105. In an embodiment, the recycle stream 22 may comprise substantially pure ethylene; alternatively, the recycle stream 22 may comprise ethylene and butane, particularly, isobutane. In an embodiment, the gas stream may comprise may comprise nitrogen, ethylene, ethane, and/or isobutane. Ethylene may be present in a range of from about 65% to about 99%, alternatively, from about 70% to about 90%, alternatively, about 75% to about 85% by total weight of the stream. Ethane may be present in a range of from about 1% to about 20%, alternatively, from about 5% to about 15%, alternatively, from about 7.5% to about 12.5% by total weight of the stream. Isobutane may be present in a range of from about 1% to about 20%, alternatively, from about 5% to about 15%, alternatively, from about 7.5% to about 12.5% by total weight of the stream.

In one or more one or more of the embodiments disclosed herein, combusting waste gas stream (e.g., at block 66 or 76) may generally comprise burning or incinerating one or more gaseous components of the waste gas stream 20. In an embodiment, combusting the waste gas stream 20 may further or alternatively comprise cracking, catalytic cracking, pyrolysis, dehydrogenation, scrubbing, converting, treating, or combinations thereof, of the waste gas stream 20 or combustion products.

As disclosed herein, the waste gas stream 20 may comprise volatilized solvents, unreacted gases, secondary products, contaminants, hydrocarbons, or combinations thereof. In an embodiment, the waste gas stream 20 may comprise hydrogen, nitrogen, methane, ethylene, ethane, propylene, propane, butane, isobutane, heavier hydrocarbons, or combinations thereof. Ethylene may be present in a range of from about 1% to about 40%, alternatively, from about 2.5% to about 20% by total weight of the stream. Ethane may be present in a range of from about 5% to about 50%, alternatively, from about 30% to about 40% by total weight of the stream. Isobutane may be present in a range from about 1% to about 20%, alternatively, from about 1.5% to about 5%, alternatively, from about 2% to about 3% by total weight of the stream. Nitrogen may be present in a range from about 10% to about 80%, alternatively, from about 35% to about 50%, alternatively, from about 40% to about 45% by total weight of the stream.

In embodiments as illustrated by FIGS. 1-5, combusting waste gas stream may comprise routing the waste gas stream 20 to the processing device 114. In one or more of the embodiments disclosed herein, the processing device 114 may comprise a combustion device or apparatus, such as a flare. Non-limiting examples of a suitable flare include a torch, incinerator, the like, or combinations thereof. A flare may suitably comprise one or more controllable nozzles, an ignition source, a bypass valve, a pressure relief valve, or combinations thereof. The flare may be configured to provide an environment for the combustion of various waste products, for example, atomic gases (e.g. nitrogen, oxygen), oxides (e.g. carbon monoxide, oxides of nitrogen or sulfur), various unwanted gaseous products, or combinations thereof. In an embodiment, the flare may additionally comprise a device or apparatus configured to selectively remove one or more of contaminants prior to, during, and/or after combustion (e.g., such that a given combustion product is not released into the atmosphere).

In one or more of the embodiments disclosed herein, the processing device 114 may comprise a cracker, catalytic cracker, scrubber, converter, treater, dehydrogenator, deoxygenator, or combinations thereof, for example. In an embodiment, processing device 114 may comprise an ethylene cracker. In the processing device 114, one or more gaseous components, such as ethane, from waste gas stream 20 may be converted to a desired product, such as ethylene monomer. The desired product formed in the processing device 114 may be recycled to one or more of purifier 102, reactor 104, reactor 106, for example.

In other alternative embodiments, waste gas stream 20 may be used as fuel (for example for steam generation or co-gen operations, and/or may be used as fuel and/or a feed to a thermal cracking unit to form ethylene (e.g., to form feed stream 10). In another alternative embodiment, the waste gas from waste gas stream 20 may be exported from the plant to a monomer plant.

In an embodiment, implementation of one or more of the disclosed systems (e.g., PEP systems 100, 200, 300, 400, and/or 500) and/or processes (e.g., PEP processes 600, 700, 800 and/or 900) may allow for the recovery of a substantial portion of the ethylene monomers that would otherwise be lost due to the operation of such systems or processes, for example, by flaring. In an embodiment, one or more of the disclosed systems may allow for the recovery of up to about 75%, alternatively, up to about 85%, alternatively, up to about 90%, alternatively, up to about 95% by total weight of the stream of the ethylene monomers that would otherwise be lost. In an embodiment, one or more of the disclosed systems may allow for the recovery of up to about 75%, alternatively, up to about 85%, alternatively, up to about 90%, alternatively, up to about 95% by total weight of the stream of the isobutane that would otherwise be lost. The recovery of such a portion of the unreacted ethylene monomers may yield a significant economic benefit, for example, by improving the efficiency of usage of ethylene monomers and decreasing capital inputs associated with the acquisition of ethylene monomers. Similarly, the recovery of such a portion of isobutane may yield a significant economic benefit, for example, by decreasing capital inputs associated with the acquisition of isobutane and/or by reducing the presence of isobutane in flare emissions.

In an embodiment, implementation of one or more of the disclosed systems and/or processes may decrease the amount of ethane and/or hydrogen that is transferred to polymerization reactor 106. In an embodiment, implementation of one or more of the disclosed systems and/or processes may decrease the amount of ethane and/or hydrogen that is returned to a polymerization reactor (such as reactors 104 and/or 106) via a recycle stream. By decreasing the amount of ethane contained in a stream to a polymerization reactor, the overall efficiency of the polyethylene production may be improved (for example, by increasing the ethylene concentration without reaching the bubble point in the loop reactor). For example, decreasing the amount of ethane in a stream may improve polymerization reactor efficiency, improve catalyst efficiency, reduce polymer fouling, reduce polymerization downtime, improve production of bimodal polymer types, improve production of copolymers, or combinations thereof.

The various embodiments shown in the Figures may be simplified and may not illustrate common equipment such as heat exchangers, pumps, and compressors; however, a skilled artisan would recognize the disclosed processes and systems may include such equipment commonly used throughout polymer manufacturing.

A skilled artisan will recognize that industrial and commercial polyethylene manufacturing processes may necessitate one or more, often several, compressors or similar apparatuses. Such compressors are used throughout polyethylene manufacturing, for example to pressurize reactors 104, 106 during polymerization. Further, a skilled artisan will recognize that a polyethylene manufacturing process includes one or more deoxygenators and/or similar de-oxidizing apparatuses, for instance purifying solvents or reactants and/or for purging reactors of oxygen. Because the infrastructure and the support therefore, for example to provide power and maintain the compressors and/or deoxygenators, already exists within a commercial polyethylene manufacturing plant, reallocating a portion of these available resources for use in the disclosed systems may necessitate little, if any, additional capital expenditure in order to incorporate the disclosed systems and or processes.

Further, because compressors, deoxygenators, and various other components are already employed in various polyethylene processes and systems, the opportunity for increased operation of such apparatuses may improve the overall efficiency of polyethylene production systems and processes. For example, when a portion of a PEP process or system is taken off-line for maintenance and/or repair, other portions of the system (e.g., a compressor, a deoxygenator, a reactor, etc.) may continue to provide service according to the current processes. Operating and/or reallocating resources for operation of the disclosed PEP systems and/or processes may thereby increase the efficiency with which conventional systems are used.

ADDITIONAL DESCRIPTION

Processes and systems for the component separation in a polymerization system have been described. The following clauses are offered as further description:

Embodiment A. A process for component separation in a polymer production system, comprising:

separating a polymerization product stream into a gas stream and a polymer stream, wherein the gas stream comprises ethane and unreacted ethylene;

distilling the gas stream into a light hydrocarbon stream, wherein the light hydrocarbon stream comprises ethane and unreacted ethylene;

contacting the light hydrocarbon stream with an absorption solvent system, wherein at least a portion of the unreacted ethylene from the light hydrocarbon stream is absorbed by the absorption solvent system; and recovering a waste gas stream from the absorption solvent system, wherein the waste gas stream comprises ethane, hydrogen, or combinations thereof.

Embodiment B. The process of embodiment A, further comprising:

regenerating the absorption solvent system to yield recovered ethylene.

Embodiment C. The process of embodiment A through B, further comprising:

distilling the gas stream into a side stream comprising isobutane.

Embodiment D. A process for component separation in a polymer production system, comprising:

separating a polymerization product stream into a gas stream and a polymer stream, wherein the gas stream comprises ethane and unreacted ethylene;

distilling the gas stream into an intermediate hydrocarbon stream and a first bottoms stream, wherein the intermediate hydrocarbon stream comprises ethane, ethylene, and isobutane;

distilling the intermediate hydrocarbon stream into a light hydrocarbon stream and a second bottoms stream, wherein the light hydrocarbon stream comprises ethane and ethylene;

contacting the light hydrocarbon stream with an absorption solvent system, wherein at least a portion of the unreacted ethylene from the light hydrocarbon stream is absorbed by the absorption solvent system; and recovering a waste gas stream from the absorption solvent system, wherein the waste gas stream comprises ethane, hydrogen, or combinations thereof.

Embodiment E. The process of embodiment D, further comprising:

regenerating the absorption solvent system to yield recovered ethylene.

Embodiment F. The process of embodiment D through E, further comprising:

distilling the intermediate hydrocarbon stream into a side stream comprising isobutane, wherein the second bottoms stream comprises isobutane, wherein the second bottoms stream is substantially free of olefins.

Embodiment G. A process for component separation in a polymer production system, comprising:

polymerizing olefin monomers in a first polymerization reactor to yield a mid-polymerization product stream;

separating the mid-polymerization product stream into a mid-gas stream and a mid-polymer stream, wherein the mid-gas stream comprises ethane, unreacted ethylene, and hydrogen; and polymerizing the mid-polymer stream in a second polymerization reactor.

Embodiment H. The process of embodiment G, the step of separating comprising reducing a pressure of the mid-polymerization product stream so as to flash ethylene, ethane, hydrogen, or combinations thereof.

Embodiment I. A process for component separation in a polymer production system, comprising:

polymerizing olefin monomers in a first polymerization reactor;

separating a mid-polymerization product stream into a mid-gas stream and a mid-polymer stream, wherein the mid-gas stream comprises ethane and unreacted ethylene;

polymerizing the mid-polymer stream in a second polymerization reactor; and introducing a scavenger prior to the second polymerization reactor.

Embodiment J. The process of embodiment I, the introducing a scavenger prior to the second polymerization reactor comprising introducing the scavenger into the mid-polymerization product stream.

Embodiment K. The process of embodiment I through J, wherein the scavenger comprises a hydrogenation catalyst.

Embodiment L. The process of embodiment I through K, wherein the step of separating comprises:

reducing a pressure of the mid-polymerization product stream so as to flash ethylene and ethane.

Embodiment M. The process of embodiment I through L, wherein the scavenger reduces a concentration of hydrogen prior to the second polymerization reactor.

Embodiment N. A process for component separation in a polymer production system, comprising:

polymerizing olefin monomers in a first polymerization reactor to yield a mid-polymerization product stream;

degassing at least a portion of hydrogen from the mid-polymerization product stream to yield a hydrogen-reduced product stream;

separating the hydrogen-reduced product stream into a mid-gas stream and a mid-polymer stream, wherein the mid-gas stream comprises ethane and unreacted ethylene; and polymerizing the mid-polymer stream in a second polymerization reactor.

Embodiment O. The process of embodiment N, the step of separating comprising reducing a pressure of the hydrogen-reduced product stream so as to flash ethylene and ethane.

Embodiment P. The process of embodiment N through O, wherein an amount of hydrogen in the mid-gas stream comprises less than about 1 wt %.

Embodiment Q. The process of embodiments G through N, further comprising:

contacting the mid-gas stream with an absorption solvent system, wherein at least a portion of the unreacted ethylene from the mid-gas stream is absorbed by the absorption solvent system; and regenerating the absorption solvent system to yield recovered ethylene.

Embodiment R. The process of embodiment Q, further comprising:

recovering a waste gas stream from the absorption solvent system, wherein the waste gas stream comprises ethane.

Embodiment S. The process of embodiments A through F or R, further comprising:

processing the waste gas stream in a processing device.

Embodiment T. The process of embodiment S, wherein the processing device comprises a cracker, catalytic cracker, scrubber, converter, treater, dehydrogenator, deoxygenator, flare or combinations thereof.

Embodiment U. The process of embodiments A through F or Q through T, wherein the absorbent solvent system is configured to operate at a temperature in a range of from about 40° F. to about 110° F.

Embodiment V. The process of embodiments A through F or Q through U, wherein the absorbent solvent system comprises copper chloride, aniline, and N-methylpyrrolidone.

EXAMPLES

The disclosure having been generally described, the following examples are given as particular embodiments of the disclosure and to demonstrate the practice and advantages thereof. It is understood that these examples are given by way of illustration and is not intended to limit the specification or the claims in any manner.

Figure 12:
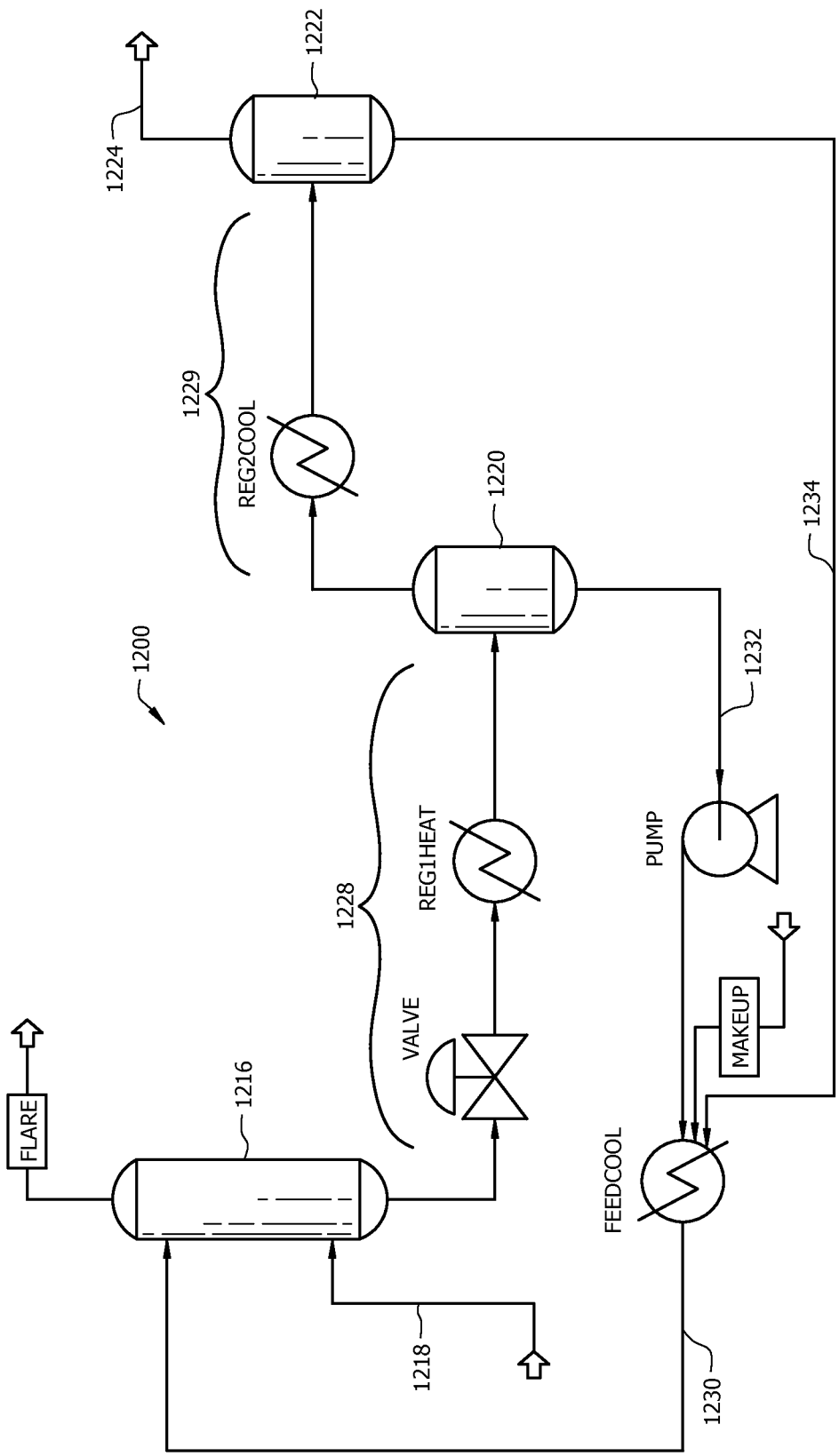
FIG. 12 illustrates a schematic of an embodiment of a simulated absorption system.

A computerized commercial process simulator was employed to generate an output from a model in accordance with the systems and/or processes disclosed herein. The model employed is illustrated at FIG. 12, which shows an embodiment of an absorption system 1200, as disclosed herein, and shall be used to describe the examples below. In the embodiment shown in FIG. 12, a light gas stream 1218, which was separated from a polymerization product stream of a polyethylene reactor 104, 106 disclosed in an embodiment of PEP systems 100, 200, 300, 400, or 500 of FIGS. 1 to 5, feeds to an absorption reactor 1216. The total molar and mass flows and component molar and mass flows of the light gas stream 1218 are shown in Table 1 below:

TABLE 1

| Total Molar Flow (lbmol/hr) | 52.9 | Total Mass Flow (lb/hr) | 1127 |
|---|---|---|---|
| Component Molar Flow (lbmol/hr) | | Component Mass Flow (lb/hr) | |
| Hydrogen | 15.4 | Hydrogen | 31 |
| Nitrogen | 4.9 | Nitrogen | 137 |
| Ethylene | 26 | Ethylene | 729 |
| Ethane | 5.6 | Ethane | 169 |
| Isobutane | 1.1 | Isobutane | 62 |
| Component Molar Fraction | | Component Mass Fraction | |
| Hydrogen | 0.291 | Hydrogen | 0.028 |
| Nitrogen | 0.092 | Nitrogen | 0.121 |
| Ethylene | 0.491 | Ethylene | 0.646 |
| Ethane | 0.106 | Ethane | 0.150 |
| Isobutane | 0.020 | Isobutane | 0.055 |

Unreacted ethylene that enters the absorption reactor 1216 is absorbed in the absorption solvent system within the absorption reactor 1216. Absorbed unreacted ethylene flows, as complexed stream 1228, to a first regenerator 1220. In stream 1228, the absorbed ethylene is heated by heat exchanger REG1HEAT before entering the first regenerator 1220. Ethylene desorbs from the solvent from the absorption solvent system in first regenerator 1220 and flows through stream 1229 to a second regenerator 1222. Stream 1229 may be cooled with heat exchanger REG2COOL before entering the second regenerator 1222. Ethylene is recovered in stream 1224. Absorption solvent in streams 1232 and 2134 combine in heat exchanger FEEDCOOL to recycle to the absorption reactor 1216 in stream 1230.

Table 2 shows operating conditions for examples 1-44 of ethylene recovery using the system 1200 of FIG. 12. For the examples shown in Table 2, the absorption solvent system comprises a copper chloride, aniline, and NMP system, as disclosed herein, and composition of the purified product is based on 90% ethylene recovery. The composition of the purified product recovered from stream 1224 in FIG. 12 comprises ethylene, ethane, nitrogen, hydrogen, and isobutane. The wt % of each of these components in the purified product is shown in Table 2. Select examples from Table 2 are discussed in detail below.

Example 3

In Example 3 of Table 2, the absorption reactor 1216 in FIG. 12 operates at a temperature of 15° F., with a lean solvent temperature of 14° F. and pressure of 40 psig. The first regenerator 120 operates at a temperature of 150° F. and pressure of 0 psig. The second regenerator 122 operates at a temperature of 50° F. and pressure of 0 psig. Under these conditions, system 900 recovers 90% of the ethylene and the solvent circulation flow rate to 344,776 lb/hr and the amount of ethylene in the purified product to 64.5%.

Example 4

In Example 4 of Table 2, the operating conditions are the same as Example 3, except the first regenerator 1220 operates at a temperature of 200° F. and pressure of 0 psig. Under these conditions, system 900 recovers 90% of ethylene for a solvent circulation flow rate of 143,736 lb/hr, and the purified product contains 77.5% ethylene.

Example 7

In Example 7 of Table 2, the absorption reactor 1216 in FIG. 12 operates at a temperature of 53° F., with a lean solvent temperature of 50° F. Absorption reactor 1216 also operates at a pressure of 40 psig. The first regenerator 120 operates at a temperature of 150° F. and a pressure of 0 psig. The second regenerator 1222 operates at a temperature of 50° F. and a pressure of 0 psig. Under these conditions, system 900 recovers 90% of the ethylene for a solvent circulation flow rate of 53,920 lb/hr. The purified product composition for Example 7 is shown in Table 2.

When comparing Example 7 with the Examples 3 and 4, the solvent circulation flow rate of 53,920 lb/hr in Example 7 is less than the flow rates of 143,736 lb/hr and 344,776 lb/hr in the Examples 3 and 4. Thus, Example 7 shows the solvent circulation flow rate required to absorb ethylene in a copper chloride aniline NMP absorption solvent system is much less for an absorption temperature of 53° F. than for an absorption temperature of 15° F. because of the unexpected drop in solubility for ethylene in the absorption solvent system for temperatures below about 50° F.

Example 8

In Example 8 of Table 2, the absorption reactor 1216 in FIG. 12 operates at a temperature of 55° F., with a lean solvent temperature of 50° F. Absorption reactor 1216 also operates at a pressure of 40 psig. The first regenerator 1220 operates at a temperature of 200° F. and a pressure of 0 psig. The second regenerator 1222 operates at a temperature of 50° F. and a pressure of 0 psig. Under these conditions, system 800 recovers 90% of the ethylene for a solvent circulation flow rate of 47,785 lb/hr. The purified product composition for Example 8 is shown in Table 2.

Example 8 confirms the results shown in Example 7 that lower solvent circulation flow rates are required when the absorption reactor 1216 operates at a temperature of 55° F. instead of temperatures below 50° F. Example 2 additionally shows varying the temperature of the regenerator 1220 from 150° F. to 200° F. does not affect the solvent circulation flow rate to a significant degree.

Example 19

In Example 19 of Table 2, the absorption reactor 1216 in FIG. 12 operates at a temperature of 53° F., with a lean solvent temperature of 50° F. Absorption reactor 1216 also operates at a pressure of 40 psig. The first regenerator 1220 operates at a temperature of 200° F. and a pressure of 10 psig. The second regenerator 1222 operates at a temperature of 50° F. and a pressure of 10 psig. Under these conditions, system 1200 recovers 90% of the ethylene for a solvent circulation flow rate of 59,272 lb/hr. The purified product composition is shown in Table 2.

Example 19 confirms the lower solvent circulation rates discussed in Examples 7 and 8 when compared to Examples 3 and 4. Example 19 also shows varying the pressure of the first and second regenerators 1220 and 1222 between 0 psig and 10 psig does not significantly alter results. Operation of the regenerators 1220 and 1222 at 0 psig may provide a lower solvent circulation rate as well as enhanced product purity, and operation of the regenerators 1220 and 1222 at 10 psig may provide a safer design because a positive pressure in the regenerators 1220 and 1222 reduces a chance of air and water infiltration via leaks in the system and process, which may react with copper chloride in the absorption solvent system and inhibit performance.

Example 28

In Example 28 of Table 2, the absorption reactor 1216 in FIG. 12 operates at 52° F., with a lean solvent temperature of 50° F. Absorption reactor 1216 also operates at a pressure of 60 psig. The first regenerator 1220 operates at a temperature of 100° F. and a pressure of 0 psig. The second regenerator 1222 operates at a temperature of 50° F. and a pressure of 0 psig. Under these conditions, system 1200 recovers 90% of the ethylene for a solvent circulation flow rate of 58,613 lb/hr. The purified product composition is shown in Table 2.

Under the conditions in Example 28, the solvent circulation flow rate is less than that of the Examples 3 and 4, and the amount of ethylene in the purified product is significantly higher.

Example 29

In Example 29 of Table 2, the absorption reactor 1216 in FIG. 12 operates at 55° F., with a lean solvent temperature of 50° F. Absorption reactor 1216 also operates at a pressure of 60 psig. The first regenerator 1220 operates at a temperature of 150° F. and a pressure of 0 psig. The second regenerator 1222 operates at a temperature of 50° F. and a pressure of 0 psig. Under these conditions, system 1200 recovers 90% of the ethylene for a circulation flow rate of solvent of 51,106 lb/hr. The purified product composition is shown in Table 2.

Under the conditions in Example 29, the solvent circulation flow rate is less than that of the Examples 3 and 4, and the amount of ethylene in the purified product is significantly higher.

Example 30

In Example 30 of Table 2, the absorption reactor 1216 in FIG. 12 operates at 56° F., with a lean solvent temperature of 50° F. Absorption reactor 1216 also operates at a pressure of 60 psig. The first regenerator 1220 operates at a temperature of 200° F. and a pressure of 0 psig. The second regenerator 1222 operates at a temperature of 50° F. and a pressure of 0 psig. Under these conditions, system 1200 recovers 90% of the ethylene for a circulation flow rate of solvent of 46,744 lb/hr. The purified product composition is shown in Table 2.

Under the conditions in Example 30, the solvent circulation flow rate is less than that of the Examples 3 and 4, and the amount of ethylene in the purified product is significantly higher.

Example 33

In Example 33 of Table 2, the absorption reactor 1216 in FIG. 12 operates at a temperature of 102° F., with a lean solvent temperature of 100° F. Absorption reactor 1216 also operates at a pressure of 60 psig. The first regenerator 1220 operates at a temperature of 200° F. and a pressure of 0 psig. The second regenerator 1222 operates at a temperature of 50° F. and a pressure of 0 psig. Under these conditions, system 900 recovers 90% of the ethylene for a solvent circulation flow rate of 63,435 lb/hr. The purified product composition for Example 33 is shown in Table 2.

Under the conditions in Example 33, the solvent circulation flow rate is less than that of the Examples 3 and 4, and the amount of ethylene in the purified product is significantly higher. Moreover, Example 33 show that operation of the absorption reactor 116 at temperatures higher than the temperatures of maximum solubility shown in the solubility graph, for example, at 102° F. as shown in Example 33, may still prove economically feasible because, for example, solvent circulation flow rates remain low compared with conditions of Examples 3 and 4.

Example 40

In Example 40 of Table 2, the absorption reactor 1216 in FIG. 12 operates at a temperature of 52° F., with a lean solvent temperature of 50° F. Absorption reactor 1216 also operates at a pressure of 60 psig. The first regenerator 1220 operates at a temperature of 150° F. and a pressure of 10 psig. The second regenerator 1222 operates at a temperature of 50° F. and a pressure of 10 psig. Under these conditions, system 1200 recovers 90% of the ethylene for a solvent circulation flow rate of 57,441 lb/hr. The purified product composition for Example 40 is shown in Table 2.

Under the conditions in Example 40, the solvent circulation flow rate is less than that of the Examples 3 and 4, and the amount of ethylene in the purified product is significantly higher.

Example 41

In Example 41 of Table 2, the absorption reactor 1216 in FIG. 12 operates at 55° F., with a lean solvent temperature of 50° F. Absorption reactor 1216 also operates at a pressure of 60 psig. The first regenerator 1220 operates at a temperature of 200° F. and a pressure of 10 psig. The second regenerator 1222 operates at a temperature of 50° F. and a pressure of 10 psig. Under these conditions, system 900 recovers 90% of the ethylene for a circulation flow rate of solvent of 51,482 lb/hr. The purified product composition is shown in Table 2.

Under the conditions in Example 41, the solvent circulation flow rate is less than that of the Examples 3 and 4, and the amount of ethylene in the purified product is significantly higher.

Example Simulation

Figure 13:
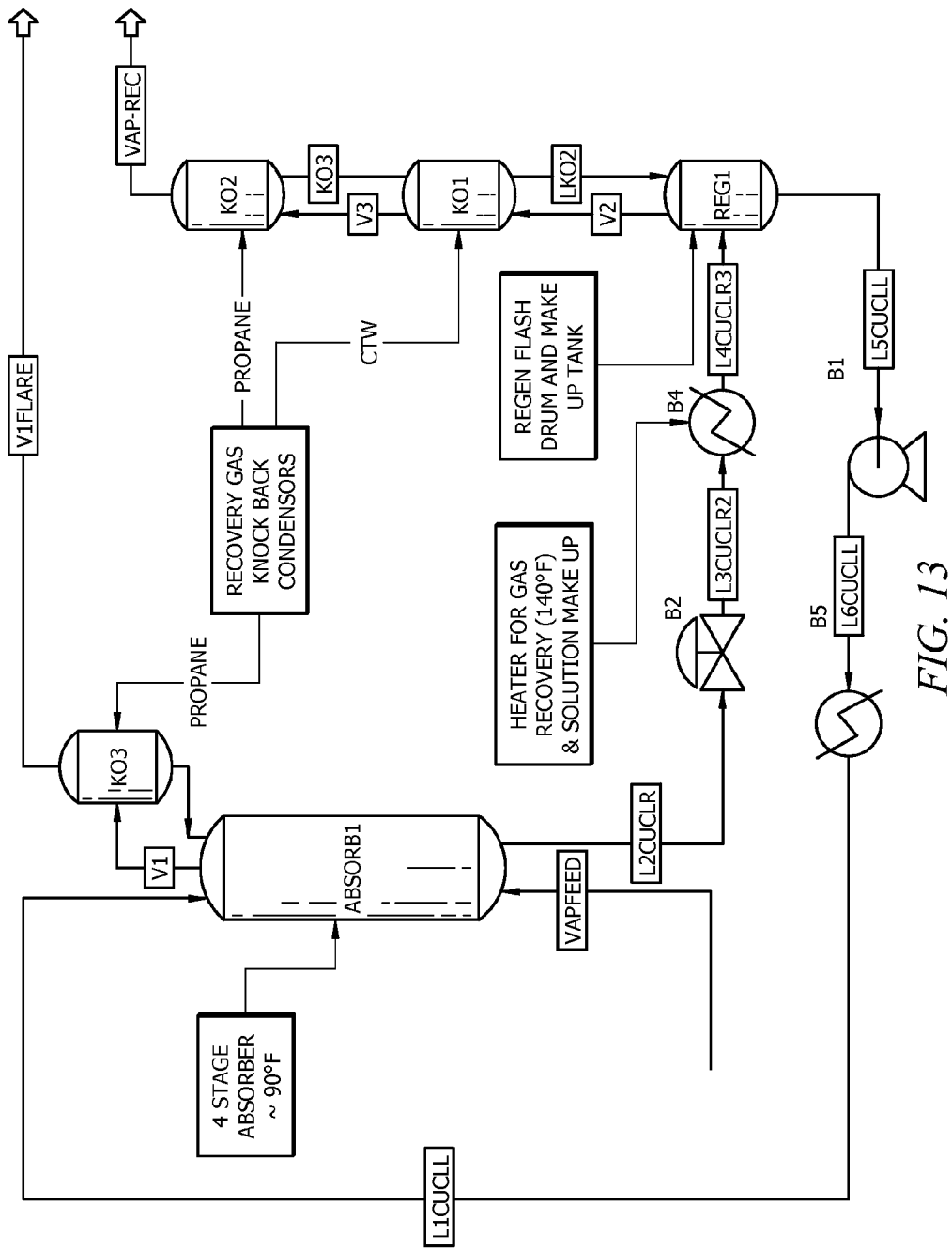
FIG. 13 illustrates a schematic of an embodiment of a simulated absorption system.

A computerized commercial process simulator was employed to generate an output from another model in accordance with the systems and/or processes disclosed herein. The model employed is illustrated at FIG. 13, wherein a gaseous stream, designated VAP FEED (e.g., the light gas stream disclosed herein) feeds to absorption reactor ASORB1. The output generated by the commercial process simulator is a material balance and a heat balance, shown in Table 3. The names designating the various streams listed in Table 3 correspond to streams illustrated in FIG. 10. In FIG. 13, ASORB1 is the absorption reactor, which is shown as a four stage absorber operating at 90° F.

TABLE 2

| Example | Lean Solvent Temp. (°F.) | Absorber top temperature (°F.) | REG1 temperature (°F.) | REG2 temperature (°F.) | Absorber pressure (psig) | REG1 temperature (psig) | REG2 temperature (psig) | Ethylene Recovery | Flow rate of circulation solvent (lb/hr) | Ethylene (wt %) | Ethane (wt %) | Nitrogen (wt %) | Hydrogen (wt %) | Isobutane (wt %) |
|---|---|---|---|---|---|---|---|---|---|---|---|---|---|---|
| 1 | 14 | 15 | 50 | 50 | 40 | 0 | 0 | 90% | 1704044 | 48.9% | 11.6% | 10.0% | 27.2% | 2.2% |
| 2 | 14 | 15 | 100 | 50 | 40 | 0 | 0 | 90% | 731337 | 57.7% | 13.0% | 11.1% | 18.9% | 2.3% |
| 3 | 14 | 15 | 150 | 50 | 40 | 0 | 0 | 90% | 344776 | 64.5% | 15.2% | 8.5% | 9.5% | 2.2% |
| 4 | 14 | 15 | 200 | 50 | 40 | 0 | 0 | 90% | 143736 | 77.5% | 16.3% | 2.1% | 3.3% | 0.8% |
| 5 | 50 | 50 | 50 | 50 | 40 | 0 | 0 | 90% | 672565 | 62.1% | 13.3% | 7.0% | 15.1% | 2.5% |
| 6 | 50 | 51 | 100 | 50 | 40 | 0 | 0 | 90% | 158735 | 81.9% | 11.2% | 1.8% | 4.1% | 1.0% |
| 7 | 50 | 53 | 150 | 50 | 40 | 0 | 0 | 90% | 53920 | 95.9% | 2.3% | 0.5% | 1.1% | 0.3% |
| 8 | 50 | 55 | 200 | 50 | 40 | 0 | 0 | 90% | 47785 | 96.5% | 1.9% | 0.4% | 1.0% | 0.3% |
| 9 | 100 | 100 | 50 | 50 | 40 | 0 | 0 | 90% | 921807 | 62.1% | 13.0% | 7.1% | 15.3% | 2.5% |
| 10 | 100 | 100 | 100 | 50 | 40 | 0 | 0 | 90% | 343211 | 78.4% | 9.5% | 3.2% | 7.1% | 1.9% |
| 11 | 100 | 101 | 150 | 50 | 40 | 0 | 0 | 90% | 88403 | 95.6% | 1.9% | 0.7% | 1.4% | 0.4% |
| 12 | 100 | 100 | 200 | 50 | 40 | 0 | 0 | N/A | | | | | | |
| 13 | 14 | 15 | 50 | 50 | 40 | 10 | 10 | 90% | 1321719 | 50.3% | 12.0% | 10.2% | 25.3% | 2.2% |
| 14 | 14 | 15 | 100 | 50 | 40 | 10 | 10 | 90% | 685442 | 56.2% | 13.3% | 10.6% | 17.7% | 2.3% |
| 15 | 14 | 14 | 150 | 50 | 40 | 10 | 10 | 90% | 420362 | 64.1% | 14.8% | 7.1% | 11.7% | 2.4% |
| 16 | 50 | 50 | 200 | 50 | 40 | 10 | 10 | 90% | 1367657 | 54.8% | 11.8% | 9.0% | 22.2% | 2.2% |
| 17 | 50 | 50 | 50 | 50 | 40 | 10 | 10 | 90% | 463945 | 66.9% | 14.6% | 5.1% | 11.1% | 2.3% |
| 18 | 50 | 51 | 100 | 50 | 40 | 10 | 10 | 90% | 121635 | 86.6% | 8.1% | 1.3% | 3.1% | 0.8% |
| 19 | 50 | 53 | 150 | 50 | 40 | 10 | 10 | 90% | 59272 | 95.6% | 2.5% | 0.5% | 1.2% | 0.3% |
| 20 | 100 | 100 | 200 | 50 | 40 | 10 | 10 | 90% | 1828349 | 54.8% | 11.6% | 9.0% | 22.3% | 2.2% |
| 21 | 100 | 100 | 50 | 50 | 40 | 10 | 10 | 90% | 880270 | 64.5% | 12.7% | 5.7% | 14.7% | 2.4% |
| 22 | 100 | 100 | 100 | 50 | 40 | 10 | 10 | 90% | 415884 | 77.5% | 9.6% | 2.3% | 8.4% | 2.1% |
| 23 | 14 | 15 | 150 | 50 | 60 | 0 | 0 | 90% | 858069 | 50.7% | 12.0% | 10.4% | 24.7% | 2.2% |
| 24 | 14 | 15 | 200 | 50 | 60 | 0 | 0 | 90% | 384021 | 58.5% | 13.9% | 11.4% | 13.7% | 2.5% |
| 25 | 14 | 15 | 50 | 50 | 60 | 0 | 0 | 90% | 159379 | 71.6% | 16.9% | 4.5% | 5.6% | 1.4% |
| 26 | 14 | 16 | 100 | 50 | 60 | 0 | 0 | 90% | 93956 | 82.2% | 12.7% | 1.7% | 2.8% | 0.7% |
| 27 | 50 | 50 | 150 | 50 | 60 | 0 | 0 | 90% | 296859 | 68.5% | 14.6% | 4.6% | 9.8% | 2.5% |
| 28 | 50 | 52 | 200 | 50 | 60 | 0 | 0 | 90% | 58613 | 93.9% | 3.4% | 0.7% | 1.6% | 0.4% |
| 29 | 50 | 55 | 50 | 50 | 60 | 0 | 0 | 90% | 51106 | 94.7% | 2.9% | 0.6% | 1.4% | 0.4% |
| 30 | 50 | 56 | 100 | 50 | 60 | 0 | 0 | 90% | 46744 | 95.3% | 2.6% | 0.5% | 1.3% | 0.3% |
| 31 | 100 | 100 | 150 | 50 | 60 | 0 | 0 | 90% | 428830 | 68.5% | 13.3% | 5.0% | 10.6% | 2.6% |
| 32 | 100 | 100 | 200 | 50 | 60 | 0 | 0 | 90% | 111161 | 90.5% | 4.1% | 1.5% | 3.0% | 0.9% |
| 33 | 100 | 102 | 50 | 50 | 60 | 0 | 0 | 90% | 63435 | 95.7% | 1.8% | 0.7% | 1.4% | 0.4% |
| 34 | 100 | 100 | 100 | 50 | 60 | 0 | 0 | N/A | | | | | | |
| 35 | 14 | 14 | 150 | 50 | 60 | 10 | 10 | 90% | 693610 | 52.5% | 12.5% | 10.6% | 22.1% | 2.3% |
| 36 | 14 | 15 | 200 | 50 | 60 | 10 | 10 | 90% | 346101 | 60.5% | 14.3% | 10.5% | 12.3% | 2.4% |
| 37 | 14 | 15 | 50 | 50 | 60 | 10 | 10 | 90% | 181196 | 71.0% | 16.3% | 4.4% | 6.7% | 1.6% |
| 38 | 50 | 50 | 100 | 50 | 60 | 10 | 10 | 90% | 669442 | 58.7% | 12.6% | 8.2% | 18.2% | 2.3% |
| 39 | 50 | 51 | 150 | 50 | 60 | 10 | 10 | 90% | 179196 | 75.0% | 15.2% | 2.6% | 5.8% | 1.4% |
| 40 | 50 | 52 | 200 | 50 | 60 | 10 | 10 | 90% | 57441 | 94.1% | 3.3% | 0.7% | 1.6% | 0.4% |
| 41 | 50 | 55 | 50 | 50 | 60 | 10 | 10 | 90% | 51482 | 94.8% | 2.9% | 0.5% | 1.4% | 0.4% |
| 42 | 100 | 100 | 100 | 50 | 60 | 10 | 10 | 90% | 896707 | 58.7% | 12.4% | 8.3% | 18.3% | 2.4% |
| 43 | 100 | 100 | 150 | 50 | 60 | 10 | 10 | 90% | 378813 | 71.8% | 12.1% | 4.1% | 9.6% | 2.4% |
| 44 | 100 | 100 | 200 | 50 | 60 | 10 | 10 | 90% | 130215 | 89.1% | 4.8% | 14.3% | 3.7% | 1.1% |

TABLE 3

| | L1CUCLL | L2CUCLR | L3CUCLR2 | L4CUCLR3 | L5CUCLL | L6CUCLL | LKO1 | LKO2 |
|---|---|---|---|---|---|---|---|---|
| Substream: MIXED | | | | | | | | |
| Mole Flow lbmol/hr | | | | | | | | |
| C2= | 1.949416 | 41.85801 | 41.85801 | 41.85801 | 1.949413 | 1.949413 | 2.02E−04 | 4.41E−03 |
| C2 | 0.9764562 | 5.916248 | 5.916248 | 5.916248 | 0.9764532 | 0.9764532 | 6.17E−04 | 8.14E−04 |
| N2 | 1.15E−03 | 0.1711679 | 0.1711679 | 0.1711679 | 1.15E−03 | 1.15E−03 | 8.35E−06 | 8.99E−07 |
| IC4 | 0.8615088 | 3.112527 | 3.112527 | 3.112527 | 0.8615092 | 0.8615092 | 2.14E−04 | 2.23E−03 |
| CUCL | 131.4402 | 131.4402 | 131.4402 | 131.4402 | 131.4402 | 131.4402 | 1.50E−13 | 2.85E−13 |
| ANILINE | 580.5749 | 580.5749 | 580.5749 | 580.5749 | 580.5748 | 580.5748 | 2.47E−03 | 0.2059512 |
| NMP | 789.7864 | 789.7864 | 789.7864 | 789.7864 | 789.7864 | 789.7864 | 2.38E−03 | 0.1961199 |
| Mole Frac | | | | | | | | |
| C2= | 1.29E−03 | 0.0269554 | 0.0269554 | 0.0269554 | 1.29E−03 | 1.29E−03 | 0.0343637 | 0.0107758 |
| C2 | 6.49E−04 | 3.81E−03 | 3.81E−03 | 3.81E−03 | 6.49E−04 | 6.49E−04 | 0.1047838 | 1.99E−03 |
| N2 | 7.64E−07 | 1.10E−04 | 1.10E−04 | 1.10E−04 | 7.64E−07 | 7.64E−07 | 1.42E−03 | 2.19E−06 |
| IC4 | 5.72E−04 | 2.00E−03 | 2.00E−03 | 2.00E−03 | 5.72E−04 | 5.72E−04 | 0.0362971 | 5.44E−03 |
| CUCL | 0.0873014 | 0.0846439 | 0.0846439 | 0.0846439 | 0.0873014 | 0.0873014 | 2.54E−11 | 6.97E−13 |
| ANILINE | 0.3856129 | 0.3738747 | 0.3738747 | 0.3738747 | 0.3856128 | 0.3856128 | 0.4198489 | 0.5029009 |
| NMP | 0.5245694 | 0.5086013 | 0.5086013 | 0.5086013 | 0.5245694 | 0.5245694 | 0.4032882 | 0.4788945 |
| Mass Flow lb/hr | | | | | | | | |
| C2= | 54.68846 | 1174.274 | 1174.274 | 1174.274 | 54.68837 | 54.68837 | 5.68E−03 | 0.1238009 |
| C2 | 29.36169 | 177.8994 | 177.8994 | 177.8994 | 29.3616 | 29.3616 | 0.0185606 | 0.0244775 |
| N2 | 0.0322059 | 4.795009 | 4.795009 | 4.795009 | 0.0322058 | 0.0322058 | 2.34E−04 | 2.52E−05 |
| IC4 | 50.07382 | 180.9106 | 180.9106 | 180.9106 | 50.07384 | 50.07384 | 0.0124277 | 0.129461 |
| CUCL | 13012.41 | 13012.41 | 13012.41 | 13012.41 | 13012.41 | 13012.41 | 1.48E−11 | 2.83E−11 |
| ANILINE | 54067.97 | 54067.97 | 54067.97 | 54067.97 | 54067.96 | 54067.96 | 0.2303272 | 19.17989 |
| NMP | 78293.58 | 78293.58 | 78293.58 | 78293.58 | 78293.58 | 78293.58 | 0.2355062 | 19.44187 |
| Mass Frac | | | | | | | | |
| C2= | 3.76E−04 | 7.99E−03 | 7.99E−03 | 7.99E−03 | 3.76E−04 | 3.76E−04 | 0.0112959 | 3.18E−03 |
| C2 | 2.02E−04 | 1.21E−03 | 1.21E−03 | 1.21E−03 | 2.02E−04 | 2.02E−04 | 0.0369193 | 6.29E−04 |
| N2 | 2.21E−07 | 3.26E−05 | 3.26E−05 | 3.26E−05 | 2.21E−07 | 2.21E−07 | 4.66E−04 | 6.47E−07 |
| IC4 | 3.44E−04 | 1.23E−03 | 1.23E−03 | 1.23E−03 | 3.44E−04 | 3.44E−04 | 0.0247203 | 3.33E−03 |
| CUCL | 0.0894273 | 0.0885729 | 0.0885729 | 0.0885729 | 0.0894273 | 0.0894273 | 2.95E−11 | 7.26E−13 |
| ANILINE | 0.3715804 | 0.36803 | 0.36803 | 0.36803 | 0.3715804 | 0.3715804 | 0.4581486 | 0.4930622 |
| NMP | 0.5380702 | 0.532929 | 0.532929 | 0.532929 | 0.5380702 | 0.5380702 | 0.4684502 | 0.4997972 |
| Total Flow lbmol/hr | 1505.59 | 1552.86 | 1552.86 | 1552.86 | 1505.59 | 1505.59 | 5.89E−03 | 0.4095263 |
| Total Flow lb/hr | 145508 | 1.47E+05 | 1.47E+05 | 1.47E+05 | 1.46E+05 | 1.46E+05 | 0.5027346 | 38.89952 |
| Total Flow cuft/hr | 2000 | 2063.515 | 9563.191 | 13833 | 2058.304 | 2058.521 | 8.16E−03 | 0.6204605 |
| Temperature F. | 90 | 105.0961 | 95.53801 | 140 | 158 | 158.2431 | −20 | 90 |
| Pressure psia | 117.6959 | 114.6959 | 25 | 25 | 25 | 118.6959 | 114.6959 | 24.9 |
| Vapor Frac | 0 | 0 | 0.020591 | 0.0297334 | 0 | 0 | 0 | 0 |
| Liquid Frac | 1 | 1 | 0.9794089 | 0.9702665 | 1 | 1 | 1 | 1 |
| Solid Frac | 0 | 0 | 0 | 0 | 0 | 0 | 0 | 0 |
| Enthalpy Btu/lbmol | −60439.71 | −58273.13 | −58273.13 | −56229.58 | −57622.43 | −57585.8 | −49592.05 | −47471.61 |
| Enthalpy Btu/lb | −625.377 | −615.9475 | −615.9475 | −594.3472 | −596.2263 | −595.8472 | −581.0902 | −499.7715 |
| Enthalpy Btu/hr | −9.10E+07 | −9.05E+07 | −9.05E+07 | −8.73E+07 | −8.68E+07 | −8.67E+07 | −292.1342 | −19440.87 |
| Entropy Btu/lbmol-R | −112.3696 | −109.6524 | −109.5691 | −106.0242 | −107.4881 | −107.4788 | −111.4813 | −112.727 |
| Entropy Btu/lb-R | −1.162701 | −1.159027 | −1.158146 | −1.120676 | −1.112192 | −1.112096 | −1.306271 | −1.186767 |
| Density lbmol/cuft | 0.75276 | 0.7525312 | 0.1623788 | 0.1122576 | 0.7314713 | 0.731394 | 0.7221323 | 0.6600361 |
| Density lb/cuft | 72.75067 | 71.19494 | 15.36222 | 10.62039 | 70.69322 | 70.68575 | 61.62902 | 62.6946 |
| Average MW | 96.64524 | 94.6073 | 94.6073 | 94.6073 | 96.64524 | 96.64524 | 85.34311 | 94.98663 |
| Liq Vol 60 F. cuft/hr | 2474.029 | 2538.765 | 2538.765 | 2538.765 | 2474.029 | 2474.029 | 8.78E−03 | 0.6165612 |

| | LKO3 | V1 | V1FLARE | V2 | V3 | VAP-REC | VAPFEED |
|---|---|---|---|---|---|---|---|
| Substream: MIXED | | | | | | | |
| Mole Flow lbmol/hr | | | | | | | |
| C2= | 9.89E−04 | 3.172776 | 3.172573 | 39.91302 | 39.9096 | 39.90861 | 43.08116 |
| C2 | 2.10E−04 | 5.654325 | 5.653708 | 4.940621 | 4.940017 | 4.939807 | 10.5935 |

TABLE 3-continued

|  | | | | | | | |
|---|---|---|---|---|---|---|---|
| N2 | 6.78E−08 | 7.187729 | 7.187721 | 0.1700194 | 0.1700186 | 0.1700185 | 7.357739 |
| IC4 | 1.08E−03 | 0.1670439 | 0.1668301 | 2.253242 | 2.252096 | 2.251014 | 2.417848 |
| CUCL | 0 | 1.50E−13 | 4.78E−22 | 2.85E−13 | 2.86E−24 | 0 | 0 |
| ANILINE | 0.0219362 | 2.48E−03 | 9.19E−06 | 0.20608 | 0.022065 | 1.29E−04 | 0 |
| NMP | 9.42E−03 | 2.38E−03 | 3.17E−06 | 0.1961404 | 9.44E−03 | 2.06E−05 | 0 |
| Mole Frac | | | | | | | |
| C2= | 0.0294004 | 0.1960108 | 0.1960697 | 0.8371173 | 0.843697 | 0.8442764 | 0.6789755 |
| C2 | 6.25E−03 | 0.3493185 | 0.3494075 | 0.1036223 | 0.104433 | 0.1045028 | 0.1669576 |
| N2 | 2.02E−06 | 0.4440506 | 0.4442117 | 3.57E−03 | 3.59E−03 | 3.60E−03 | 0.1159608 |
| IC4 | 0.032152 | 0.0103198 | 0.0103103 | 0.0472584 | 0.0476097 | 0.0476207 | 0.0381062 |
| CUCL | 0 | 9.24E−15 | 2.95E−23 | 5.99E−15 | 6.04E−26 | 0 | 0 |
| ANILINE | 0.6521121 | 1.53E−04 | 5.68E−07 | 4.32E−03 | 4.66E−04 | 2.73E−06 | 0 |
| NMP | 0.2800845 | 1.47E−04 | 1.96E−07 | 4.11E−03 | 2.00E−04 | 4.36E−07 | 0 |
| Mass Flow lb/hr | | | | | | | |
| C2= | 0.027745 | 89.00829 | 89.00261 | 1119.71 | 1119.614 | 1119.587 | 1208.589 |
| C2 | 6.32E−03 | 170.0235 | 170.005 | 148.5627 | 148.5445 | 148.5382 | 318.5427 |
| N2 | 1.90E−06 | 201.3533 | 201.3531 | 4.762835 | 4.762812 | 4.76281 | 206.1159 |
| IC4 | 0.0628636 | 9.709158 | 9.69673 | 130.9661 | 130.8995 | 130.8366 | 140.5336 |
| CUCL | 0 | 1.48E−11 | 4.73E−20 | 2.83E−11 | 2.83E−22 | 0 | 0 |
| ANILINE | 2.042886 | 0.2311832 | 8.56E−04 | 19.19188 | 2.054883 | 0.0120247 | 0 |
| NMP | 0.9339974 | 0.2358215 | 3.14E−04 | 19.4439 | 0.9360284 | 2.04E−03 | 0 |
| Mass Frac | | | | | | | |
| C2= | 9.03E−03 | 0.1891534 | 0.1893437 | 0.7761549 | 0.7958521 | 0.797575 | 0.645 |
| C2 | 2.06E−03 | 0.3613207 | 0.3616676 | 0.1029799 | 0.1055895 | 0.1058162 | 0.17 |
| N2 | 6.18E−07 | 0.4279003 | 0.4283574 | 3.30E−03 | 3.39E−03 | 3.39E−03 | 0.11 |
| IC4 | 0.0204513 | 0.0206331 | 0.0206287 | 0.0907823 | 0.0930468 | 0.0932058 | 0.075 |
| CUCL | 0 | 3.15E−14 | 1.01E−22 | 1.96E−14 | 2.01E−25 | 0 | 0 |
| ANILINE | 0.6646093 | 4.91E−04 | 1.82E−06 | 0.0133033 | 1.46E−03 | 8.57E−06 | 0 |
| NMP | 0.3038561 | 5.01E−04 | 6.69E−07 | 0.013478 | 6.65E−04 | 1.46E−06 | 0 |
| Total Flow lbmol/hr | 0.0336387 | 16.18674 | 16.18085 | 47.67913 | 47.30324 | 47.2696 | 63.45025 |
| Total Flow lb/hr | 3.073815 | 470.5613 | 470.0586 | 1442.638 | 1406.812 | 1403.738 | 1873.781 |
| Total Flow cuft/hr | 0.04765 | 825.9148 | 634.7071 | 12547.34 | 11089.96 | 8812.544 | 1155.656 |
| Temperature F. | −20 | 96.94405 | −20 | 158 | 90 | −20 | 0 |
| Pressure psia | 24.8 | 114.6959 | 114.6959 | 25 | 24.9 | 24.8 | 226.6959 |
| Vapor Frac | 0 | 1 | 1 | 1 | 1 | 1 | 0.9823996 |
| Liquid Frac | 1 | 0 | 0 | 0 | 0 | 0 | 0.0176004 |
| Solid Frac | 0 | 0 | 0 | 0 | 0 | 0 | 0 |
| Enthalpy Btu/lbmol | −28177.63 | −8659.402 | −9795.256 | 13137.72 | 12629.88 | 11470.01 | 5793.013 |
| Enthalpy Btu/lb | −308.3662 | −297.8729 | −337.1825 | 434.201 | 424.6725 | 386.242 | 196.1639 |
| Enthalpy Btu/hr | −947.8608 | −1.40E+05 | −1.59E+05 | 6.26E+05 | 5.97E+05 | 5.42E+05 | 3.68E+05 |
| Entropy Btu/lbmol-R | −110.4079 | −19.64671 | −21.92954 | −18.274 | −19.22263 | −21.55552 | −25.0739 |
| Entropy Btu/lb-R | −1.208266 | −0.6758228 | −0.7548814 | −0.603955 | −0.6463497 | −0.7258623 | −0.8490563 |
| Density lbmol/cuft | 0.7059546 | 0.0195985 | 0.0254934 | 3.80E−03 | 4.27E−03 | 5.36E−03 | 0.0549041 |
| Density lb/cuft | 64.50811 | 0.5697456 | 0.7405913 | 0.1149756 | 0.1268545 | 0.1592887 | 1.6214 |
| Average MW | 91.37714 | 29.0708 | 29.05031 | 30.25722 | 29.74029 | 29.69643 | 29.5315 |
| Liq Vol 60 F. cuft/hr | 0.0501975 | 18.42872 | 18.41994 | 65.35257 | 64.78621 | 64.73601 | 83.15566 |

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the disclosed inventive subject matter. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural or other details supplementary to the disclosure.

We claim:

1. A process for component separation in a polymer production system, comprising:
separating a polymerization product stream into a gas stream and a polymer stream, wherein the gas stream comprises ethane and unreacted ethylene;
distilling the gas stream, in a single distillation column, into a light hydrocarbon stream and a side stream, wherein the light hydrocarbon stream comprises ethane and unreacted ethylene, wherein the side stream comprises isobutane;
contacting the light hydrocarbon stream with an absorption solvent system, wherein at least a portion of the unreacted ethylene from the light hydrocarbon stream is absorbed by the absorption solvent system; and
recovering a waste gas stream from the absorption solvent system, wherein the waste gas stream comprises ethane, hydrogen, or combinations thereof.

2. The process of claim 1, further comprising:
regenerating the absorption solvent system to yield recovered ethylene.

3. The process of claim 1, further comprising:
processing the waste gas stream in a processing device.

4. The process of claim 3, wherein the processing device comprises a cracker, catalytic cracker, scrubber, converter, treater, dehydrogenator, deoxygenator, flare or combinations thereof.

5. The process of claim 1, wherein the absorbent solvent system is configured to operate at a temperature in a range of from about 40° F. to about 110° F.

6. A process for component separation in a polymer production system, comprising:
separating a polymerization product stream into a gas stream and a polymer stream, wherein the gas stream comprises ethane and unreacted ethylene;
distilling the gas stream into a light hydrocarbon stream and a side stream, wherein the light hydrocarbon stream comprises ethane and unreacted ethylene, wherein the side stream comprises isobutane;
contacting the light hydrocarbon stream with an absorption solvent system, wherein at least a portion of the unreacted ethylene from the light hydrocarbon stream is absorbed by the absorption solvent system; and
recovering a waste gas stream from the absorption solvent system, wherein the waste gas stream comprises ethane, hydrogen, or combinations thereof,
wherein the absorption solvent system comprises copper chloride, aniline, and N-methylpyrrolidone.

7. The process of claim 1, wherein the light hydrocarbon stream further comprises hydrogen.

8. The process of claim 1, further comprising:
removing oxygen from the gas stream before distilling the gas stream.

9. The process of claim 1, wherein ethylene is present in the light hydrocarbon stream in an amount of from about 50% to about 99% by total weigh of the light hydrocarbon stream.

10. The process of claim 1, wherein the side stream is substantially olefin-free.

11. A process for component separation in polymer production system, comprising:
separating a polymerization product stream into a gas stream and a polymer stream, wherein the gas stream comprise ethane, unreacted ethylene, and one or more of oxygen, oxygenated compounds, and oxidizing compounds;
removing oxygen from the gas stream to yield a treated gas stream comprising ethane and unreacted ethylene;
distilling the treated gas stream into an intermediate hydrocarbon stream, a side stream comprising hexene, and a first bottoms stream, wherein the intermediate hydrocarbon stream comprises ethane, ethylene, and isobutane;
distilling the intermediate hydrocarbon stream into a light hydrocarbon stream and a second bottoms stream, wherein the light hydrocarbon stream comprises ethane and ethylene;
contacting the light hydrocarbon stream with an absorption solvent system, wherein at least a portion of the unreacted ethylene from the light hydrocarbon stream is absorbed by the absorption solvent system; and
recovering a waste gas stream from the absorption solvent system, wherein the waste gas stream comprises ethane, hydrogen, or combinations thereof.

12. The process of claim 11, further comprising:
regenerating the absorption solvent system to yield recovered ethylene.

13. The process of claim 11, further comprising:
distilling the intermediate hydrocarbon stream into a side stream comprising isobutene, wherein the second bottoms stream comprises isobutane, wherein the second bottoms stream is substantially free of olefins.

14. The process of claim 11, wherein the treated gas stream is substantially free of oxygen.

15. The process of claim 11, wherein hexene is present in the side stream in an amount of from about 20% to about 98% by total weight of the side stream.

16. The process of claim 11, wherein $C_4$ and lighter hydrocarbons and gases are present in the intermediate hydrocarbon stream in an amount of from about 80% to about 100% by total weight of the intermediate hydrocarbon stream.

17. The process of claim 11, wherein distilling the gas stream is performed at a temperature in a range of from about 20° C. to about 50° C.

18. The process of claim 11, wherein distilling the intermediate hydrocarbon stream is performed at a temperature in a range of from about 15° C. to about 233° C.

19. The process of claim 11, wherein the light hydrocarbon stream further comprises hydrogen.

* * * * *